US009399639B2

(12) United States Patent
Xi et al.

(10) Patent No.: US 9,399,639 B2
(45) Date of Patent: Jul. 26, 2016

(54) SUBSTITUTED AZAINDOLE COMPOUNDS, SALTS, PHARMACEUTICAL COMPOSITIONS THEREOF AND METHODS OF USE

(71) Applicants: Calitor Sciences, LLC, Newbury Park, CA (US); Sunshine Lake Pharma Co.. Ltd., Dongguan, Guangdong (CN)

(72) Inventors: Ning Xi, Newbury Park, CA (US); Tingjin Wang, Guangdong (CN); Yin Tang, Guangdong (CN); Mingming Sun, Guangdong (CN); Qian Wang, Guangdong (CN)

(73) Assignees: CALITOR SCIENCES, LLC, Newbury Park, CA (US); SUNSHINE LAKE PHARMA CO., LTD., Dongguan, Guangdong (CN)

( * ) Notice: Subject to any disclaimer, the term of this patent is extended or adjusted under 35 U.S.C. 154(b) by 101 days.

(21) Appl. No.: 13/975,371

(22) Filed: Aug. 26, 2013

(65) Prior Publication Data
US 2014/0056849 A1    Feb. 27, 2014

Related U.S. Application Data

(60) Provisional application No. 61/693,335, filed on Aug. 27, 2012.

(51) Int. Cl.
| | | |
|---|---|---|
| *C07D 401/02* | (2006.01) | |
| *C07D 401/10* | (2006.01) | |
| *A61K 31/437* | (2006.01) | |
| *A61K 31/4353* | (2006.01) | |
| *C07D 471/04* | (2006.01) | |
| *A61K 45/06* | (2006.01) | |

(52) U.S. Cl.
CPC ............ *C07D 471/04* (2013.01); *A61K 31/437* (2013.01); *A61K 45/06* (2013.01)

(58) Field of Classification Search
CPC .. C07D 401/02; C07D 401/10; A61K 31/437; A61K 31/4353
USPC .......................................... 546/113; 514/300
See application file for complete search history.

(56) References Cited

U.S. PATENT DOCUMENTS

| | | | |
|---|---|---|---|
| 7,589,233 B2 | 9/2009 | Chandran | |
| 7,812,143 B2 * | 10/2010 | Pratilas et al. | 536/23.1 |
| 7,863,288 B2 * | 1/2011 | Ibrahim et al. | 514/300 |
| 7,863,289 B2 | 1/2011 | Spevak et al. | |
| 8,143,271 B2 | 3/2012 | Ibrahim et al. | |
| 8,173,840 B2 | 5/2012 | Chandran | |
| 8,188,311 B2 | 5/2012 | Chandran | |
| 8,198,273 B2 | 6/2012 | Ibrahim et al. | |
| 8,268,858 B2 | 9/2012 | Wu et al. | |
| 8,329,724 B2 | 12/2012 | Hildbrand et al. | |
| 8,415,469 B2 | 4/2013 | Ibrahim et al. | |
| 8,470,818 B2 | 6/2013 | Ibrahim et al. | |
| 8,530,661 B2 | 9/2013 | Hildbrand et al. | |
| 8,563,776 B2 | 10/2013 | Chandran | |
| 8,741,920 B2 | 6/2014 | Hildbrand et al. | |
| 8,901,301 B2 | 12/2014 | Ibrahim et al. | |
| 9,150,570 B2 | 10/2015 | Ibrahim | |
| 2010/0069489 A1 | 3/2010 | Chandran | |
| 2011/0092538 A1 | 4/2011 | Spevak et al. | |
| 2011/0183988 A1 | 7/2011 | Ibrahim et al. | |
| 2012/0053177 A1 | 3/2012 | Ibrahim et al. | |
| 2012/0122860 A1 | 5/2012 | Visor et al. | |
| 2012/0208837 A1 | 8/2012 | Tung | |
| 2012/0245174 A1 | 9/2012 | Ibrahim et al. | |
| 2012/0289471 A1 | 11/2012 | Chandran | |
| 2013/0261117 A1 | 10/2013 | Ibrahim et al. | |
| 2013/0303534 A1 | 11/2013 | Ibrahim et al. | |
| 2014/0128373 A1 | 5/2014 | Ibrahim et al. | |
| 2015/0080372 A1 | 3/2015 | Ibrahim et al. | |
| 2015/0290205 A1 | 10/2015 | Ibrahim et al. | |
| 2015/0368243 A1 | 12/2015 | Ibrahim et al. | |

FOREIGN PATENT DOCUMENTS

| | | | |
|---|---|---|---|
| CN | 102603734 | | 7/2012 |
| CN | 102838596 | * | 12/2012 |
| WO | 2007002325 | * | 1/2007 |
| WO | 2007002433 | | 1/2007 |
| WO | 2008082730 | * | 7/2008 |
| WO | 2011015522 | * | 2/2011 |
| WO | 2011060216 | | 5/2011 |
| WO | 2013181415 | * | 12/2013 |

OTHER PUBLICATIONS

Jana et al., Prodrug Design to Improve Pharmacokinetic and Drug Delivery Properties: Challenges to the Discovery Scientists, Current Medicinal Chemistry, 2010, vol. 17, Issue 35, p. 3874-3908.
Simplicio et al., Prodrugs for Amines, Molecules, 2008, vol. 13, Issue 13, p. 519-547.
ISR of PCT/US2013/056548.
Written Opinion of PCT/US2013/056548.
The extended European search report of EP13832403.3.

* cited by examiner

*Primary Examiner* — Niloofar Rahmani
(74) *Attorney, Agent, or Firm* — Kam W. Law; Squire Patton Boggs (US) LLP

(57) ABSTRACT

The present invention provides substituted azaindole prodrugs, methods of making said prodrugs, pharmaceutical compositions of said prodrugs and methods of using said prodrugs and pharmaceutical compositions thereof to treat or prevent diseases or disorders such as cancer.

14 Claims, No Drawings

SUBSTITUTED AZAINDOLE COMPOUNDS, SALTS, PHARMACEUTICAL COMPOSITIONS THEREOF AND METHODS OF USE

CROSS-REFERENCE TO RELATED APPLICATION

This application claims the benefit of U.S. Provisional Application Ser. No. 61/693,335, filed on Aug. 27, 2012, which is hereby incorporated by reference in its entirety.

FIELD OF THE INVENTION

The present invention relates generally to substituted azaindole prodrugs, methods of making said prodrugs, pharmaceutical compositions of said prodrugs and methods of using said prodrugs and pharmaceutical compositions of using said prodrugs to treat or prevent diseases or disorders such as cancer.

BACKGROUND OF THE INVENTION

The information provided herein is intended solely to assist the understanding of the reader. None of the information provided nor references cited is admitted to be prior art to the present invention. Each of the references cited herein is incorporated herein by reference in its entirety.

Kinases are a large family of proteins that have now become firmly established as a major class of drug targets. The sequencing of the Human Genome has led to the identification of over 500 protein kinases encoded within it: the Human Kinome. These protein kinases have been grouped into a total of seven families, based on their structures. The 388 serine/threonine kinases fall into five families: AGC, CAMK, CMGC, CK1, and STE. The 90 tyrosine kinases fall into two families: the TK (tyrosine kinase) family of 58 kinases and the TKL (tyrosine kinase-like) family of 32 kinases. There are 40 atypical kinases that are highly structurally distinct from the remainder. The TK family is a source for validated drug targets, such as epidermal growth factor receptor (EGFR), vascular endothelial growth factor receptor (VEGFR), and platelet-derived growth factor receptor (PDGFR). Recent clinical data provided proof-of-concept for selective B-Raf inhibitors in the treatment of B-Raf$^{V600E}$ mutant melanoma, which led to the approved clinical use of vemurafenib for the treatment of late stage metastatic melanoma.

The regulation of cancer cell growth is often modulated by multiple kinases acting both in independent pathways and in concerted signaling cascades. Thus, the Ras/Raf/MEK/ERK mitogen-activated protein kinase (MAPK) pathway mediates cellular responses to different growth signals and is frequently deregulated in cancer. The Raf family consist of serine/threonine kinases A-Raf, B-Raf and C-Raf (Raf-1), which phosphorylate and activate MEK. Only B-Raf is frequently mutated in various cancers; and the most common B-Raf mutation involves a substitution of a glutamic acid residue to a valine moiety at codon 600 (BRAF$^{V600E}$). Mutations in the B-Raf gene may lead to MAPK pathway amplification via constitutive activation of B-Raf kinase, even in the absence of any growth signals, resulting in increased malignancy.

A landmark study published in 2002 identified activating mutations in the B-Raf serine/threonine kinase gene BRAF in more than 50% of all melanomas. In addition to melanoma, activating BRAF mutations have also been identified in colorectal carcinomas (where it occurs in 40% of tumors with mismatch repair deficiency), 50% of thyroid papillary carcinomas and 30% of low-grade serous ovarian carcinomas. Although related isoforms of Raf, such as A-Raf and C-Raf, can activate other signaling pathways, it is believed that the transforming activity of B-Raf arises mainly through the stimulation of the MAPK pathway.

Melanomas are tumors derived from the transformation of melanocytes, a family of specialized pigment-producing cells. Melanomas are broadly divided into those arising from the skin (cutaneous), eyes (uveal) or mucous membranes (mucosal). Although melanoma is only the third most common form of skin cancer in people of European descent (after squamous cell carcinoma and basal cell carcinoma), it accounts for nearly all skin cancer deaths. Once disseminated to distant organs, melanoma becomes a considerable clinical problem associated with high rates of morbidity and mortality. Currently, median survival for stage IV melanoma is between 6 and 10 months, a rate that has changed little over the last 30 years.

Vemurafenib (ZELBORAF®; also known as PLX4032) is a small-molecule B-Raf kinase inhibitor for the treatment of cancers harboring activating BRAF mutations. The primary focus of vemurafenib use is in melanoma (>50% harbor activating BRAF mutations). The applications of vemurafenib with other solid tumors, such as colorectal carcinoma (>10% harbor BRAF mutations), are also under investigation. Purified kinase assays have demonstrated that vemurafenib and its related analogs are highly potent inhibitors of B-Raf activity, with 3-fold selectivity for the V600E mutation over the wild-type kinase.

In preclinical models, vemurafenib and its analogs inhibited the growth of B-Raf$^{V600E}$ positive melanoma cell lines both in vitro and in vivo. In the initial stage of phase I clinical study, cohorts of patients with advanced solid tumors were treated with escalating doses of vemurafenib (ranging from 200 to 1,600 mg), administered twice-daily (BID) as oral capsules. The crystalline formulation yielded only modest drug exposures, so vemurafenib had to be reformulated as a micro-precipitated bulk powder (MBP), which can increase drug bioavailability.

Vemurafenib have low solubility in water and consequently showed a low dissolution rate and as a result exhibited poor bioavailability, especially when administered orally in crystalline form. Poor bioavailability can cause unpredictable absorption of the compound by the patient, leading to unpredictability in dose/therapy effects. Often food may affect the ability of the patient to absorb such poorly bioavailable compounds, and requiring dosing regimens to be adjusted accordingly. Also, an erratic absorbed drug commands a large safety margin. Moreover, such a drug will require higher doses to achieve sufficiently high systemic or target concentrations for efficacy, which may not be practical in some cases or may lead to adverse effects in others (Testa et al., Prodrugs: bridging pharmacodynamic/pharmacokinetic gaps. *Curr. Opin. Chem. Biol.* 2009, 13, 1-7).

Prodrugs are analogues of active pharmaceutical ingredient that following administration are converted or metabolized to an active form of the drug in vivo. Prodrugs are used to modify one or more aspects of the pharmacokinetics of a drug in a manner that enhances the therapeutic efficacy of a drug. Prodrugs can provide possibilities to overcome various barriers to drug formulation and delivery such as poor aqueous solubility, chemical instability, insufficient oral absorption, rapid pre-systemic metabolism, and toxicity.

Clearly, a significant problem with oral administration of vemurafenib is the bioavailability at larger doses, which are required for the therapeutic efficacy of vemurafenib (approved daily dose is 960 mg BID in MBP formulation). The superior efficacy of vemurafenib against melanoma makes vemurafenib a particular compelling candidate for the preparation of its analogues that can be easily formulated to provide better oral bioavailability. Thus, there is a need for prodrugs of vemurafenib with demonstrated enhanced oral bioavailability. In particular, masking nitrogen in azaindole NH moiety and/or in aryl sulfonamide NH in vemurafenib facilitated absorption throughout gastrointestinal tract. These vemurafenib analogues can enhance the convenience (by reducing the dose and dosing frequency), efficacy, and lessen side effect profile of vemurafenib. In addition, vemurafenib analogues may also be able to be formulated in solution form for intravenous administration or in extensive release forms.

SUMMARY OF THE INVENTION

These and other needs are satisfied by the disclosure herein of substituted azaindole prodrugs, methods of making said prodrugs, pharmaceutical compositions of said prodrugs and methods of using said prodrugs and pharmaceutical compositions thereof to treat or prevent diseases or disorders such as cancer.

Specifically, it has been found that compounds disclosed herein, and pharmaceutically acceptable compositions thereof, are effective as prodrugs of vemurafenib for treating or preventing diseases or disorders such as cancer.

The first aspect of the invention provides a compound of Formula (I):

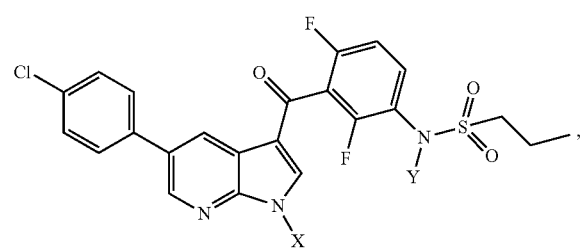

(I)

or a racemic mixture, a stereoisomer, a geometric isomer, a tautomer, a solvate, an N-oxide, a metabolite, or a pharmaceutically acceptable salt thereof, wherein each of X and Y is as defined herein.

In some embodiments, each of X and Y is independently H, —C(=O)$R^3$, —C(=O)O$R^4$, —C($R^1R^2$)OC(=O)$R^3$, —C($R^1R^2$)OC(=O)O$R^4$ or —C($R^1R^2$)OP(=O)(O$R^4$)(O$R^{4a}$), with the proviso that when Y is H, X is not —C(=O)CH$_3$ or H;

each $R^1$ and $R^2$ is independently H, D, $C_{1-6}$alkyl, $C_{1-6}$haloalkyl, $C_{3-6}$cycloalkyl, —($C_{1-4}$ alkylene)—($C_{3-6}$cycloalkyl), $C_{3-6}$heterocyclyl or —($C_{1-4}$alkylene)-($C_{3-6}$heterocyclyl); or $R^1$ and $R^2$, together with the carbon atom they are attached to, form an unsubstituted or substituted 3-8 membered carbocyclic or heterocyclic ring;

each $R^3$ is independently H, D, $C_{1-10}$alkyl, $C_{1-10}$haloalkyl, $C_{3-8}$cycloalkyl, —($C_{1-6}$alkylene)-($C_{3-8}$cycloalkyl), $C_{3-8}$heterocyclyl, —($C_{1-6}$alkylene)-($C_{3-8}$heterocyclyl), $C_{6-10}$aryl, —($C_{1-6}$alkylene)-($C_{1-6}$aryl), 5-10 membered heteroaryl or —($C_{1-6}$alkylene)-(5-10 membered heteroaryl), wherein each of the $C_{1-10}$alkyl, $C_{1-10}$haloalkyl, $C_{3-8}$cycloalkyl, —($C_{1-6}$alkylene)-($C_{3-8}$cycloalkyl), $C_{3-8}$heterocyclyl, —($C_{1-6}$alkylene)-($C_{3-8}$heterocyclyl), $C_{6-10}$aryl, —($C_{1-6}$alkylene)-($C_{6-10}$ aryl), 5-10 membered heteroaryl and —($C_{1-6}$alkylene)-(5-10 membered heteroaryl) is unsubstituted or optionally substituted with 1, 2, 3 or 4 substituents independently selected from D, F, Cl, Br, I, $C_{1-6}$alkyl, $C_{1-6}$haloalkyl, —OH, —NH$_2$, $C_{1-6}$alkoxy and $C_{1-6}$alkylamino; and each $R^4$ and $R^{4a}$ is independently H, $C_{1-10}$alkyl, $C_{1-10}$haloalkyl, $C_{3-8}$cycloalkyl, —($C_{1-6}$alkylene)-($C_{3-8}$cycloalkyl), $C_{3-8}$heterocyclyl, —($C_{1-6}$alkylene)-($C_{3-8}$heterocyclyl), $C_{6-10}$aryl, —($C_{1-6}$alkylene)-($C_{6-10}$aryl), 5-10 membered heteroaryl or —($C_{1-6}$alkylene)-(5-10 membered heteroaryl), wherein each of the $C_{1-10}$alkyl, $C_{1-10}$haloalkyl, $C_{3-8}$cycloalkyl, —($C_{1-6}$alkylene)-($C_{3-8}$cycloalkyl), $C_{3-8}$heterocyclyl, —($C_{1-6}$alkylene)-($C_{3-8}$heterocyclyl), $C_{6-10}$aryl, —($C_{1-6}$alkylene)-($C_{6-10}$aryl), 5-10 membered heteroaryl and —($C_{1-6}$alkylene)-(5-10 membered heteroaryl) is unsubstituted or optionally substituted with 1, 2, 3 or 4 substituents independently selected from D, F, Cl, OH, NH$_2$, oxo (=O), $C_{1-6}$alkyl, $C_{1-6}$haloalkyl, $C_{1-6}$alkoxy and $C_{1-6}$alkylamino.

In other embodiments, each $R^1$ and $R^2$ is independently H, D or $C_{1-3}$alkyl.

In other embodiments, each $R^3$ is independently $C_{1-10}$alkyl, $C_{3-8}$cycloalkyl, —($C_{1-6}$alkylene)-($C_{3-8}$cycloalkyl), $C_{3-8}$heterocyclyl, —($C_{1-6}$alkylene)-($C_{3-8}$heterocyclyl), $C_{6-10}$ aryl, —($C_{1-6}$alkylene)-($C_{6-10}$aryl), 5-10 membered heteroaryl or —($C_{1-6}$alkylene)-(5-10 membered heteroaryl), wherein each of the $C_{1-10}$alkyl, $C_{3-8}$cycloalkyl, —($C_{1-6}$alkylene)-($C_{3-8}$-cycloalkyl), $C_{3-8}$heterocyclyl, —($C_{1-6}$alkylene)-($C_{3-8}$heterocyclyl), $C_{6-10}$aryl, —($C_{1-6}$alkylene)-($C_{6-10}$aryl), 5-10 membered heteroaryl and —($C_{1-6}$alkylene)-(5-10 membered heteroaryl) is unsubstituted or optionally substituted with 1, 2, 3 or 4 substituents independently selected from D, F, —OH, —OMe, —NH$_2$, —NHMe, —NMe$_2$ and $C_{1-3}$alkyl.

In other embodiments, each $R^4$ and $R^{4a}$ is independently H, $C_{1-10}$alkyl, $C_{3-8}$cycloalkyl, —($C_{1-6}$alkylene)-($C_{3-8}$cycloalkyl), $C_{3-8}$heterocyclyl, —($C_{1-6}$alkylene)-($C_{3-8}$heterocyclyl) or $C_{6-10}$aryl, wherein each of the $C_{1-10}$alkyl, $C_{3-8}$cycloalkyl, —($C_{1-6}$alkylene)-($C_{3-8}$cycloalkyl), $C_{3-8}$heterocyclyl, —($C_{1-6}$alkylene)-($C_{3-8}$heterocyclyl) and $C_{6-10}$aryl is unsubstituted or optionally substituted with 1, 2, 3 or 4 substituents independently selected from D, F, OH, OMe, oxo (=O), NH$_2$, —NHMe, —NMe$_2$ and $C_{1-3}$alkyl.

In other embodiments, each of X and Y is independently H or —C($R^1R^2$)OP(=O)(OH)$_2$, with the proviso that when Y is H, X is not H.

In other embodiment, each of X and Y is independently H, —C(=O)$R^3$, —C(=O)O$R^4$, —C($R^1R^2$)OC(=O)$R^3$ or —C($R^1R^2$)OC(=O)O$R^4$, with the proviso that when Y is H, X is not —C(=O)CH$_3$ or H.

In other embodiments, the acyl moiety (—C(=O)$R^3$) is derived from an α-amino acid or an optical isomer thereof by removing the OH group from the carboxy group of the α-amino acid.

In other embodiments, the α-amino acid is isoleucine, leucine, lysine, methionine, phenylalanine, threonine, tryptophan, valine, alanine, asparagine, aspartate, glutamate, glutamine, proline, serine, para-tyrosine, arginine, histidine, cysteine, glycine, sarcosine, N,N-dimethyl glycine, homoserine, norvaline, norleucine, ornithine, homocysteine, homophenylalanine, phenylglycine, ortho-tyrosine, meta-tyrosine or hydroxyproline.

In other embodiments, the α-amino acid is isoleucine, leucine, lysine, methionine, phenylalanine, threonine, tryptophan, valine, alanine, asparagine, aspartate, glutamate, glutamine, proline, serine, tyrosine, arginineor histidine, each of which has a S-configuration at the α-position.

In other embodiments, the pharmaceutically acceptable salt is an alkali metal salt, an alkaline earth metal salt, or an ammonium or $N^+(C_{1-4}$ alkyl$)_4$ salt.

In other embodiments, the pharmaceutically acceptable salt is a sodium salt, a lithium salt, a potassium salt, a calcium salt, a magnesium salt; an ammonium salt, a quaternary ammonium salt or a combination thereof.

In other embodiments, the pharmaceutically acceptable salt is a salt of an inorganic acid, an organic acid or a combination thereof, wherein the inorganic acid or the organic acid is hydrochloric acid, hydrobromic acid, sulfuric acid, nitric acid, phosphoric acid, acetic acid, maleic acid, succinic acid, mandelic acid, fumaric acid, malonic acid, malic acid, 2-hydroxypropanic acid, pyruvic acid, oxalic acid, glycolic acid, salicylic acid, glucuronic acid, galacturonic acid, citric acid, tartaric acid, aspartic acid, glutamic acid, benzoic acid, cinnamic acid, p-toluenesulfonic acid, benzenesulfonic acid, mthanesulfonic acid, ethanesulfonic acid, trifluoromthanesulfonic acid or a combination thereof.

In another aspect, provided herein is a pharmaceutical composition comprising a compound disclosed herein, and a pharmaceutically acceptable carrier, excipient, diluent, adjuvant, vehicle or a combination thereof. In some embodiments, the compound is a prodrug of vemurafenib, a B-Raf kinase inhibitor.

In another aspect, provided herein is a composition comprising a compound that undergoes metabolic transformations in vivo to provide metabolites that are inhibitors of protein kinase. In some embodiments, the metabolite is vemurafenib, a B-Raf kinase inhibitor.

In some embodiments, the pharmaceutical composition disclosed herein further comprises a therapeutic agent selected from the group consisting of chemotherapeutic agents, anti-proliferative agents, agents for treating atherosclerosis, agents for treating lung fibrosis and combinations thereof.

In other embodiments, the therapeutic agent is chlorambucil, melphalan, cyclophosphamide, ifosfamide, busulfan, carmustine, lomustine, streptozocin, cisplatin, carboplatin, oxaliplatin, dacarbazine, temozolomide, procarbazine, methotrexate, fluorouracil, cytarabine, gemcitabine, mercaptopurine, fludarabine, vinblastine, vincristine, vinorelbine, paclitaxel, docetaxel, topotecan, irinotecan, etoposide, trabectedin, dactinomycin, doxorubicin, epirubicin, daunorubicin, mitoxantrone, bleomycin, mitomycin, ixabepilone, tamoxifen, flutamide, gonadorelin analogues, megestrol, prednisone, dexamethasone, methylprednisolone, thalidomide, interferon alfa, leucovorin, sirolimus, temsirolimus, everolimus, afatinib, alisertib, amuvatinib, apatinib, axitinib, bortezomib, bosutinib, brivanib, cabozantinib, cediranib, crenolanib, crizotinib, dabrafenib, dacomitinib, danusertib, dasatinib, dovitinib, erlotinib, foretinib, ganetespib, gefitinib, ibrutinib, icotinib, imatinib, iniparib, lapatinib, lenvatinib, linifanib, linsitinib, masitinib, momelotinib, motesanib, neratinib, nilotinib, niraparib, oprozomib, olaparib, pazopanib, pictilisib, ponatinib, quizartinib, regorafenib, rigosertib, rucaparib, ruxolitinib, saracatinib, saridegib, sorafenib, sunitinib, tasocitinib, telatinib, tivantinib, tivozanib, tofacitinib, trametinib, vandetanib, veliparib, vemurafenib, vismodegib, volasertib, alemtuzumab, bevacizumab, brentuximabvedotin, catumaxomab, cetuximab, denosumab, gemtuzumab, ipilimumab, nimotuzumab, ofatumumab, panitumumab, ramucirumab, rituximab, tositumomab, trastuzumab, or a combination thereof.

In another aspect, provided herein is a method of preventing, managing, treating or lessening the severity of a proliferative disorder in a patient by administering to the patient with the compound disclosed herein, or the pharmaceutical composition disclosed. In other embodiments, the method further comprises administering a therapeutic agent to the patient.

In another aspect, provided herein is the compound disclosed herein or the pharmaceutical composition disclosed herein for use in preventing, managing, treating or lessening the severity of a proliferative disorder in a patient.

In some embodiments, the proliferative disorder is metastatic cancer. In other embodiments, the proliferative disorder is colon cancer, gastric adenocarcinoma, bladder cancer, breast cancer, kidney cancer, liver cancer, lung cancer, melanoma, thyroid cancer, a cancer of the head and neck, prostate cancer, pancreatic cancer, a cancer of the CNS, glioblastoma, or a myeloproliferative disorder. In further embodiments, the proliferative disorder is atherosclerosis or lung fibrosis.

In another aspect, provided herein is a method of inhibiting or modulating the activity of a protein kinase in a biological sample comprising contacting a biological sample with the compound disclosed herein, or the pharmaceutical composition disclosed herein. In some embodiments, the protein kinase is B-Raf.

In another aspect, provided herein is a method of inhibiting protein tyrosine kinase, the method comprises contacting the kinase with the compound disclosed herein, or with the composition disclosed herein. In some embodiments, provided herein is a method of inhibiting B-Raf kinase signaling, the method comprises contacting the receptor with the compound disclosed herein, or with the pharmaceutical composition disclosed herein.

In other embodiments, inhibition of the activity of a receptor protein kinase, such as B-Raf signaling, can be in a cell or a multicellular organism. If in a multicellular organism, the method disclosed herein may comprise administering to the organism the compound disclosed herein, or the pharmaceutical composition disclosed herein. In some embodiments, the organism is a mammal; in other embodiments, the organism is a human. In still other embodiments, the method further comprises contacting the kinase with a therapeutic agent.

In another aspect, provided herein is a method of inhibiting proliferative activity of a cell, wherein the method comprises contacting the cell with an effective proliferative inhibiting amount of the compound disclosed herein or the pharmaceutical composition disclosed herein. In some embodiments, the method further comprises contacting the cell with an additional therapeutic agent.

In another aspect, provided herein is a method of treating a cell proliferative disease in a patient, wherein the method comprises administering to the patient in need of such treatment an effective therapeutic amount of the compound disclosed herein or the pharmaceutical composition disclose herein. In some embodiments, the method further comprises administering an additional therapeutic agent.

In another aspect, provided herein is a method of inhibiting tumor growth in a patient, the method comprises administering to the patient in need thereof treatment an effective therapeutic amount of the compound disclosed herein or the pharmaceutical composition disclose herein. In some embodiments, the method further comprises administering an additional therapeutic agent.

In another aspect, provided herein includes methods of preparing, methods of separating, and methods of purifying compounds of Formula (I).

The foregoing merely summarizes certain aspects disclosed herein and is not intended to be limiting in nature. These aspects and other aspects and embodiments are described more fully below.

DETAILED DESCRIPTION OF THE INVENTION

Definitions and General Terminology

Reference will now be made in detail to certain embodiments of the invention, examples of which are illustrated in the accompanying structures and formulas. The invention is intended to cover all alternatives, modifications, and equivalents which may be included within the scope of the present invention as defined by the claims. One skilled in the art will recognize many methods and materials similar or equivalent to those described herein, which could be used in the practice of the present invention. The present invention is in no way limited to the methods and materials described herein. In the event that one or more of the incorporated literature, patents, and similar materials differs from or contradicts this application, including but not limited to defined terms, term usage, described techniques, or the like, this application controls.

As used herein, the following definitions shall apply unless otherwise indicated. For purposes of this invention, the chemical elements are identified in accordance with the Periodic Table of the Elements, CAS version, and the Handbook of Chemistry and Physics, 75$^{th}$ Ed. 1994. Additionally, general principles of organic chemistry are described in Sorrell et al., "Organic Chemistry", University Science Books, Sausalito: 1999, and Smith et al., "March's Advanced Organic Chemistry", John Wiley & Sons, New York: 2007, all of which are incorporated herein by reference.

As described herein, compounds disclosed herein may optionally be substituted with one or more substituents, such as those are illustrated below, or as exemplified by particular classes, subclasses, and species of the invention. It will be appreciated that the phrase "optionally substituted" is used interchangeably with the phrase "substituted". In general, the term "substituted" refers to the replacement of one or more hydrogen radicals in a given structure with the radical of a specified substituent. Unless otherwise indicated, an optionally substituted group may have a substituent at each substitutable position of the group. When more than one position in a given structure can be substituted with more than one substituent selected from a specified group, the substituent may be either the same or different at each position. Examples of substituent include, but are not limited to, D, F, Cl, Br, I, oxo (=O), alkyl, haloalkyl, OH, NH$_2$, alkoxy and alkylamino.

The term "alkyl" or "alkyl group" refers to a saturated linear or branched-chain monovalent hydrocarbon radical of one to twenty carbon atoms, wherein the alkyl radical may be optionally substituted independently with one or more substituents described below. Unless otherwise specified, alkyl groups contain 1-20 carbon atoms. In some embodiments, alkyl groups contain 1-10 carbon atoms. In another embodiment, alkyl groups contain 1-8 carbon atoms. In some embodiments, alkyl groups contain 1-6 carbon atoms. In another embodiment, alkyl groups contain 1-4 carbon atoms. In still some embodiments, alkyl groups contain 1-3 carbon atoms and in yet other embodiments, alkyl groups contain 1-2 carbon atoms.

Some non-limiting examples of alkyl groups include methyl (Me, —CH$_3$), ethyl (Et, —CH$_2$CH$_3$), 1-propyl (n-Pr, n-propyl, —CH$_2$CH$_2$CH$_3$), 2-propyl (i-Pr, i-propyl, —CH(CH$_3$)$_2$), 1-butyl (n-Bu, n-butyl, —CH$_2$CH$_2$CH$_2$CH$_3$), 2-methyl-1-propyl (i-Bu, i-butyl, —CH$_2$CH(CH$_3$)$_2$), 2-butyl (s-Bu, s-butyl, —CH(CH$_3$)CH$_2$CH$_3$), 2-methyl-2-propyl (t-Bu, t-butyl, —C(CH$_3$)$_3$), 1-pentyl (n-pentyl, —CH$_2$CH$_2$CH$_2$CH$_2$CH$_3$), 2-pentyl (—CH(CH$_3$)CH$_2$CH$_2$CH$_3$), 3-pentyl (—CH(CH$_2$CH$_3$)$_2$), 2-methyl-2-butyl (—C(CH$_3$)$_2$CH$_2$CH$_3$), 3-methyl-2-butyl (—CH(CH$_3$)CH(CH$_3$)$_2$), 3-methyl-1-butyl (—CH$_2$CH$_2$CH(CH$_3$)$_2$), 2-methyl-1-butyl (—CH$_2$CH(CH$_3$)CH$_2$CH$_3$), 1-hexyl (—CH$_2$CH$_2$CH$_2$CH$_2$CH$_2$CH$_3$), 2-hexyl (—CH(CH$_3$)CH$_2$CH$_2$CH$_2$CH$_3$), 3-hexyl (—CH(CH$_2$CH$_3$)(CH$_2$CH$_2$CH$_3$)), 2-methyl-2-pentyl (—C(CH$_3$)$_2$CH$_2$CH$_2$CH$_3$), 3-methyl-2-pentyl (—CH(CH$_3$)CH(CH$_3$)CH$_2$CH$_3$), 4-methyl-2-pentyl (—CH(CH$_3$)CH$_2$CH(CH$_3$)$_2$), 3-methyl-3-pentyl (—C(CH$_3$)(CH$_2$CH$_3$)$_2$), 2-methyl-3-pentyl (—CH(CH$_2$CH$_3$)CH(CH$_3$)$_2$), 2,3-dimethyl-2-butyl (—C(CH$_3$)$_2$CH(CH$_3$)$_2$), 3,3-dimethyl-2-butyl (—CH(CH$_3$)C(CH$_3$)$_3$, 1-heptyl, 1-octyl, and the like.

The terms "alkyl" and the prefix "alk-" are inclusive of both straight chain and branched saturated carbon chain.

The term "alkylene" refers to a saturated divalent hydrocarbon group derived from a straight or branched chain saturated hydrocarbon by the removal of two hydrogen atoms, wherein the alkyl radical may be optionally substituted independently with one or more substituents described herein. Some non-limiting examples include methylene (—CH$_2$—), ethylidene (—CH(CH$_3$)—), ethylene (—CH$_2$CH$_2$—), isopropylene (—CH(CH$_3$)CH$_2$—), and the like.

The term "alkenyl" refers to linear or branched-chain monovalent hydrocarbon radical of two to twelve carbon atoms with at least one site of unsaturation, i.e., a carbon-carbon, sp$^2$ double bond, wherein the alkenyl radical may be optionally substituted independently with one or more substituents described herein, and includes radicals having "cis" and "trans" orientations, or alternatively, "E" and "Z" orientations. Some non-limiting examples include ethylenyl or vinyl (—CH=CH$_2$), allyl (—CH$_2$CH=CH$_2$), and the like.

The term "alkynyl" refers to linear or branched-chain monovalent hydrocarbon radical of two to twelve carbon atoms with at least one site of unsaturation, i.e., a carbon-carbon, sp triple bond, wherein the alkynyl radical may be unsubstituted or optionally substituted independently with one or more substituents described herein. Some non-limiting examples include ethynyl (—C≡CH), propynyl (propargyl, —CH$_2$C≡CH), —C≡C—CH$_3$, and the like.

The terms "haloalkyl", "haloalkenyl" or "haloalkoxy" refers to alkyl, alkenyl, or alkoxy, as the case may be, substituted with one or more halogen atoms. Some non-limiting examples include —CF$_3$, —OCF$_3$, and the like.

The term "carbocycle", "carbocyclyl", "carbocyclic", "carbocyclic ring" or "cycloaliphatic" refers to a monovalent or multivalent non-aromatic, saturated or partially unsaturated ring having 3 to 12 carbon atoms as a monocyclic ring system. Some non-limiting examples of suitable cycloaliphatic groups include cycloalkyl, cycloalkenyl, and cycloalkynyl. Further examples of cycloaliphatic groups include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, cyclohexadienyl, and the like. The term "cycloalkyl" refers to a monovalent or multivalent saturated ring having 3 to 12 carbon atoms as a monocyclic ring system. The cycloalkyl groups herein are unsubstituted or optionally substituted independently with one or more substituents described herein.

The term "heterocycle", "heterocyclyl", "heterocyclic" or "heterocyclic ring" as used interchangeably herein refers to a monocyclic ring system in which one or more ring members are an independently selected heteroatom and that is completely saturated or that contains one or more units of unsaturation, but not aromatic having a single point of attachment to the rest of the molecule. One or more ring atoms are optionally substituted independently with one or more substituents described herein. In some embodiments, the "heterocycle", "heterocyclyl", "heterocyclic" or "heterocyclic ring" group is a monocycle having 3 to 7 ring members (2 to 6 carbon atoms and 1 to 3 heteroatoms selected from N, O, P, and S, wherein S or P is optionally substituted with one or more oxo to provide the group SO or $SO_2$, PO or $PO_2$ or a bicycle having 7 to 10 ring members (4 to 9 carbon atoms and 1 to 3 heteroatoms selected from N, O, P, and S, wherein the S or P is optionally substituted with one or more oxo to provide the group SO or $SO_2$, PO or $PO_2$.

The heterocyclyl may be a carbon radical or heteroatom radical. Some non-limiting examples of heterocyclic rings include pyrrolidinyl, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, homo-piperazinyl, azetidinyl, oxetanyl, thietanyl, homopiperidinyl, oxepanyl, thiepanyl, oxazepinyl, diazepinyl, thiazepinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinylimidazolinyl, imidazolidinyl, 1,2,3,4-tetrahydroiso-quinolinyl, 5-methyl-1,3-dioxol-4-yl. Examples of a heterocyclic group wherein 2 ring carbon atoms are substituted with oxo ($=$O) moieties are pyrimidindionyl and 1,1-dioxo-thiomorpholinyl. The heterocycle groups herein are unsubstituted or optionally substituted independently with one or more substituents described herein.

The term "heteroatom" refers to one or more of oxygen, sulfur, nitrogen, phosphorus, or silicon, including any oxidized forms of nitrogen, sulfur, or phosphorus; the quaternized form of any basic nitrogen; or a substitutable nitrogen of a heterocyclic ring, for example N (as in 3,4-dihydro-2H-pyrrolyl), NH (as in pyrrolidinyl) or NR (as in N—substituted pyrrolidinyl).

The term "halogen" refers to F, Cl, Br, or I.

The term "H" refers to a single hydrogen atom. This radical may be attached, for example, to an oxygen atom to form a hydroxyl radical.

The term "D" or "$^2$H" refers to a single deuterium atom. One of this radical may be attached, for example, to a methyl group to form a mono-deuterated methyl group (—$CDH_2$), two of deuterium atoms may be attached to a methyl group to form a di-deuterated methyl (—$CD_2H$), and three of deuterium atoms may be attached to a methyl group to form a tri-deuterated methyl group (—$CD_3$).

The term "aryl" used alone or as part of a larger moiety as in "aryloxyalkyl" refers to monocyclic, bicyclic, and tricyclic carbocyclic ring systems having a total of six to fourteen ring members, wherein at least one ring in the system is aromatic, wherein each ring in the system contains 3 to 7 ring members and that has a single point of attachment to the rest of the molecule. The term "aryl" may be used interchangeably with the term "aryl ring". Examples of aryl rings would include phenyl, naphthyl and anthracene.

The term "heteroaryl" used alone or as part of a larger moiety as in "heteroaralkyl" refers to monocyclic, bicyclic, and tricyclic ring systems having a total of five to fourteen ring members, wherein at least one ring in the system is aromatic, at least one ring in the system contains one or more heteroatoms, wherein each ring in the system contains 5 to 7 ring members and that has a single point of attachment to the rest of the molecule. The term "heteroaryl" may be used interchangeably with the term "heteroaryl ring" or the term "heteroaromatic". The heteroaryl groups herein are unsubstituted or optionally substituted independently with one or more substituents described herein.

Some non-limiting examples of heteroaryl rings include the following monocycles: 2-furanyl, 3-furanyl, N-imidazolyl, 2-imidazolyl, 4-imidazolyl, 5-imidazolyl, 3-isoxazolyl, 4-isoxazolyl, 5-isoxazolyl, 2-oxazolyl, 4-oxazolyl, 5-oxazolyl, N-pyrrolyl, 2-pyrrolyl, 3-pyrrolyl, 2-pyridyl, 3-pyridyl, 4-pyridyl, 2-pyrimidinyl, 4-pyrimidinyl, 5-pyrimidinyl, pyridazinyl (e.g., 3-pyridazinyl), 2-thiazolyl, 4-thiazolyl, 5-thiazolyl, tetrazolyl (e.g., 5-tetrazolyl), triazolyl (e.g., 2-triazolyl and 5-triazolyl), 2-thienyl, 3-thienyl, pyrazolyl (e.g., 2-pyrazolyl), isothiazolyl, 1,2,3-oxadiazolyl, 1,2,5-oxadiazolyl, 1,2,4-oxadiazolyl, 1,2,3-triazolyl, 1,2,3-thiadiazolyl, 1,3,4-thiadiazolyl, 1,2,5-thiadiazolyl, pyrazinyl, 1,3,5-triazinyl, and the following bicycles: benzimidazolyl, benzofuryl, benzothiophenyl, indolyl (e.g., 2-indolyl), purinyl, quinolinyl (e.g., 2-quinolinyl, 3-quinolinyl, 4-quinolinyl), and isoquinolinyl (e.g., 1-isoquinolinyl, 3-isoquinolinyl or 4-isoquinolinyl).

The term "carboxy" or "carboxyl", whether used alone or with other terms, such as "carboxyalkyl", refers to —$CO_2H$. The term "carbonyl", whether used alone or with other terms, such as "aminocarbonyl", refers to —(C$=$O)—. The term "acyl" refers to —(C$=$O)R, wherein R refers to alkyl.

The term "alkoxy" refers to an alkyl group, as previously defined, attached to the principal carbon chain through an oxygen ("alkoxy") atom. Unless otherwise specified, alkoxy groups contain 1-20 carbon atoms. In some embodiments, alkoxy groups contain 1-8 carbon atoms. In other embodiments, alkoxy groups contain 1-6 carbon atoms. In still other embodiments, alkoxy groups contain 1-4 carbon atoms, and in yet other embodiments, alkoxy groups contain 1-3 carbon atoms.

Some non-limiting examples of alkoxy groups include methoxy (MeO, —$OCH_3$), ethoxy (EtO, —$OCH_2CH_3$), 1-propoxy (n-PrO, n-propoxy, —$OCH_2CH_2CH_3$), 2-propoxy (i-PrO, i-propoxy, —$OCH(CH_3)_2$), 1-butoxy (n-BuO, n-butoxy, —$OCH_2CH_2CH_2CH_3$), 2-methyl-1-propoxy (i-BuO, i-butoxy, —$OCH_2CH(CH_3)_2$), 2-butoxy (s-BuO, s-butoxy, —$OCH(CH_3)CH_2CH_3$), 2-methyl-2-propoxy (t-BuO, t-butoxy, —$OC(CH_3)_3$), 1-pentoxy(n-pentoxy, —$OCH_2CH_2CH_2CH_2CH_3$), 2-pentoxy (—$OCH(CH_3)CH_2CH_2CH_3$), 3-pentoxy (—$OCH(CH_2CH_3)_2$), 2-methyl-2-butoxy (—$OC(CH_3)_2CH_2CH_3$), 3-methyl-2-butoxy (—$OCH(CH_3)CH(CH_3)_2$), 3-methyl-1-butoxy (—$OCH_2CH_2CH(CH_3)_2$), 2-methyl-1-butoxy (—$OCH_2CH(CH_3)CH_2CH_3$), and the like.

The term "alkylamino" embraces "N-alkylamino" and "N,N-dialkylamino" where amino groups are independently substituted with one alkyl radical and with two alkyl radicals, respectively. More preferred alkylamino radicals are "lower alkylamino" radicals having one or two alkyl radicals of one to six carbon atoms, attached to a nitrogen atom. Suitable alkylamino radicals may be mono or dialkylamino such as N-methylamino, N-ethylamino, N,N-dimethylamino, N,N-diethylamino, and the like.

The term "unsaturated" as used herein, refers to that a moiety has one or more units of unsaturation.

The term "comprising" is meant to be open ended, including the indicated component but not excluding other elements.

As described herein, a bond drawn from a substituent to the center of one ring within a ring system (as shown below) represents substitution of the substituent at any substitutable position on the rings to which it is attached. For example, Structure a represents possible substitution in any of the positions on the B ring shown in Structure b.

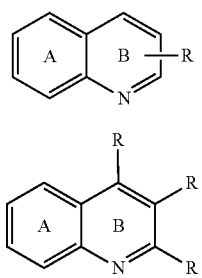

Structure a

Structure b

Unless otherwise stated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the invention.

The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

Unless otherwise stated, all tautomeric forms of the compounds of the invention are within the scope of the invention. Additionally, unless otherwise stated, structures depicted herein are also meant to include compounds that differ only in the presence of one or more isotopically enriched atoms.

The term "prodrug" refers to a compound that is transformed in vivo into a compound of formula (I). Such a transformation can be affected, for example, by hydrolysis in blood or enzymatic transformation of the prodrug form to the parent form in blood or tissue. Prodrugs of the compounds of the invention may be, for example, esters. Esters that may be utilized as prodrugs in the present invention are phenyl esters, aliphatic $C_{1-24}$ esters, acyloxymethyl esters, carbonates, carbamates, and amino acid esters. For example, a compound of the invention that contains an OH group may be acylated at this position in its prodrug form. Other prodrug forms include phosphates, such as, for example those phosphates resulting from the phosphonation of an OH group on the parent compound. A thorough discussion of prodrugs is provided in Higuchi et al., Pro-drugs as Novel Delivery Systems, Vol. 14, A.C.S. Symposium Series; Roche et al., ed., Bioreversible Carriers in Drug Design, American Pharmaceutical Association and Pergamon Press, 1987; Rautio et al., Prodrugs: Design and Clinical Applications, *Nature Reviews Drug Discovery*, 2008, 7, 255-270, and Hecker et al, Prodrugs of Phosphates and Phosphonates, *J. Med. Chem.*, 2008, 51, 2328-2345, all of which are incorporated herein by reference.

A "metabolite" is a product produced through metabolism in the body of a specified compound or salt thereof. Metabolites of a compound may be identified using routine techniques known in the art and their activities determined using tests such as those described herein. Such products may result for example from the oxidation, reduction, hydrolysis, amidation, deamidation, esterification, deesterification, enzymatic cleavage, and the like, of the administered compound.

Stereochemical definitions and conventions used herein generally follow Parker et al., ed., McGraw-Hill Dictionary of Chemical Terms (1984) McGraw-Hill Book Company, New York and Eliel et al., "Stereochemistry of Organic Compounds", John Wiley & Sons, Inc., New York, 1994. The compounds of the invention may contain asymmetric or chiral centers, and therefore exist in different stereoisomeric forms. It is intended that all stereoisomeric forms of the compounds of the invention, including but not limited to, diastereomers, enantiomers and atropisomers, as well as mixtures thereof such as racemic mixtures, form part of the present invention. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes D and L or (+) and (−) are employed to designate the sign of rotation of plane-polarized light by the compound, with (−) or L meaning that the compound is levorotatory. A compound prefixed with (+) or D is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process.

The term "racemic mixture" or "racemate" refers to an equimolar mixture of two enantiomeric species, devoid of optical activity.

A "pharmaceutically acceptable salt" refers to organic or inorganic salts of a compound of the invention. Pharmaceutically acceptable salts are well known in the art. For example, Berge et al., describe pharmaceutically acceptable salts in detail in *J. Pharmacol Sci*, 1977, 66, 1-19, which is incorporated herein by reference. Some non-limiting examples of pharmaceutically acceptable, nontoxic salts include salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. The pharmaceutically acceptable salt is an alkali metal salt, an alkaline earth metal salt, an ammonium salt or a $N^+(C_{1-4}\text{ alkyl})_4$ salt. This invention also envisions the quaternization of any basic nitrogen-containing groups of the compounds disclosed herein. Water or oil-soluble or dispersable products may be obtained by such quaternization. Representative alkali or alkaline earth metal salts include sodium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, $C_{1-8}$ sulfonate and aryl sulfonate.

A "solvate" refers to an association or complex of one or more solvent molecules and a compound of the invention. Examples of solvents that form solvates include, but are not limited to, water, isopropanol, ethanol, methanol, DMSO, ethyl acetate, acetic acid, and ethanolamine. The term "hydrate" refers to the complex where the solvent molecule is water.

The term "protecting group" or "PG" refers to a substituent that is commonly employed to block or protect a particular functionality while reacting other functional groups on the compound. For example, an "amino-protecting group" is a substituent attached to an amino group that blocks or protects the amino functionality in the compound. Suitable amino-protecting groups include acetyl, trifluoroacetyl, t-butoxycarbonyl (BOC, Boc), benzyloxycarbonyl (CBZ, Cbz) and 9-fluorenylmethylenoxy-carbonyl (Fmoc). Similarly, a "hydroxy-protecting group" refers to a substituent of a hydroxy group that blocks or protects the hydroxy functionality. Suitable protecting groups include acetyl and silyl. A "carboxy-protecting group" refers to a substituent of the carboxy group that blocks or protects the carboxy functionality. Common carboxy-protecting groups include —CH$_2$CH$_2$SO$_2$Ph, cyanoethyl, 2-(trimethylsilyl)ethyl, 2-(trimethylsilyl)ethoxymethyl, 2-(p-toluenesulfonyl)ethyl, 2-(p-nitrophenylsulfenyl)ethyl, 2-(diphenylphosphino)ethyl, nitroethyl and the like. For a general description of protecting groups and their use, see Greene et al., *Protective Groups in Organic Synthesis*, John Wiley & Sons, New York, 1991 and Kocienski et al., *Protecting Groups*, Thieme, Stuttgart, 2005.

DESCRIPTION OF COMPOUNDS OF THE INVENTION

The present invention provides prodrugs of vemurafenib, salts, and pharmaceutical formulations thereof, which are potentially useful in the treatment of diseases, conditions and disorders modulated by protein kinases, especially B-Raf kinase. More specifically, the present invention provides a compound of Formula (I):

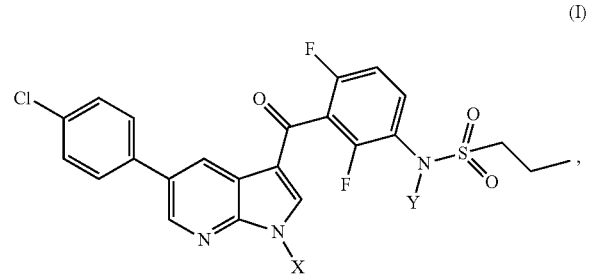

(I)

or a racemic mixture, a stereoisomer, a geometric isomer, a tautomer, a solvate, an N-oxide, a metabolite or a pharmaceutically acceptable salt thereof, wherein each of X and Y is as defined herein.

In some embodiments, each of X and Y is independently H, —C(=O)R$^3$, —C(=O)OR$^4$, —C(R$^1$R$^2$)OC(=O)R$^3$, —C(R$^1$R$^2$)OC(=O)OR$^4$ or —C(R$^1$R$^2$)OP(=O)(OR$^4$)(OR$^{4a}$), with the proviso that when Y is H, X is not —C(=O)CH$_3$ or H;

each R$^1$ and R$^2$ is independently H, D, C$_{1-6}$alkyl, C$_{1-6}$haloalkyl, C$_{3-6}$cycloalkyl, —(C$_{1-4}$ alkylene)-(C$_{3-6}$cycloalkyl), C$_{3-6}$heterocyclyl or —(C$_{1-4}$alkylene)-(C$_{3-6}$heterocyclyl); or R$^1$ and R$^2$, together with the carbon atom they are attached to, form an unsubstituted or substituted 3-8 membered carbocyclic or heterocyclic ring;

each R$^3$ is independently H, D, C$_{1-10}$alkyl, C$_{1-10}$haloalkyl, C$_{3-8}$cycloalkyl, —(C$_{1-6}$alkylene)-(C$_{3-8}$cycloalkyl), C$_{3-8}$heterocyclyl, —(C$_{1-6}$alkylene)-(C$_{3-8}$heterocyclyl), C$_{6-10}$aryl, —(C$_{1-6}$alkylene)-(C$_{6-10}$aryl), 5-10 membered heteroaryl or —(C$_{1-6}$alkylene)-(5-10 membered heteroaryl), wherein each of the C$_{1-10}$alkyl, C$_{1-10}$haloalkyl, C$_{3-8}$cycloalkyl, —(C$_{1-6}$alkylene)-(C$_{3-8}$cycloalkyl), C$_{3-8}$heterocyclyl, —(C$_{1-6}$alkylene)-(C$_{3-8}$heterocyclyl), C$_{6-10}$aryl, —(C$_{1-6}$alkylene)-(C$_{6-10}$aryl), 5-10 membered heteroaryl and —(C$_{1-6}$alkylene)-(5-10 membered heteroaryl) is unsubstituted or optionally substituted with 1, 2, 3 or 4 substituents independently selected from D, F, Cl, Br, I, C$_{1-6}$alkyl, C$_{1-6}$haloalkyl, —OH, —NH$_2$, C$_{1-6}$alkoxy and C$_{1-6}$alkylamino; and each R$^4$ and R$^{4a}$ is independently H, C$_{1-10}$alkyl, C$_{1-10}$haloalkyl, C$_{3-8}$cycloalkyl, —(C$_{1-6}$alkylene)-(C$_{3-8}$cycloalkyl), C$_{3-8}$heterocyclyl, —(C$_{1-6}$alkylene)-(C$_{3-8}$heterocyclyl), C$_{6-10}$aryl, —(C$_{1-6}$alkylene)-(C$_{6-10}$aryl), 5-10 membered heteroaryl or —(C$_{1-6}$alkylene)-(5-10 membered heteroaryl), wherein each of the C$_{1-10}$alkyl, C$_{1-10}$haloalkyl, C$_{3-8}$cycloalkyl, —(C$_{1-6}$alkylene)-(C$_{3-8}$cycloalkyl), C$_{3-8}$heterocyclyl, —(C$_{1-6}$alkylene)-(C$_{3-8}$heterocyclyl), C$_{6-10}$aryl, —(C$_{1-6}$alkylene)-(C$_{6-10}$aryl), 5-10 membered heteroaryl and —(C$_{1-6}$alkylene)-(5-10 membered heteroaryl) is unsubstituted or optionally substituted with 1, 2, 3 or 4 substituents independently selected from D, F, Cl, OH, NH$_2$, oxo (=O), C$_{1-6}$alkyl, C$_{1-6}$haloalkyl, C$_{1-6}$alkoxy and C$_{1-6}$alkylamino.

In other embodiments, each R$^1$ and R$^2$ is independently H, D or C$_{1-3}$alkyl.

In other embodiments, each R$^3$ is independently C$_{1-10}$alkyl, C$_{3-8}$cycloalkyl, —(C$_{1-6}$alkylene)-(C$_{3-8}$cycloalkyl), C$_{3-8}$heterocyclyl, —(C$_{1-6}$alkylene)-(C$_{3-8}$heterocyclyl), C$_{6-10}$aryl, —(C$_{1-6}$alkylene)-(C$_{6-10}$aryl), 5-10 membered heteroaryl or —(C$_{1-6}$alkylene)-(5-10 membered heteroaryl), wherein each of the C$_{1-10}$alkyl, C$_{3-8}$cycloalkyl, —(C$_{1-6}$alkylene)-(C$_{3-8}$cycloalkyl), C$_{3-8}$heterocyclyl, —(C$_{1-6}$alkylene)-(C$_{3-8}$heterocyclyl), C$_{6-10}$aryl, —(C$_{1-6}$alkylene)-(C$_{6-10}$aryl), 5-10 membered heteroaryl and —(C$_{1-6}$alkylene)-(5-10 membered heteroaryl) is unsubstituted or optionally substituted with 1, 2, 3 or 4 substituents independently selected from D, F, —OH, —OMe, —NH$_2$, —NHMe, —NMe$_2$ and C$_{1-3}$alkyl.

In other embodiments, each R$^4$ and R$^{4a}$ is independently H, C$_{1-10}$alkyl, C$_{3-8}$cycloalkyl, —(C$_{1-6}$alkylene)-(C$_{3-8}$cycloalkyl), C$_{3-8}$heterocyclyl, —(C$_{1-6}$alkylene)-(C$_{1-3-8}$ heterocyclyl) or C$_{6-10}$aryl, wherein each of the C$_{1-10}$alkyl, C$_{3-8}$cycloalkyl, —(C$_{1-6}$alkylene)-(C$_{3-8}$cycloalkyl), C$_{3-8}$heterocyclyl, —(C$_{1-6}$alkylene)-(C$_{3-8}$heterocyclyl) and C$_{6-10}$aryl is unsubstituted or optionally substituted with 1, 2, 3 or 4 substituents independently selected from D, F, OH, OMe, oxo (=O), NH$_2$, —NHMe, —NMe$_2$ and C$_{1-3}$alkyl.

In other embodiments, each of X and Y is independently H or —C(R$^1$R$^2$)OP(=O)(OH)$_2$, with the proviso that when Y is H, X is not H.

In other embodiments, each of X and Y is independently H, —C(=O)R$^3$, —C(=O)OR$^4$, —C(R$^1$R$^2$)OC(=O)R$^3$ or —C(R$^1$R$^2$)OC(=O)OR$^4$, with the proviso that when Y is H, X is not —C(=O)CH$_3$ or H.

In other embodiments, the acyl moiety (—C(=O)R$^3$) is derived from an α-amino acid or an optical isomer thereof by removing the OH group from the carboxy group of the α-amino acid.

In other embodiments, the α-amino acid is isoleucine, leucine, lysine, methionine, phenylalanine, threonine, tryptophan, valine, alanine, asparagine, aspartate, glutamate, glutamine, proline, serine, para-tyrosine, arginine, histidine, cysteine, glycine, sarcosine, N,N-dimethyl glycine, homoserine, norvaline, norleucine, ornithine, homocysteine, homophenylalanine, phenylglycine, ortho-tyrosine, meta-tyrosine or hydroxyproline.

In other embodiments, the α-amino acid is isoleucine, leucine, lysine, methionine, phenylalanine, threonine, tryptophan, valine, alanine, asparagine, aspartate, glutamate, glutamine, proline, serine, tyrosine, arginineor histidine, each of which has a S-configuration at the α-position.

In other embodiments, the pharmaceutically acceptable salt is an alkali metal salt, an alkaline earth metal salt, or an ammonium or N'(C$_{1-4}$ alkyl)$_4$ salt.

In other embodiments, the pharmaceutically acceptable salt is a sodium salt, a lithium salt, a potassium salt, a calcium salt, a magnesium salt, an ammonium salt, a quaternary ammonium salt, or a combination thereof.

In other embodiments, the pharmaceutically acceptable salt is a salt of an inorganic acid, an organic acid or a combination thereof, wherein the inorganic acid or the organic acid is hydrochloric acid, hydrobromic acid, sulfuric acid, nitric acid, phosphoric acid, acetic acid, maleic acid, succinic acid, mandelic acid, fumaric acid, malonic acid, malic acid, 2-hydroxypropanic acid, pyruvic acid, oxalic acid, glycolic acid, salicylic acid, glucuronic acid, galacturonic acid, citric acid, tartaric acid, aspartic acid, glutamic acid, benzoic acid, cinnamic acid, p-toluenesulfonic acid, benzenesulfonic acid, mthanesulfonic acid, ethanesulfonic acid, trifluoromthanesulfonic acid or a combination thereof.

Some non-limiting examples of the compounds disclosed herein, and their pharmaceutically acceptable salts and solvates thereof, include:

TABLE 1

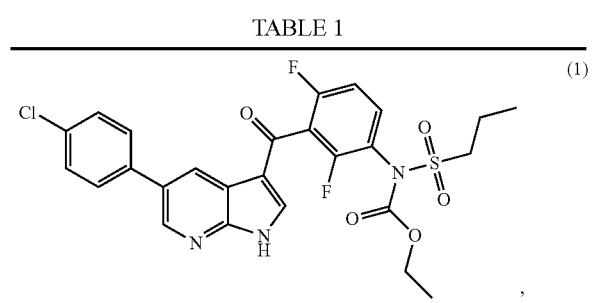
(1)

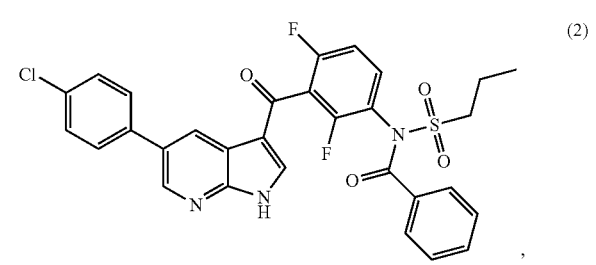
(2)

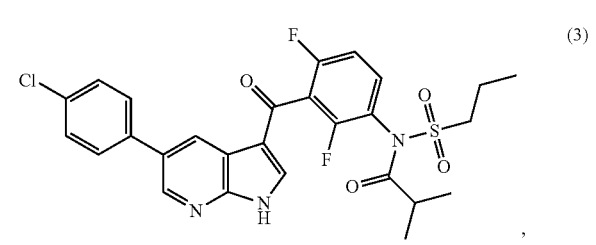
(3)

TABLE 1-continued

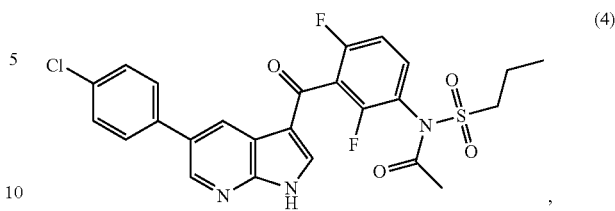
(4)

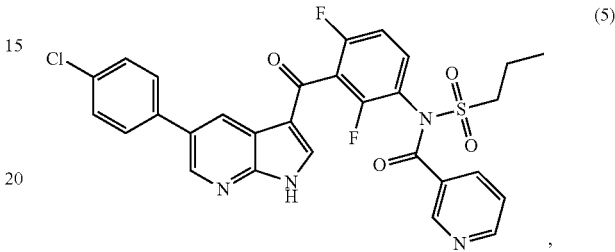
(5)

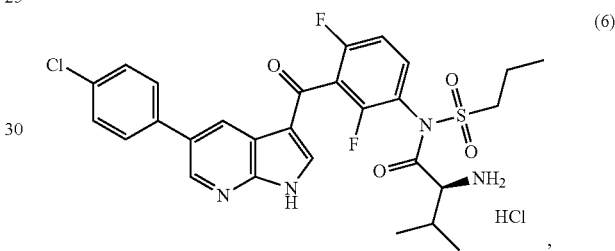
(6)

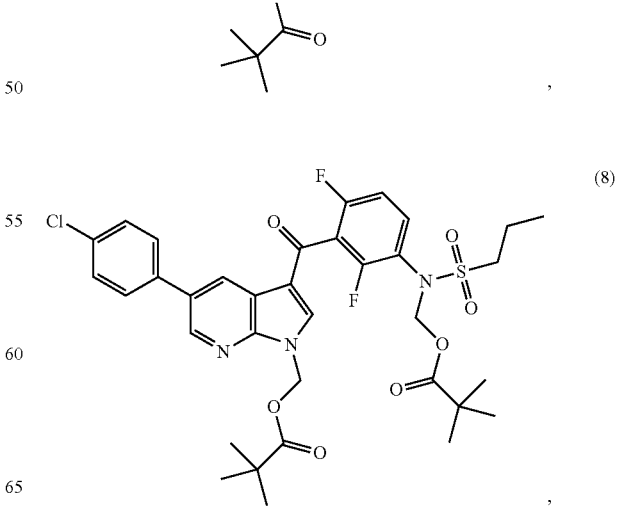
(7)

(8)

TABLE 1-continued
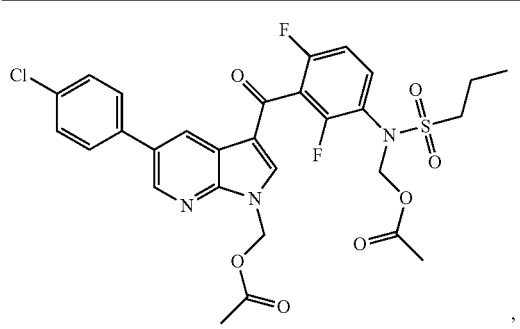
(9)
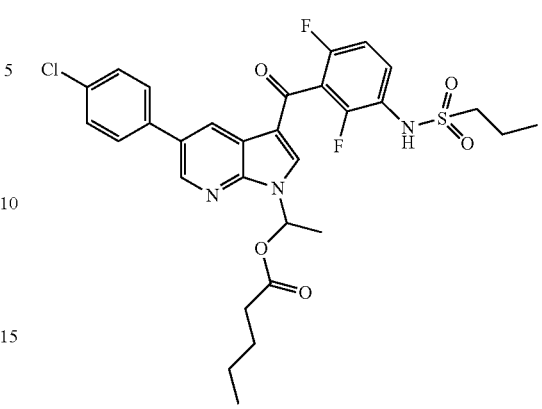
(13)
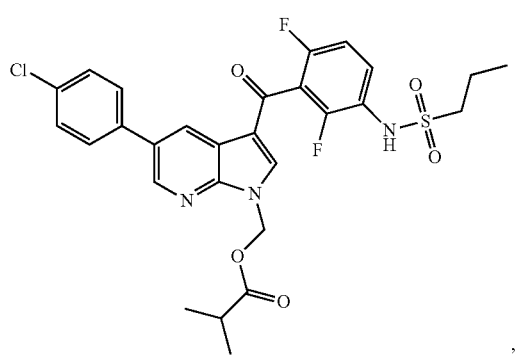 [SMILES: CCCS(=O)(=O)Nc1ccc(F)c(C(=O)c2cn(COC(=O)C(C)C)c3ncc(-c4ccc(Cl)cc4)cc23)c1F]
(10)
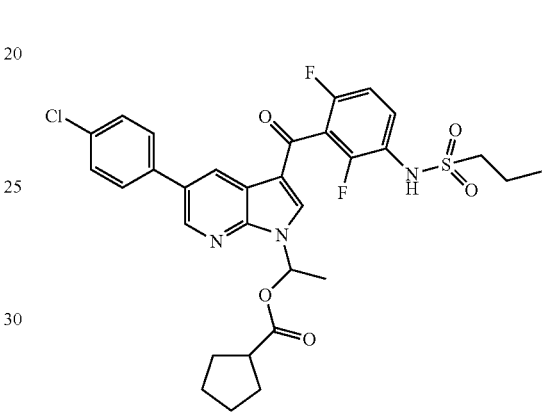
(14)
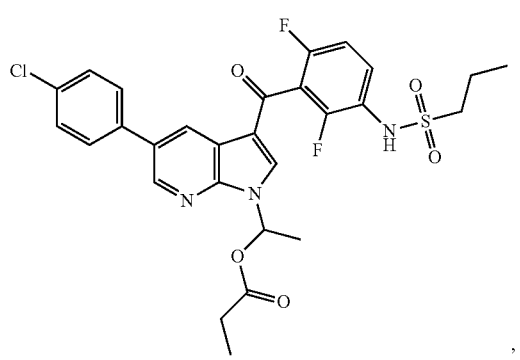 [SMILES: CCCS(=O)(=O)Nc1ccc(F)c(C(=O)c2cn(C(C)OC(=O)CC)c3ncc(-c4ccc(Cl)cc4)cc23)c1F]
(11)
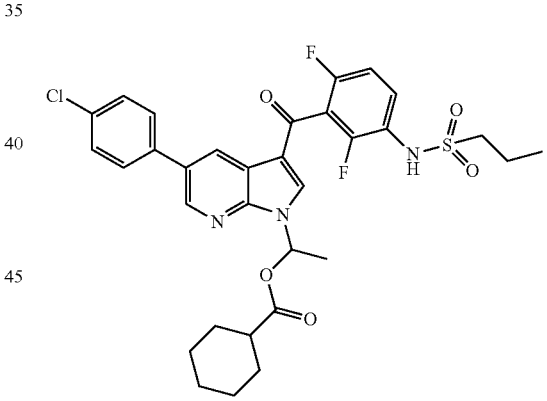
(15)
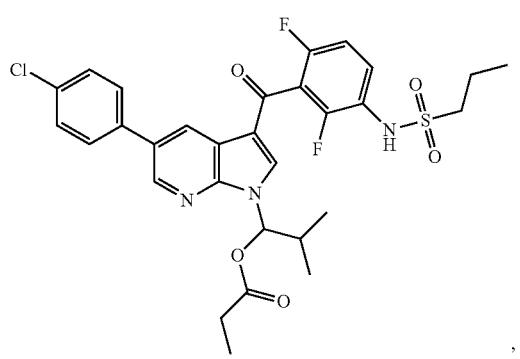 [SMILES: CCCS(=O)(=O)Nc1ccc(F)c(C(=O)c2cn(C(OC(=O)CC)C(C)C)c3ncc(-c4ccc(Cl)cc4)cc23)c1F]
(12)
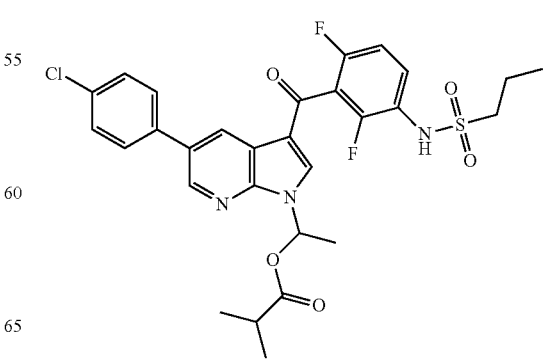
(16)

TABLE 1-continued
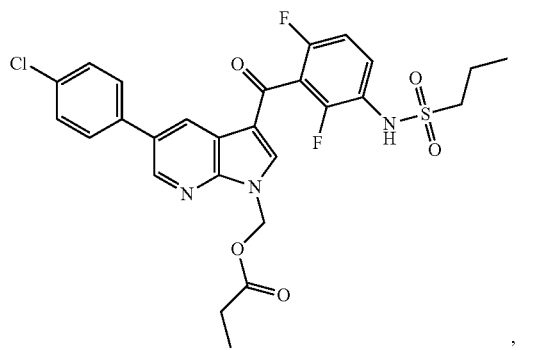 [SMILES: CCCS(=O)(=O)Nc1ccc(F)c(C(=O)c2cn(COC(=O)CC)c3ncc(-c4ccc(Cl)cc4)cc23)c1F]
(17)
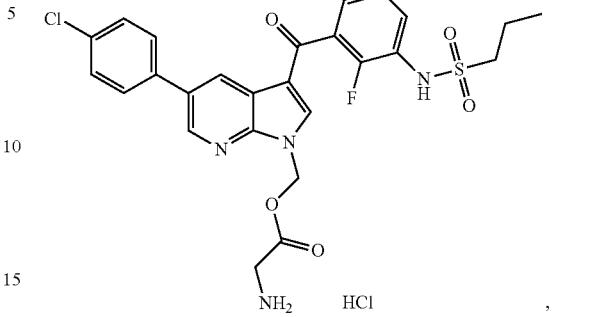
(21)
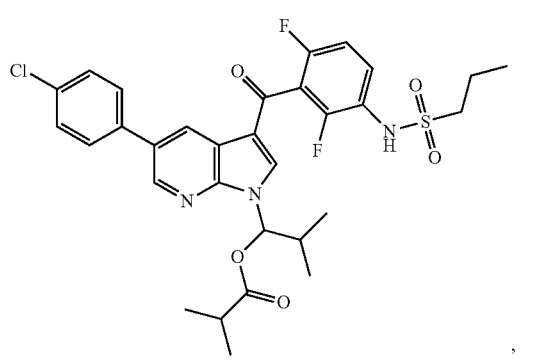 [SMILES: CCCS(=O)(=O)Nc1ccc(F)c(C(=O)c2cn(C(OC(=O)C(C)C)C(C)C)c3ncc(-c4ccc(Cl)cc4)cc23)c1F]
(18)
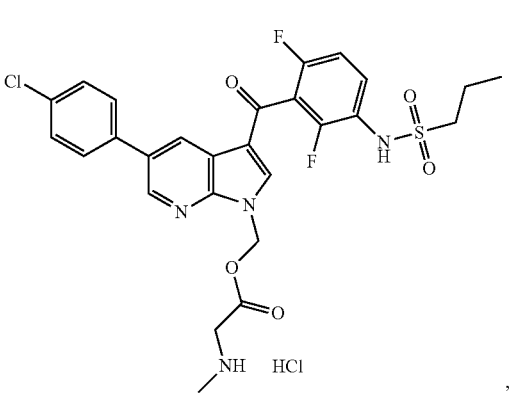 [SMILES: CCCS(=O)(=O)Nc1ccc(F)c(C(=O)c2cn(COC(=O)CNC)c3ncc(-c4ccc(Cl)cc4)cc23)c1F ; Cl]
(22)
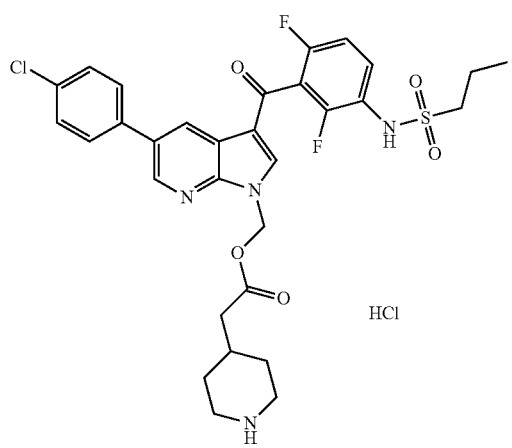
(19)
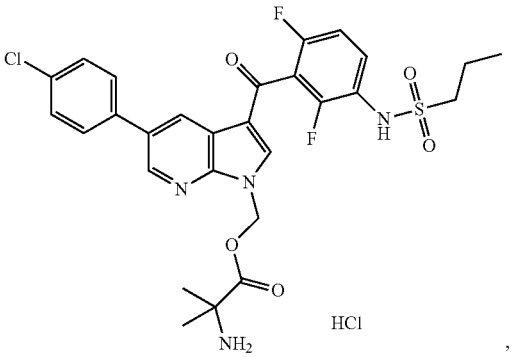 [SMILES: CCCS(=O)(=O)Nc1ccc(F)c(C(=O)c2cn(COC(=O)C(C)(C)N)c3ncc(-c4ccc(Cl)cc4)cc23)c1F ; Cl]
(23)
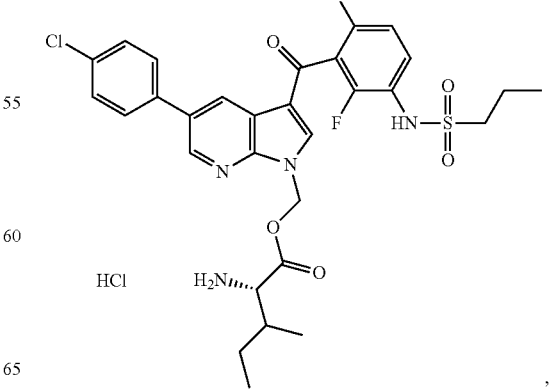
(24)
(20)

TABLE 1-continued
(25)
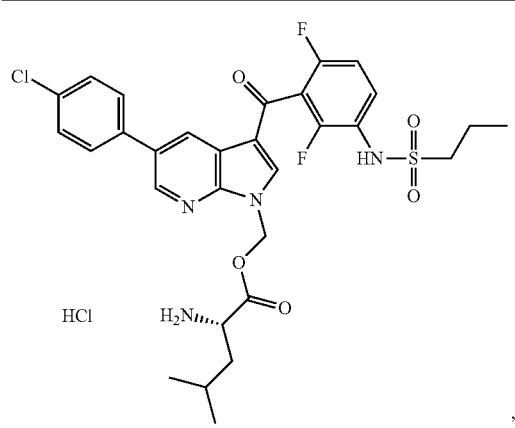
(26)
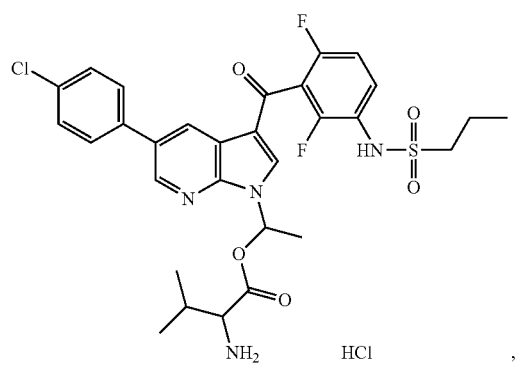 [SMILES: CCCS(=O)(=O)Nc1ccc(F)c(C(=O)c2cn(C(C)OC(=O)C(N)C(C)C)c3ncc(-c4ccc(Cl)cc4)cc23)c1F ; Cl]
(27)
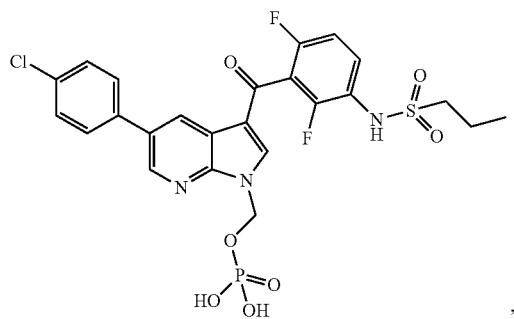 [SMILES: CCCS(=O)(=O)Nc1ccc(F)c(C(=O)c2cn(COP(=O)(O)O)c3ncc(-c4ccc(Cl)cc4)cc23)c1F]
(28)
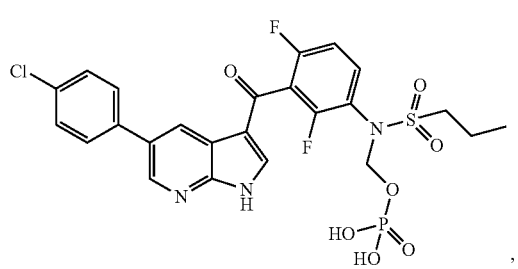 [SMILES: CCCS(=O)(=O)N(COP(=O)(O)O)c1ccc(F)c(C(=O)c2c[nH]c3ncc(-c4ccc(Cl)cc4)cc23)c1F]
TABLE 1-continued
(29)
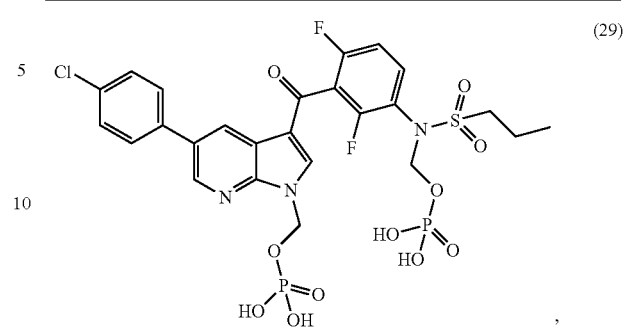
(30)
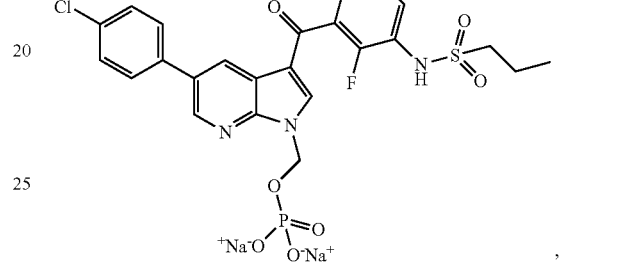
(31)
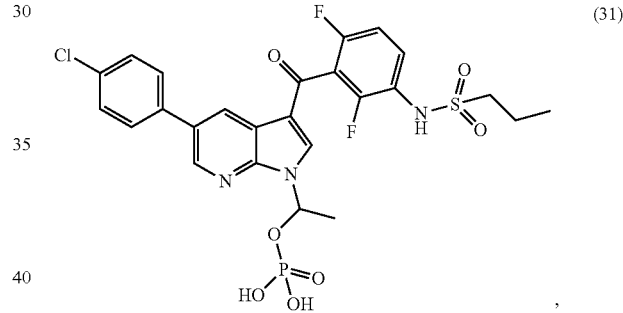
(32)
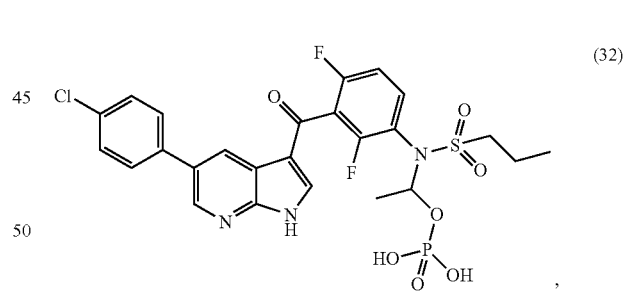
(33)
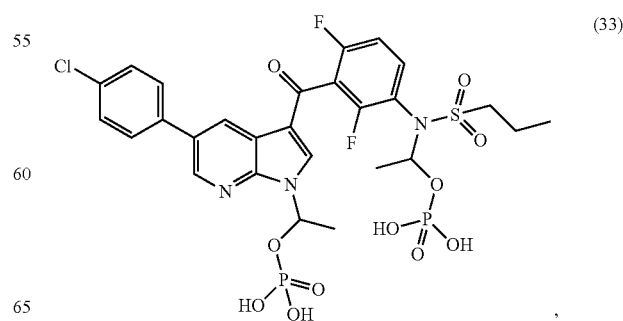

TABLE 1-continued
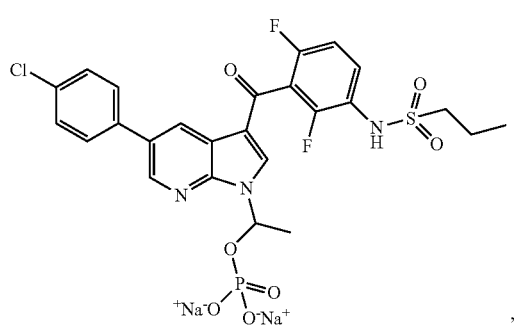
(34)
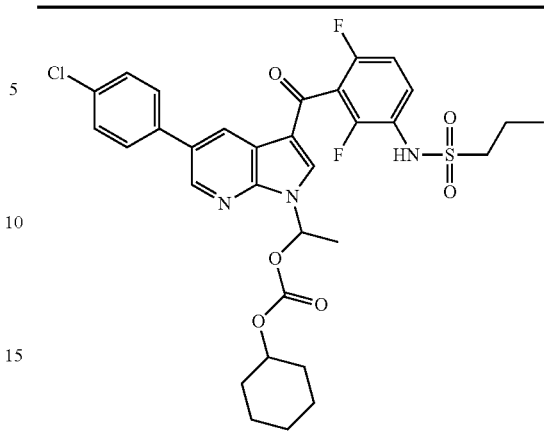
(38)
,
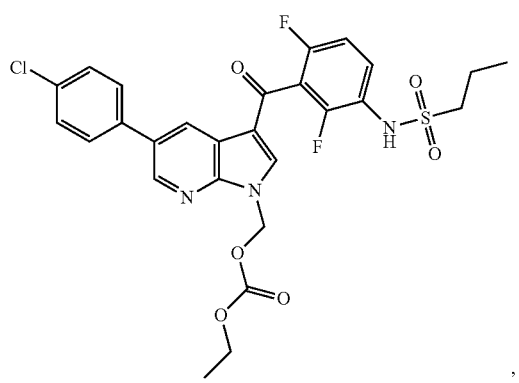 [SMILES: CCCS(=O)(=O)Nc1ccc(F)c(C(=O)c2cn(COC(=O)OCC)c3ncc(-c4ccc(Cl)cc4)cc23)c1F]
(35)
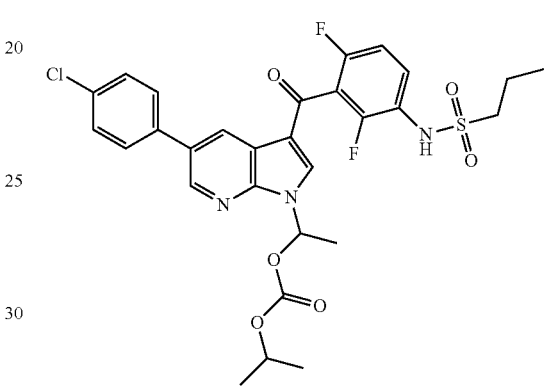
(39)
,
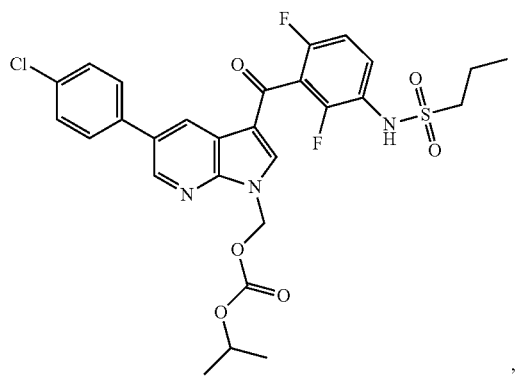 [SMILES: CCCS(=O)(=O)Nc1ccc(F)c(C(=O)c2cn(COC(=O)OC(C)C)c3ncc(-c4ccc(Cl)cc4)cc23)c1F]
(36)
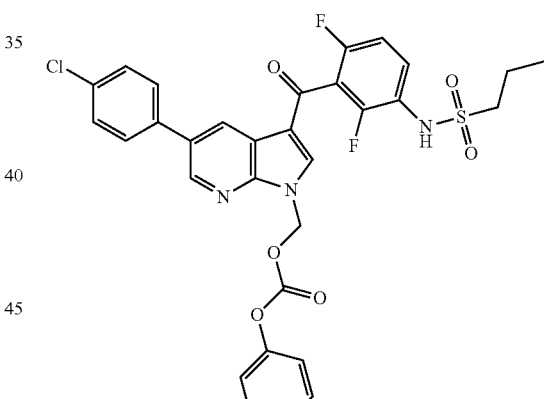
(40)
,
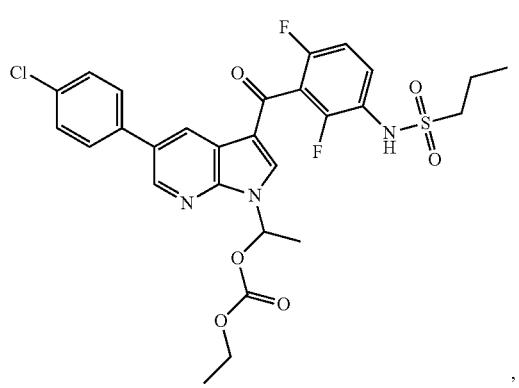 [SMILES: CCCS(=O)(=O)Nc1ccc(F)c(C(=O)c2cn(C(C)OC(=O)OCC)c3ncc(-c4ccc(Cl)cc4)cc23)c1F]
(37)
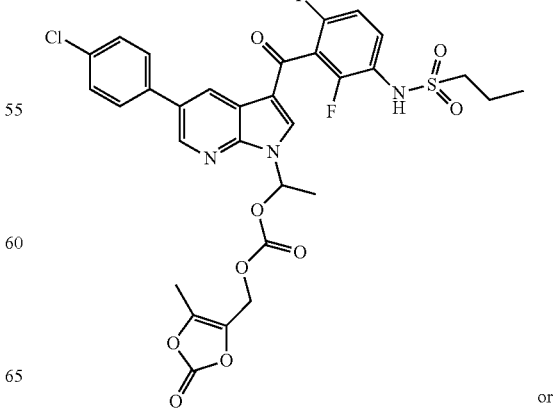
(41)
, or

TABLE 1-continued

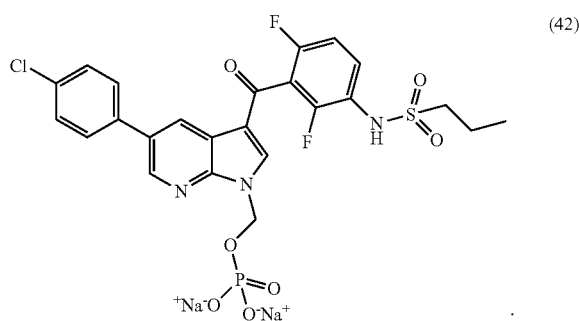

(42)

The present invention also comprises the use of a compound of the invention, or pharmaceutically acceptable salt thereof, in the manufacture of a medicament for the treatment either acutely or chronically of a hyperproliferative disease state and/or an angiogenesis mediated disease state, including those described previously. The compounds of the present invention are useful in the manufacture of an anti-cancer medicament. The compounds of the present invention are also useful in the manufacture of a medicament to attenuate or prevent disorders through inhibition of protein kinases. The present invention comprises a pharmaceutical composition comprising a therapeutically effective amount of a compound of Formula (I) in association with at least one pharmaceutically acceptable carrier, adjuvant or diluent.

The present invention also comprises a method of treating hyperproliferating and angiogenesis related disorders in a subject having or susceptible to such disorder, the method comprising treating the subject with a therapeutically effective amount of a compound of Formula (I).

Unless otherwise stated, all stereoisomers, geometric isomers, tautomers, solvates, metabolites, salts, and pharmaceutically acceptable prodrugs of the compounds of the invention are within the scope of the invention.

In certain embodiments, the salt is a pharmaceutically acceptable salt. The phrase "pharmaceutically acceptable" indicates that the substance or composition must be compatible chemically and/or toxicologically, with the other ingredients comprising a formulation, and/or the mammal being treated therewith.

The compounds of the invention also include salts of such compounds which are not necessarily pharmaceutically acceptable salts, and which may be useful as intermediates for preparing and/or purifying compounds of Formula (I) and/or for separating enantiomers of compounds of Formula (I).

Prodrug salts may be prepared in a variety of ways familiar to the skilled artisan, or according to the methods described herein. For example, a prodrug bearing an acidic prodrug group may be converted to the corresponding prodrug salt by treating with a base, followed by isolation through, for example, concentration, precipitation, or crystallization. If there exist more than one acidic hydrogen in the prodrug, then polyanionic salts may be prepared with the appropriate stoichiometric ration of base and prodrug. For example, a dianion may be formed from a prodrug containing a —P(═O)(OH)$_2$ group with two equivalents of an appropriate base. Preferred salts of prodrugs of the invention include, but not limited to, sodium, potassium, calcium, magnesium, ammonium, and the like. Alternatively, an organic base may be used to prepare salts of the prodrug of the invention. Examples of preferred organic bases include, but are not limited to, lysine, arginine, N,N-diethylethanolamine, diethanolamine, ethanolamine, ethylenediamine, meglumine, morpholine, piperazine, piperidine, triethylamine, tromethamine (Tris), benzathine, benzene-ethanamine, adenine, cytosine and guanidine. As described in more detailed below, the prodrug salts may be formed in aqueous solution. Alternatively, they may be made in organic solution using and organic base such as sodium methoxide.

The cation may be exchanged by treating a solution of the desired prodrug anion with an appropriate cationic species to form an insoluble salt. The prodrug salt hydrates may be prepared, for example, by salt formation, isolation, or crystallization from aqueous solution.

In case that a prodrug bearing an basic group, the prodrug may be converted to the corresponding prodrug salt by treating the free base with an inorganic acid, such as hydrochloric acid, hydrobromic acid, sulfuric acid, nitric acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an alpha hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like.

Compounds disclosed herein are prodrugs. These compounds typically do not exhibit inhibitory activities against certain protein kinases in in vitro assays. However, the prodrug compounds are modified in vivo to produce a parent compound that has known inhibitory activities against certain protein kinases. Kinase inhibition activity of prodrug compounds is established by quantitating the blood or plasma levels of parent compound after prodrug administration. In vivo blood or plasma levels are reported as Cmax (maximum blood or plasma concentration) and AUC (area under curve from zero to a certain period of time or infinity, a measure of total drug exposure). Methods of measuring Cmax, AUC and other pharmacokinetic parameters in dogs and rats are provided in Example C.

Prodrug compounds are often, for example, better absorbed in vivo leading to higher overall blood or plasma levels of parent drug compound If both prodrug and parent compound are administered orally at the same doses.
Composition, Formulations and Administration of Compounds of The Invention According to one aspect, the invention features pharmaceutical compositions that include a compound of formula (I), a compound listed in Table 1, and a pharmaceutically acceptable carrier, adjuvant, or vehicle. The amount of compound in the compositions of the invention is such that is effective to detectably inhibit a protein kinase in a biological sample or in a patient.

As described above, the pharmaceutically acceptable compositions of the present invention additionally comprise a pharmaceutically acceptable carrier, adjuvant, or vehicle, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Troy et al., *Remington: The Science and Practice of Pharmacy*, 21st, 2005, Lippincott Williams & Wilkins, Philadelphia and Swarbrick et al., Encyclopedia of Pharmaceutical Technology, eds. 1988-1999, Marcel Dekker, New York, all of which are herein incorporated by reference in their entireties, are disclosed various carriers used in formulating pharmaceutically acceptable compositions and known techniques for the preparation thereof. Except insofar as any conventional carrier medium is incompatible with the compounds of the invention such as by producing any undesirable biological effect or otherwise interacting in a deleterious manner with any other component(s) of the pharmaceutically acceptable composition, its use is contemplated to be within the scope of this invention.

Some non-limiting examples of materials which can serve as pharmaceutically acceptable carriers include ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The compositions of the present invention may be administered orally, parenterally, by inhalation spray, topically, rectally, nasally, buccally, vaginally or via an implanted reservoir. The term "parenteral" includes subcutaneous, intravenous, intramuscular, intra-articular, intra-synovial, intrasternal, intrathecal, intraocular, intrahepatic, intralesional and intracranial injection or infusion techniques. Preferably, the compositions are administered orally, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as TWEEN®, SPAN® and other emulsifying agents or bioavailability enhancers which are commonly used in the manufacture of pharmaceutically acceptable solid, liquid, or other dosage forms may also be used for the purposes of formulation.

Some non-limiting examples of the pharmaceutically acceptable compositions of this invention may be orally administered in any orally acceptable dosage form including capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, the pharmaceutically acceptable compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

The pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used. For topical applications, the pharmaceutically acceptable compositions may be formulated in a suitable ointment containing the active component suspended or dissolved in one or more carriers. Some non-limiting examples of carriers for topical administration of the compounds of this invention include mineral oil, liquid petrolatum, white petrolatum, propylene glycol, polyoxyethylene, polyoxypropylene compound, emulsifying wax and water. Alternatively, the pharmaceutically acceptable compositions can be formulated in a suitable lotion or cream containing the active components suspended or dissolved in one or more pharmaceutically acceptable carriers. Some non-limiting examples of suitable carriers include mineral oil, sorbitan monostearate, polysorbate 60, cetyl esters wax, cetearyl alcohol, 2-octyldodecanol, benzyl alcohol and water.

For ophthalmic use, the pharmaceutically acceptable compositions may be formulated, e.g., as micronized suspensions in isotonic, pH adjusted sterile saline or other aqueous solution, or, preferably, as solutions in isotonic, pH adjusted sterile saline or other aqueous solution, either with or without a preservative such as benzylalkonium chloride. Alternatively, for ophthalmic uses, the pharmaceutically acceptable compositions may be formulated in an ointment such as petrolatum. The pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Some non-limiting examples of liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use. In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, dissolving or suspending the compound in an oil vehicle accomplishes delayed absorption of a parenterally administered compound form.

Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polythylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain pacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, eardrops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

The compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts.

The amount of the compounds of the present invention that may be combined with the carrier materials to produce a composition in a single dosage form will vary depending upon the host treated, the particular mode of administration. Preferably, the compositions should be formulated so that a dosage of between 0.01-200 mg/kg body weight/day of the inhibitor can be administered to a patient receiving these compositions.

Compounds of this invention can be administered as the sole pharmaceutical agent or in combination with one or more other additional therapeutic (pharmaceutical) agents where the combination causes no unacceptable adverse effects. This may be of particular relevance for the treatment of hyperproliferative diseases such as cancer. In this instance, the compound of this invention can be combined with known cytotoxic agents, signal transduction inhibitors, or with other anti-cancer agents, as well as with admixtures and combinations thereof. As used herein, additional therapeutic agents that are normally administered to treat a particular disease, or condition, are known as "appropriate for the disease, or condition, being treated". As used herein, "additional therapeutic agents" is meant to include chemotherapeutic agents and other anti-proliferative agents.

For example, chemotherapeutic agents or other antiproliferative agents may be combined with the compounds of this invention to treat proliferative disease or cancer. Some nonlimiting examples of chemotherapeutic agents or other anti-proliferative agents include HDAC inhibitors including SAHA, MS-275, MGO 103, and those described in WO 2006/010264, WO 03/024448, WO 2004/069823, US 2006/0058298, US 2005/0288282, WO 00/71703, WO 01/38322, WO 01/70675, WO 03/006652, WO 2004/035525, WO 2005/030705, WO 2005/092899, and demethylating agents including, but not limited to, 5-aza-dC, Vidaza and Decitabine and those described in U.S. Pat. No. 6,268,137, U.S. Pat. No. 5,578,716, U.S. Pat. No. 5,919,772, U.S. Pat. No. 6,054,439, U.S. Pat. No. 6,184,211, U.S. Pat. No. 6,020,318, U.S. Pat. No. 6,066,625, U.S. Pat. No. 6,506,735, U.S. Pat. No. 6,221,849, U.S. Pat. No. 6,953,783, U.S. Ser. No. 11/393,380.

In another embodiment of the present invention, for example, chemotherapeutic agents or other anti-proliferative agents may be combined with the compounds of this invention to treat proliferative diseases and cancer. Some nonlimiting examples of known chemotherapeutic agents include other therapies or anticancer agents that may be used in combination with the inventive anticancer agents of the present invention and include surgery, radiotherapy (in but a few examples, gamma radiation, neutron beam radiotherapy, electron beam radiotherapy, proton therapy, brachytherapy, and systemic radioactive isotopes, to name a few), endocrine therapy, taxanes (taxol, taxotere etc), platinum derivatives (cisplatin, carboplatin), biologic response modifiers (interferons, interleukins), tumor necrosis factor (TNF, TRAIL receptor targeting agents, to name a few), hyperthermia and cryotherapy, agents to attenuate any adverse effects (e.g., antiemetics), and other approved chemotherapeutic drugs, including, but not limited to, alkylating drugs (mechlorethamine, chlorambucil, cyclophosphamide, melphalan, ifosfamide), antimetabolites (methotrexate, pemetrexed etc), purine antagonists and pyrimidine antagonists (6-mercaptopurine, 5-fluorouracil, cytarabile, gemcitabine), spindle poisons (vinblastine, vincristine, vinorelbine), podophyllotoxins (etoposide, irinotecan, topotecan), antibiotics (doxorubicin, bleomycin, mitomycin), nitrosoureas (carmustine, lomustine), cell cycle inhibitors (KSP mitotic kinesin inhibitors, CENP-E and CDK inhibitors), enzymes (asparaginase), hormones (tamoxifen, leuprolide, flutamide, megestrol, dexamethasone), antiangiogenic agents (avastin and others), monoclonal antibodies (BENLYSTA®), brentuximab (ADCETRIS®), cetuximab (ERBITUX®), gemtuzumab (MYLOTARG®), ipilimumab (YERVOY®), ofatumumab (ARZERRA®), panitumumab (VECTIBIX®), ranibizumab (LUCERTIS®), rituximab (RITUXAN®), tositumomab (BEXXAR®), trastuzumab (HERCEPTIN®)), kinase inhibitors (imatinib (GLEEVEC®), sunitinib (SUTENT®), sorafenib (NEXAVAR®), erlotinib, (TARCEVA®), gefitinib (IRESSA®), dasatinib (SPRYCEL®), nilotinib (TASIGNA®), lapatinib (TYKERB®), crizotinib (XALKORI®), ruxolitinib (JAKAFI®), vemurafenib (ZELBORAF®), vandetanib (CAPRELSA®), pazopanib (VOTRIENT®), and others), and agents inhibiting or activating cancer pathways such as the mTOR, HIF (hypoxia induced factor) pathways (such as everolimus and temsirolimus) and others. For a more comprehensive discussion of updated cancer therapies see, http://www.nci.nih.gov/, a list of the FDA approved oncology drugs at http://www.fda.gov/cder/cancer/druglist-rame.htm, and The Merck Manual, Eighteenth Ed. 2006, all of which are herein incorporated by reference in their entireties.

In another embodiment, the compounds of the present invention can be combined, with cytotoxic anti-cancer agents. Examples of such agents can be found in the 13th Edition of the Merck Index (2001). These agents include, by no way of limitation, asparaginase, bleomycin, carboplatin, carmustine, chlorambucil, cisplatin, colaspase, cyclophosphamide, cytarabine, dacarbazine, dactinomycin, daunorubicin, doxorubicin (adriamycine), epirubicin, etoposide, 5-fluorouracil, hexamethylmelamine, hydroxyurea, ifosfamide, irinotecan, leucovorin, lomustine, mechlorethamine, 6-mercaptopurine, mesna, methotrexate, mitomycin C, mitoxantrone, prednisolone, prednisone, procarbazine, raloxifen, streptozocin, tamoxifen, thioguanine, topotecan, vinblastine, vincristine and vindesine.

Other cytotoxic drugs suitable for use with the compounds of the invention include, but are not limited to, those compounds acknowledged to be used in the treatment of neoplastic diseases, such as those for example in Goodman and Gilman's The Pharmacological Basis of Therapeutics (Ninth Edition, 1996, McGraw-Hill). These agents include, by no way of limitation, aminoglutethimide, L-asparaginase, azathioprine, 5-azacytidine cladribine, busulfan, diethylstilbestrol, 2,2'-difluorodeoxycytidine, docetaxel, erythrohydroxynonyladenine, ethinyl estradiol, 5-fluorodeoxyuridine, 5-fluorodeoxyuridine monophosphate, fludarabine phosphate, fluoxymesterone, flutamide, hydroxyprogesterone caproate, idarubicin, interferon, medroxyprogesterone acetate, megestrol acetate, melphalan, mitotane, paclitaxel, pentostatin, N-phosphonoacetyl-L-aspartate (PALA), plicamycin, semustine, teniposide, testosterone propionate, thiotepa, trimethylmelamine, uridine, and vinorelbine.

Other cytotoxic anti-cancer agents suitable for use in combination with the compounds of the invention also include newly discovered cytotoxic principles such as oxaliplatin, vemurafenib, capecitabine, epothilone and its natural or synthetic derivatives, temozolomide (Quinn et al., *J. Clin. Oncol.*, 2003, 21(4), 646-651), tositumomab (BEXXAR®), trabedectin (Vidal et al., Proceedings of the American Society for Clinical Oncology, 2004, 23, abstract 3181), and the inhibitors of the kinesin spindle protein Eg5 (Wood et al., *Curr. Opin. Pharmacol.*, 2001, 1, 370-377).

In another embodiment, the compounds of the present invention can be combined with other signal transduction inhibitors. Examples of such agents include, by no way of limitation, antibody therapies such as trastuzumab (HERCEPTIN®), cetuximab (ERBITUX®), ipilimumab (YERVOY®) and pertuzumab. Examples of such therapies also include, by no way of limitation, small-molecule kinase inhibitors such as imatinib (GLEEVEC®), sunitinib (SUTENT®), sorafenib (NEXAVAR®), erlotinib (TARCEVA®), gefitinib (IRESSA®), dasatinib (SPRYCEL®), nilotinib (TASIGNA®), lapatinib (TYKERB®), crizotinib (XALKORI®), ruxolitinib (JAKAFI®), vemurafenib (ZELBORAF®), vandetanib (CAPRELSA®), pazopanib (VOTRIENT®), afatinib, alisertib, amuvatinib, axitinib, bosutinib, brivanib, canertinib, cabozantinib, cediranib, crenolanib, dabrafenib, dacomitinib, danusertib, dovitinib, foretinib, ganetespib, ibrutinib, iniparib, lenvatinib, linifanib, linsitinib, masitinib, momelotinib, motesanib, neratinib, niraparib, oprozomib, olaparib, pictilisib, ponatinib, quizartinib, regorafenib, rigosertib, rucaparib, saracatinib, saridegib, tandutinib, tasocitinib, telatinib, tivantinib, tivozanib, tofacitinib, trametinib, vatalanib, veliparib, vismodegib, volasertib, BMS-540215, BMS777607, JNJ38877605, TK1258, GDC-0941 (Folkes et al. *J. Med. Chem.* 2008, 51: 5522), BZE235, and others.

In another embodiment, the compounds of the present invention can be combined with inhibitors of histone deacetylase. Examples of such agents include, by no way of limitation, suberoylanilide hydroxamic acid (SAHA), LAQ-824 (Ottmann et al., Proceedings of the American Society for Clinical Oncology, 2004, 23, abstract 3024), LBH-589 (Beck et al., Proceedings of the American Society for Clinical Oncology, 2004, 23, abstract 3025), MS-275 (Ryan et al., Proceedings of the American Association of Cancer Research, 2004, 45, abstract 2452), FR-901228 (Piekarz et al., Proceedings of the American Society for Clinical Oncology, 2004, 23, abstract 3028) and MGCDOI 03 (U.S. Pat. No. 6,897,220).

In another embodiment, the compounds of the present invention can be combined with other anti-cancer agents such as proteasome inhibitors, and m-TOR inhibitors. These include, by no way of limitation, bortezomib, and CCI-779 (Wu et al., Proceedings of the American Association of Cancer Research 2004, 45, abstract 3849). The compounds of the present invention can be combined with other anti-cancer agents such as topoisomerase inhibitors, including but not limited to camptothecin.

Those additional agents may be administered separately from the compound-containing composition, as part of a multiple dosage regimen. Alternatively, those agents may be part of a single dosage form, mixed together with the compound of this invention in a single composition. If administered as part of a multiple dosage regimen, the two active agents may be submitted simultaneously, sequentially or within a period of time from one another which would result in the desired activity of the agents.

The amount of both the compound and the additional therapeutic agent (in those compositions which comprise an additional therapeutic agent as described above) that may be combined with the carrier materials to produce a single dosage form will vary depending upon the host treated and the particular mode of administration. Normally, the amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent. In those compositions which comprise an additional therapeutic agent, that additional therapeutic agent and the compound of this invention may act synergistically.

Uses of the Compounds and Effective Dosages

The invention features pharmaceutical compositions that include a compound of formula (I), or a compound listed in Table 1, and a pharmaceutically acceptable carrier, adjuvant, or vehicle. The amount of compound in the compositions of the invention is such that is effective to detectably inhibit a protein kinase, such as B-Raf kinase inhibitory activity. The compounds of the invention are useful in therapy as antineoplasia agents or to minimize deleterious effects of B-Raf signaling.

Compounds of the present invention would be useful for, but not limited to, the prevention or treatment of proliferative diseases, condition, or disorder in a patient by administering to the patient a compound or a composition of the invention in an effective amount. Such diseases, conditions, or disorders include cancer, metastatic cancer, atherosclerosis, and lung fibrosis.

Compounds of the invention would be useful for the treatment of neoplasia including cancer and metastasis, including, but not limited to: carcinoma such as cancer of the bladder, breast, colon, kidney, liver, lung (including small cell lung cancer), esophagus, gall-bladder, ovary, pancreas, stomach, cervix, thyroid, prostate, and skin (including squamous cell carcinoma); hematopoietic tumors of lymphoid lineage (including leukemia, acute lymphocytic leukemia, acute lymphoblastic leukemia, B-cell lymphoma, T-cell-lymphoma, Hodgkin's lymphoma, non-Hodgkin's lymphoma, hairy cell lymphoma and Burkett's lymphoma); hematopoietic tumors of myeloid lineage (including acute and chronic myelogenous leukemias, myelodysplastic syndrome and promyelocytic leukemia); tumors of mesenchymal origin (including fibrosarcoma and rhabdomyosarcoma, and other sarcomas, e.g. soft tissue and bone); tumors of the central and peripheral nervous system (including astrocytoma, neuroblastoma, glioma and schwannomas); and other tumors (including melanoma, seminoma, teratocarcinoma, osteosarcoma, xeroderma pigmentosum, keratoacanthoma, thyroid follicular cancer and Kaposi's sarcoma).

Currently, vemurafenib is indicated for the treatment of patients with unresectable or metastatic melanoma with $BRAF^{V600E}$ mutation as detected by an US FDA-approved test.

Besides being useful for human treatment, these compounds are also useful for veterinary treatment of companion animals, exotic animals and farm animals, including mammals, rodents, and the like. More preferred animals include horses, dogs, and cats.

As used herein, the compounds of the present invention include the pharmaceutically acceptable derivatives thereof.

Where the plural form is used for compounds, salts, and the like, this is taken to mean also a single compound, salt and the like.

The treatment method that includes administering a compound or composition of the invention can further include administering to the patient an additional therapeutic agent (combination therapy) selected from: a chemotherapeutic or anti-proliferative agent, or an anti-inflammatory agent, wherein the additional therapeutic agent is appropriate for the disease being treated and the additional therapeutic agent is administered together with a compound or composition of the invention as a single dosage form or separately from the compound or composition as part of a multiple dosage form. The additional therapeutic agent may be administered at the same time as a compound of the invention or at a different time. In the latter case, administration may be staggered by, for example, 6 hours, 12 hours, 1 day, 2 days, 3 days, 1 week, 2 weeks, 3 weeks, 1 month or 2 months.

The invention also features a method of inhibiting the growth of a cell that expresses mutated B-Raf, which includes contacting the cell with a compound or composition of the invention, thereby causing inhibition of growth of the cell. Examples of a cell whose growth can be inhibited include: a melanoma cell, a colorectal cancer cell, a breast cancer cell, a lung cancer cell, a papillary carcinoma cell, a prostate cancer cell, a lymphoma cell, a colon cancer cell, a pancreatic cancer cell, an ovarian cancer cell, a cervical cancer cell, a central nervous system cancer cell, an osteogenic sarcoma cell, a renal carcinoma cell, a hepatocellular carcinoma cell, a bladder cancer cell, a gastric carcinoma cell, a head and neck squamous carcinoma cell or a leukemia cell.

The invention provides a method of inhibiting mutated B-Raf kinase activity in a biological sample that includes contacting the biological sample with a compound or composition of the invention. The term "biological sample" means a sample outside a living organism and includes, without limitation, cell cultures or extracts thereof; biopsied material obtained from a mammal or extracts thereof; and blood, saliva, urine, feces, semen, tears, or other body fluids or extracts thereof. Inhibition of kinase activity, particularly mutated B-Raf kinase activity, in a biological sample is useful for a variety of purposes known to one of skill in the art. Non-limiting examples of such purposes include blood transfusion, organ-transplantation, biological specimen storage and biological assays.

In certain embodiments of the present invention an "effective amount" or "effective dose" of the compound or pharmaceutically acceptable composition is that amount effective for treating or lessening the severity of one or more of the aforementioned disorders. The compounds and compositions, according to the method of the present invention, may be administered using any amount and any route of administration effective for treating or lessening the severity of the disorder or disease. The exact amount required will vary from subject to subject, depending on the species, age, and general condition of the subject, the severity of the infection, the particular agent, its mode of administration, and the like. A compound or composition can also be administered with one or more other therapeutic agents, as discussed above.

Suitable dosage ranges for oral administration of the prodrug in the invention are dependent on the potency of vemurafenib in the particular indication of interest as well as the prodrug bioavailability. Dosage range may be readily determined by methods know to the artisan of ordinary skill. For example, vemurafenib is typically administered orally at a dose of 960 mg twice daily (bid) for the treatment of the indications of unresectable or metastatic melanoma with $BRAF^{V600E}$ mutation (as detected by an FDA-approved test).

The amount of a compound and/or pharmaceutical composition thereof that will be effective in the treatment of a particular disorder or condition disclosed herein can be determined by standard clinical techniques known in the art. In addition, in vitro or in vivo assays may optionally be employed to help identify optimal dosage ranges. The amount of a compound and/or pharmaceutical composition thereof administered will, of course, be dependent on, among other factors, the subject being treated (such as age, general health, sex, diet, weight, etc), the severity of the affliction, the manner, time and route of administration and the judgment of the prescribing physician.

The compounds are preferably assayed in vitro and in vivo, for the desired therapeutic or prophylactic activity, prior to use in humans. For example, in vitro assays can be used to determine whether administration of a specific compound or a combination of compounds is preferred. The compounds may also be demonstrated to be effective and safe using animal model systems. For example, vemurafenib is indicated for the treatment of patients with unresectable or metastatic melanoma with $BRAF^{V600E}$ mutation. Patients diagnosed with unresectable or metastatic melanoma were required to test their BARF mutation status before taken vemurafenib.

Preferably, a therapeutically effective dose of a compound and/or pharmaceutical composition thereof described herein will provide therapeutic benefit without causing substantial toxicity. Toxicity of compounds and/or pharmaceutical compositions thereof may be determined using standard pharmaceutical procedures and may be readily ascertained by the skilled artisan. The dose ratio between toxic and therapeutic effect is the therapeutic index. A compound and/or pharmaceutical composition thereof will preferably exhibit particularly high therapeutic indices in treating disease and disorders. The dosage of a compound and/or pharmaceutical composition thereof described herein will preferably be within a range of circulating concentrations that include an effective dose with minimal toxicity.

General Synthetic Procedures

In order to illustrate the invention, the following examples are included. However, it is to be understood that these examples do not limit the invention and are only meant to suggest a method of practicing the invention.

Generally, the compounds in this invention may be prepared by methods described herein, wherein the substituents are as defined for formula (I), above, except where further noted. The following non-limiting schemes and examples are presented to further exemplify the invention. Persons skilled in the art will recognize that the chemical reactions described herein may be readily adapted to prepare a number of other compounds of the invention, and alternative methods for preparing the compounds of this invention are deemed to be within the scope of this invention. For example, the synthesis of non-exemplified compounds according to the invention may be successfully performed by modifications apparent to those skilled in the art, e.g., by appropriately protecting interfering groups, by utilizing other suitable reagents known in the art other than those described, and/or by making routine modifications of reaction conditions. Alternatively, other reactions disclosed herein or known in the art will be recognized as having applicability for preparing other compounds of the invention.

In the examples described below, unless otherwise indicated all temperatures are set forth in degrees Celsius. Reagents were purchased from commercial suppliers such as Aldrich Chemical Company, Arco Chemical Company and Alfa Chemical Company, Shanghai Medpep. Co Ltd, Aladdin-Shanghai Jinchun Reagents, Ltd, and were used without further purification unless otherwise indicated. Common solvents were purchased from commercial suppliers such as Shantou XiLong Chemical Factory, Guangdong Guanghua Reagent Chemical Factory Co. Ltd., Guangzhou Reagent Chemical Factory, Tainjin YuYu Fine Chemical Ltd., Qingdao Tenglong Reagent Chemical Ltd., and Qingdao Ocean Chemical Factory.

Anhydrous THF, dioxane, toluene, and ether were obtained by refluxing the solvent with sodium Anhydrous $CH_2Cl_2$ and $CHCl_3$ were obtained by refluxing the solvent with $CaH_2$. EtOAc, PE, hexanes, DMA and DMF were treated with anhydrous $Na_2SO_4$ prior use.

The reactions set forth below were done generally under a positive pressure of nitrogen or argon or with a drying tube (unless otherwise stated) in anhydrous solvents, and the reaction flasks were typically fitted with rubber septa for the introduction of substrates and reagents via syringe. Glassware was oven dried and/or heat dried.

Column chromatography was conducted using a silica gel column. Silica gel (300-400 mesh) was purchased from Qingdao Ocean Chemical Factory. $^1$H NMR spectra were recorded with a Bruker 400 MHz spectrometer at ambient temperature. $^1$H NMR spectra were obtained as $CDCl_3$, $d_6$-DMSO, $CD_3OD$ or $d_6$-acetone solutions (reported in ppm), using TMS (0 ppm) or chloroform (7.25 ppm) as the reference standard. When peak multiplicities are reported, the following abbreviations are used: s (singlet), d (doublet), t (triplet), m (multiplet), br (broadened), dd (doublet of doublets), dt (doublet of triplets). Coupling constants, when given, are reported in Hertz (Hz).

Low-resolution mass spectral (MS) data were generally determined on an Agilent 1200 or Agilent 6120 Series LCMS [Column: Zorbax SB-C18, 2.1×30 mm, 3.5 micorn, 6 minutes run, 0.6 mL/min flow rate. Mobile phase: 5-95% (0.1% formic acid in $CH_3CN$) in (0.1% formic acid in $H_2O$)] with UV detection at 210/254 nm and a low resonance electrospray mode (ESI).

Purities of compounds were assessed by Agilent 1100 Series high performance liquid chromatography (HPLC) with UV detection at 210 nm and 254 nm. Column was normally operated at 40° C.

The following abbreviations are used throughout the specification:
BOC, Boc butyloxycarbonyl
BSA bovine serum albumin
$BF_3.Et_2O$ boron Trifluoride-Ethyl Ether Complex
$CDCl_3$ chloroform deuterated
$CHCl_3$ chloroform
$CH_2Cl_2$, DCM methylene chloride
$CH_3SO_2Cl$, MsCl methanesulfonyl chloride
$Cs_2CO_3$ cesium carbonate
CuI copper(I) iodide
DAST diethylaminosulfur trifluoride
DBU 1,8-diazabicyclo[5.4.0]undec-7-ene
DCE 1,2-dichloroethane
DEAD dimethyl azodicarboxylate
DIAD diisopropyl azodicarboxylate
DIBAL diisobutylaluminum hydride
DIEA, DIPEA diisopropylethylamine
DMAP 4-dimethylaminopyridine
DME 1,2-dimethoxyethane
DMF dimethylformamide
DMSO dimethylsulfoxide
DPPA diphenylphosphoryl azide
EDCI 1-(3-dimethylaminopropyl)-3-ethylcarbodiimide hydrochloride
EtOAc, EA ethyl acetate
$Et_2O$ diethyl ether
$Et_3N$, TEA triethylamine
EtOCOCl ethyl chloroformate
FBS fetal bovine serum
G gram
H hour
Min minute
HATU O-(7-azabenzotriazol-1-yl)-N,N,N',N'-tetramethyluronium hexafluorophosphate
HBr hydrobromic acid
HBTU O-benzotriazol-1-yl-N,N,N',N'-tetramethyluronium hexafluorophosphate
HCl hydrochloric acid
$H_2$ hydrogen
$H_2O$ water
$H_2O_2$ hydrogen peroxide
HOAc, AcOH acetic acid
HOBt 1-hydroxybenzotriazole hydrate
$K_2CO_3$ potassium carbonate
KOH potassium hydroxide
KH potassium hydride
LiHMDS lithium bis(trimethylsilyl)amide
NaHMDS sodium bis(trimethylsilyl)amide
LDA lithium diisopropylamide
MCPBA meta-chloroperbenzoic acid
MeCN, $CH_3CN$ acetonitrile
MeI methyl iodide
MeOH, $CH_3OH$ methanol
mL, ml milliliter
$N_2$ nitrogen
$NaBH_3CN$ sodium cyanoborohydride
NaCl sodium chloride
NaH sodium hydride
$NaHCO_3$ sodium bicarbonate
$NaH_2PO_4$ sodium biphosphate
NaI sodium iodide
NaO(t-Bu) sodium tert-butoxide
NaOH sodium hydroxide
$Na_2SO_4$ sodium sulfate
$NH_3$ ammonia
$NH_4Cl$ ammonium chloride
NMP N-methylpyrrolidinone
PBS phosphate buffered saline
$P(t-Bu)_3$ tri(tert-butyl)phosphine
Pd/C palladium on carbon
$Pd_2(dba)_3$ bis(dibenzylideneacetone) palladium
$Pd(dppf)Cl_2$ 1,1-bis(diphenylphosphino)ferrocene palladium chloride
$Pd(OAc)_2$ palladium acetate
$Pd(PPh_3)_4$ palladium tetrakis triphenylphosphine
PE petroleum ether (60-90° C.)
$POCl_3$ phosphorous oxychloride
PyBop benzotriazol-1-yl-oxytripyrrolidinophosphonium hexafluorophosphate
RT, rt, r.t. room temperature
Rt retention time
5 $nCl_4$ tin tetrachloride
TBAB tetrabutylammonium bromide
$TBAHSO_4$ tetrabutylammonium hydrogen sulfate
TBTU O-benzotriazol-1-yl-N,N,N',N'-tetramethyluronium tetrafluoroborate TFA trifluoroacetic acid
TEAC bis(tetra-ethylammonium)carbonate
THF tetrahydrofuran
μL microliters
$ZnCl_2$ zinc chloride Outlined in Schemes 1 to 8 are representative general procedures for preparing the compounds disclosed herein. Each $R_1$, $R_2$, and M represents appropriate groups as defined herein, wherein each $R_1$ is independently H or alkyl; each $R_2$ is independently H, alkyl, cycloalkyl, heterocyclyl, aryl, heteroaryl; M is alkali metal or alkaline earth metal; and n is 0, 1 or 2.

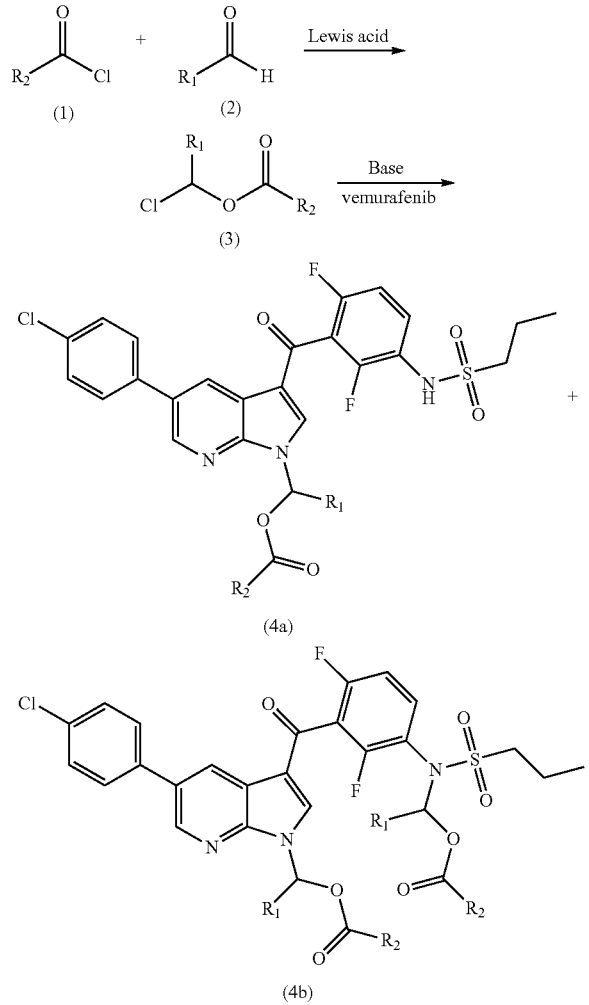

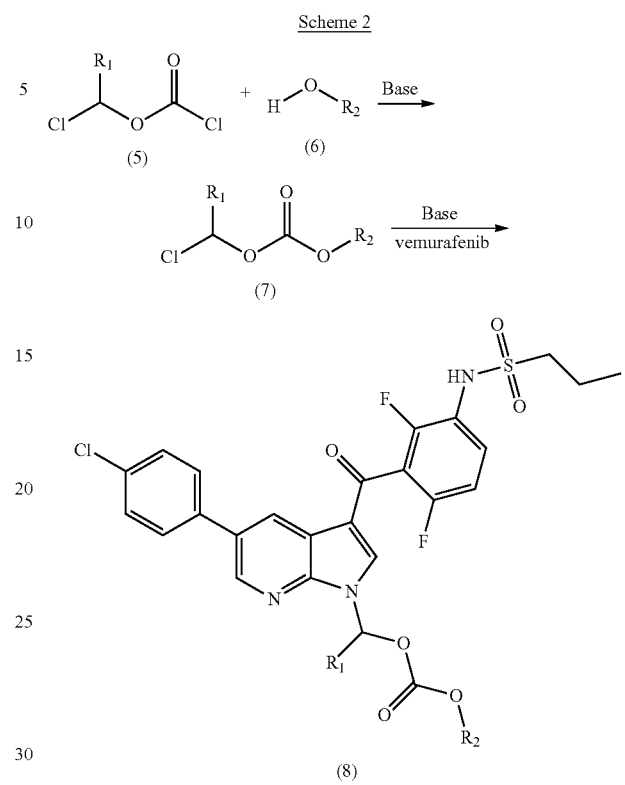

Some compounds having Formula (4a) or (4b) can be prepared by a general method illustrated in Scheme 1. Acid chloride (1) is reacted with an aldehyde (2) in the presence of a Lewis acid to furnish Chloroalkylester (3). Preferred Lewis acids include ZnCl$_2$, 5 nCl$_4$, BF$_3$-Et$_2$O, and others. The reaction is preferably run for between 30 min to 24 h neat or in an inert solvent such as DCM, CHCl$_3$, ClCH$_2$CH$_2$Cl, and others, at a temperature ranging from −40° C. to 40° C. Chloroalkylester (33) is then coupled with vemurafenib under basic conditions to give the substituted azaindole product (4a), (4b) or (4a) and (4b). Preferred bases for the coupling reaction include KOH, NaOH, NaH, KH, sodium hexamethyldisilazide, potassium hexamethyldisilazide, lithium diisopropylamide (LDA), 1,8-diazabicyclo[5.4.0]undec-7-ene (DBU), and others. The reaction is preferably run for a period in the range of 30 min to 24 h in an inert solvent such as DMF, DMSO, THF, dioxane, 1,2-dimethoxyethane (DME), and others, at a temperature ranging from −20° C. to 60° C.

Some compounds having Formula (8) can be prepared by a general method illustrated in Scheme 2. Chloroalkyl derived chloroformate (55) is reacted with alcohol (66) in the presence of a base to afford chloroalkyl carbonate (7). The preferred bases include pyridine, Et$_3$N, i-Pr$_2$NEt, 2,6-lutidine and others. The reaction is preferably performed in an inert solvent such as DCM, CHCl$_3$, ClCH$_2$CH$_2$Cl and others, at a temperature ranging from −15° C. to 40° C. Condensation of carbonate (77) with vemurafenib with the aid of a base provide desired compound (88). Preferred bases for the coupling reaction include Et$_3$N, KOH, NaOH, NaH, KH, sodium hexamethyldisilazide, potassium hexamethyldisilazide, lithium diisopropylamide (LDA), 1,8-diazabicyclo[5.4.0]undec-7-ene (DBU) and others. The reaction is preferably run for a period in the range of 30 min to 24 h in an inert solvent such as DMF, DMSO, THF, dioxane, 1,2-dimethoxyethane (DME), and others, at a temperature ranging from −20° C. to 40° C.

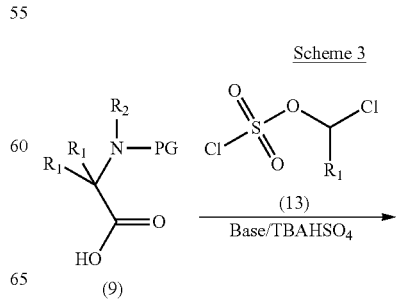

Scheme 4

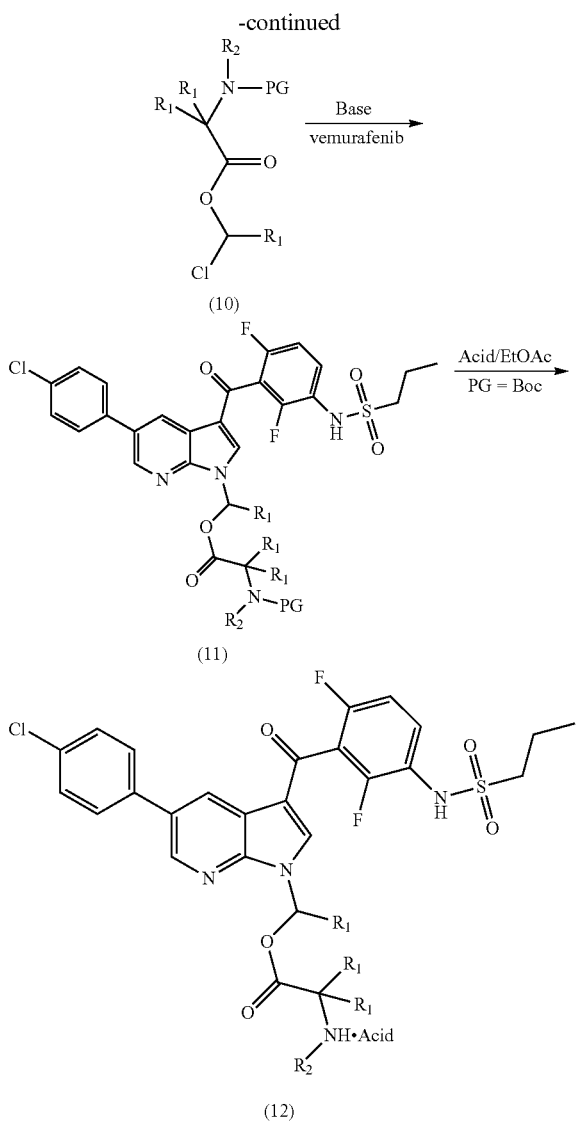

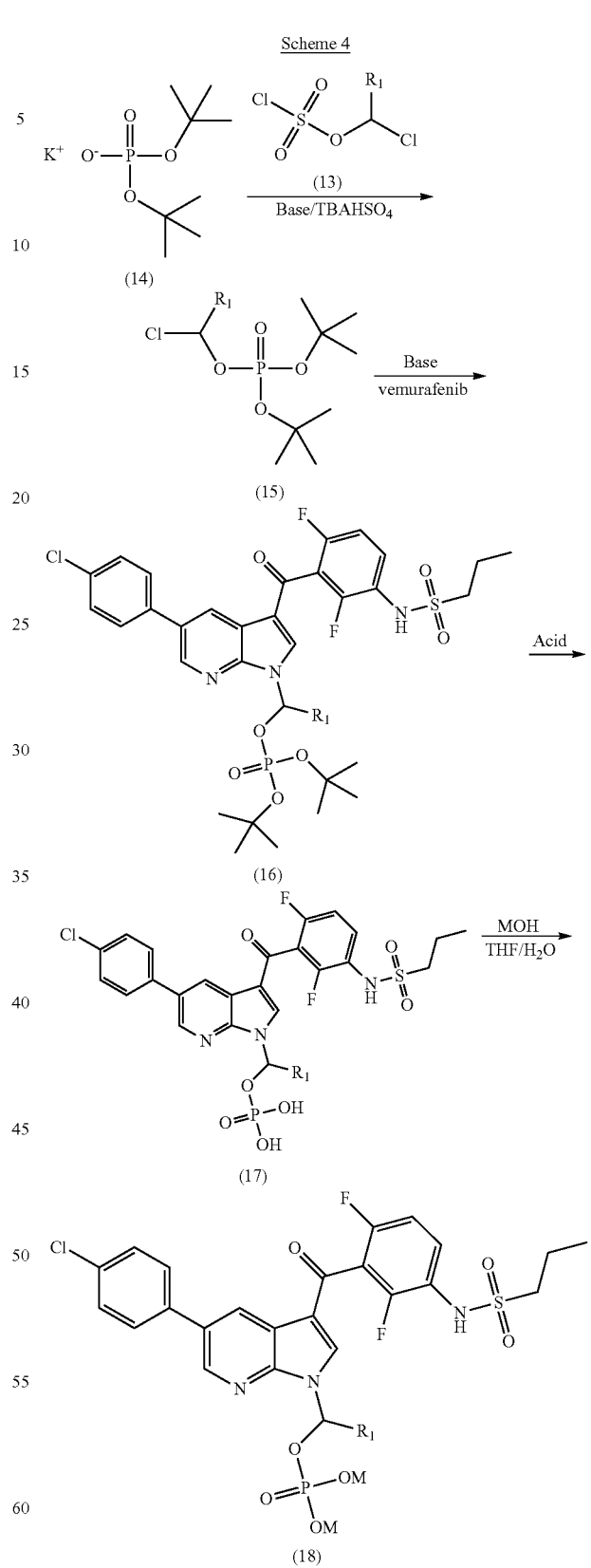

Some compounds having Formula (12) can be prepared by a general method illustrated in Scheme 3. Chloroalkyl derived sulfochloridate (13) is reacted with protected amino acid (9) in the presence of a base and a catalyst such as TBAHSO$_4$ to afford chloroalkyl ester (10). The preferred bases for the coupling reaction include NaHCO$_3$, KHCO$_3$, Na$_2$CO$_3$, K$_2$CO$_3$, Cs$_2$CO$_3$, Et$_3$N, i-Pr$_2$NEt, 2,6-lutidine, and others. The reaction is preferably performed in an inert solvent such as DCM, H$_2$O, CHCl$_3$, ClCH$_2$CH$_2$Cl, and others, at a temperature ranging from −20° C. to 40° C. Attachment of chloroalkyl ester (10) to vemurafenib is carried out under basic condition to provide protected aminoester (11). Preferred bases for the coupling reaction include KOH, NaOH, NaH or 1,8-diazabicyclo[5.4.0]undec-7-ene (DBU), and others. The reaction is preferably run for a period in the range of 30 min to 24 h in an inert solvent such as DMF, DMSO, THF, DCM, dioxane or 1,2-dimethoxyethane (DME) at a temperature ranging from −10° C. to 40° C. Amino-protecting groups include, but are not limited to, tert-butyloxycarbonyl (Boc), which may be removed under acidic conditions, for example by treatment with trifluoroacetic acid (TFA) in DCM, or HCl in ethyl acetate or ethyl ether.

Some compounds having Formula (17) or (1j) can be prepared by a general method illustrated in Scheme 4. Chloroalkyl derived sulfochloridate (13) is reacted with a suitably protected salt of a phosphoric acid diester derivative such as potassium di-tert-butyl phosphate (14) in the presence of a base and a catalyst such as TBAHSO$_4$ to afford chloroalkyl di-tert-butyl phosphate (15). The preferred bases for the coupling reaction include NaHCO$_3$, KHCO$_3$, Na$_2$CO$_3$, K$_2$CO$_3$, Cs$_2$CO$_3$, Et$_3$N, i-Pr$_2$NEt, 2,6-lutidine, and others. The reaction is preferably performed in an inert solvent such as DCM, H$_2$O, CHCl$_3$, ClCH$_2$CH$_2$Cl, and others, at a temperature ranging from −20° C. to 40° C. Attachment of haloalkyl di-tert-butyl phosphate (15) to vemurafenib is carried out under basic condition to provide di-tert-butyl phosphate derivative (16). Preferred bases for the coupling reaction include KOH, NaOH, NaH or 1,8-diazabicyclo[5.4.0]undec-7-ene (DBU) and others. The reaction is preferably run for a period in the range of 30 min to 24 h in an inert solvent such as DMF, DMSO, THF, dioxane or 1,2-dimethoxyethane (DME) at a temperature ranging from −10° C. to 40° C. Tert-Butyl protecting group in compound (16) may be removed under acidic conditions, for example by treatment with trifluoroacetic acid (TFA) in DCM or HCl in ethyl acetate or ethyl ether. The phosphoric acid (17) is treated with a suitable base such as NaOH or KOH in aqueous solution to furnish phosphate salt (18).

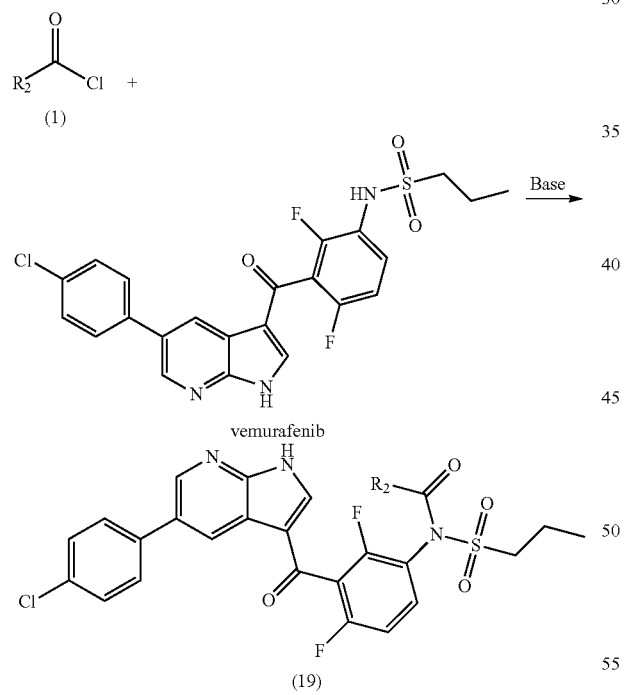

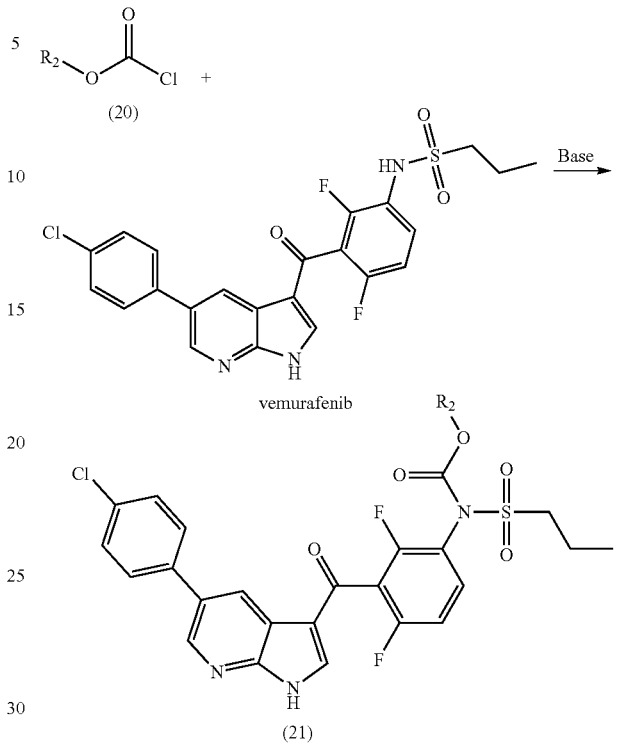

Some compounds having Formula (21) can be prepared by a general method illustrated in Scheme 6. Chloroformate (20) is coupled with vemurafenib under basic conditions to give the desired product (21). Preferred bases for the coupling reaction include KOH, NaOH, Et$_3$N, and others. The reaction is preferably run for a period in the range of 30 min to 24 h in an inert solvent such as DMF, DMSO, CHCl$_3$, THF, dioxane, DCM, and others, at a temperature ranging from −20° C. to 40° C.

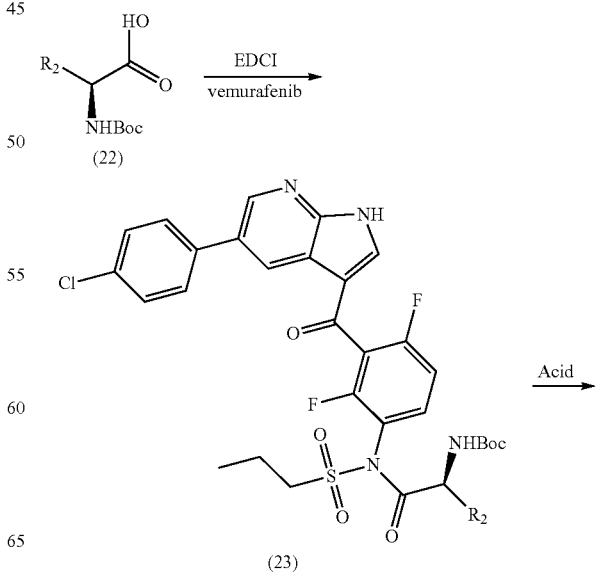

Some compounds having Formula (19) can be prepared by a general method illustrated in Scheme 5. Acid chloride (1) is coupled with vemurafenib under basic conditions to give the desired product (19). Preferred bases for the coupling reaction include KOH, NaOH, Et$_3$N, and others. The reaction is preferably run for a period in the range of 30 min to 24 h in an inert solvent such as DMF, DMSO, CHCl$_3$, THF, dioxane, DCM, and others, at a temperature ranging from −20° C. to 40° C.

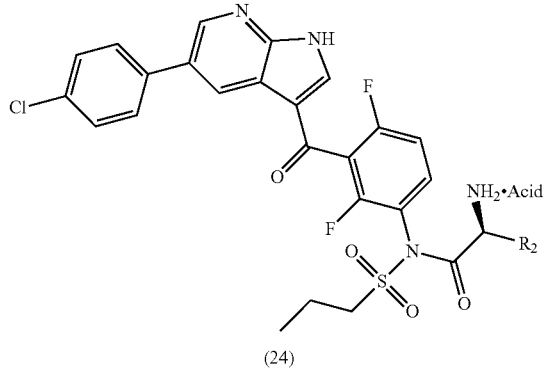

(24)

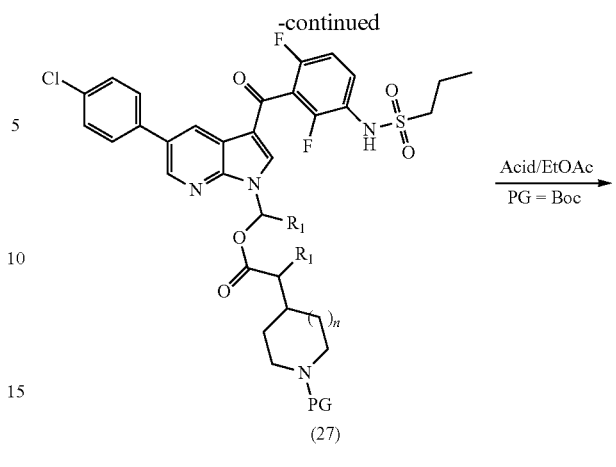

(27)

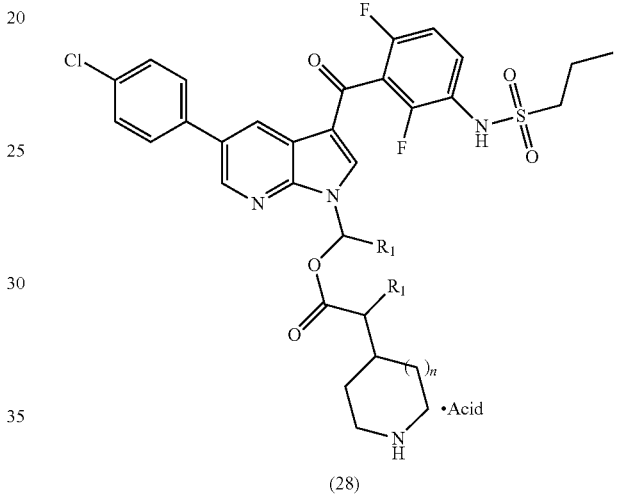

(28)

Some compounds having Formula (24) can be prepared by a general method illustrated in Scheme 7. Under basic conditions, chloroformate (22) is condensed with vemurafenib in the presence of a suitable catalyst such as EDCI to give the desired Boc-protected azaindole product (23). Preferred bases for the condensation reaction include Et$_3$N, 4-Phenylpyrimidine, and others. The reaction is preferably run for a period in the range of 30 min to 24 h in an inert solvent such as DMF, DME, dioxane, DCM, and others, at a temperature ranging from −10° C. to 40° C. Amino-protecting groups include, but are not limited to, tert-butyloxycarbonyl (Boc), which may be removed under acidic conditions, for example by treatment with trifluoroacetic acid (TFA) in DCM, or HCl in ethyl acetate or ethyl ether.

Scheme 8

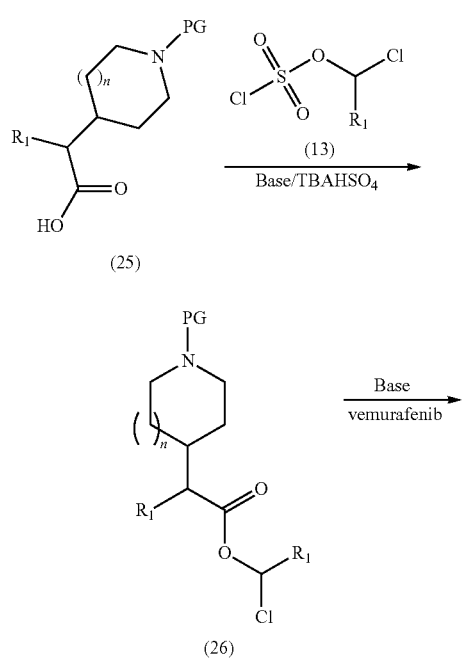

Some compounds having Formula (28) can be prepared by a general method illustrated in Scheme 8. Chloroalkyl derived sulfochloridate (13) is reacted with a amino-protected acid derivative (25) in the presence of a base and a catalyst such as TBAHSO$_4$ to afford chloroalkyl ester (26). The preferred bases for the coupling reaction include NaHCO$_3$, KHCO$_3$, Na$_2$CO$_3$, K$_2$CO$_3$, Cs$_2$CO$_3$, Et$_3$N, i-Pr$_2$NEt, 2,6-lutidine and others. The reaction is preferably performed in an inert solvent such as DCM, H$_2$O, CHCl$_3$, ClCH$_2$CH$_2$Cl and others, at a temperature ranging from −20° C. to 40° C. Attachment of the haloalkyl ester (L) to vemurafenib is carried out under basic condition to provide substituted azaindole compound (27). Preferred bases for the coupling reaction include KOH, NaOH, NaH or 1,8-diazabicyclo[5.4.0]undec-7-ene (DBU) and others. The reaction is preferably run for a period in the range of 30 min to 24 h in an inert solvent such as DMF, DMSO, THF, dioxane or 1,2-dimethoxyethane (DME) at a temperature ranging from −10° C. to 40° C. Tert-butyl protecting group in substituted azaindole compound (27) may be removed under acidic conditions, for example by treatment with trifluoroacetic acid (TFA) in DCM or HCl in ethyl acetate or ethyl ether.

EXAMPLES

Example 1 ethyl 3-(5-(4-chlorophenyl)-1H-pyrrolo[2,3-b]pyridine-3-carbonyl)-2,4-difluorophenyl(propylsulfonyl)carbamate

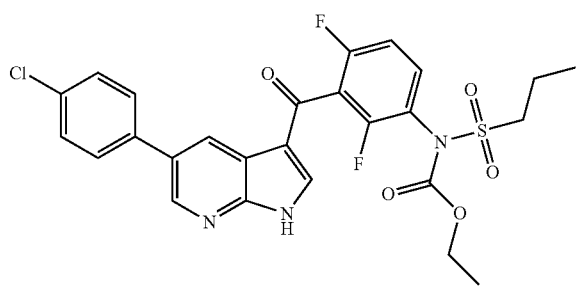 [SMILES: CCCS(=O)(=O)N(C(=O)OCC)c1ccc(F)c(C(=O)c2c[nH]c3ncc(-c4ccc(Cl)cc4)cc23)c1F]

To a suspension of N-(3-(5-(4-chlorophenyl)-1H-pyrrolo[2,3-b]pyridine-3-carbonyl)-2,4-difluorophenyl)-propane-1-sulfonamide (0.2 g, 0.41 mmol) in dioxane (15 mL) were added ethyl chloroformate (EtOCOCl, 44 mg, 0.41 mmol) and triethylamine (0.14 g, 1.38 mmol). The reaction was stirred at rt for 1.5 h, then concentrated in vacuo. The residue was purified by a silica gel column chromatography (hexane/EtOAc (v/v)=4/1) to afford the title compound as a white solid (0.12 g, 50%). The title compound was characterized by LC-MS and $^1$H NMR as shown below:

LC-MS (ESI, pos. ion) m/z 562.1 [M+H]$^+$;
$^1$H NMR (400 MHz, CDCl$_3$) δ 1.08 (t, J=7.2 Hz, 3H), 1.29 (t, J=7.2 Hz, 3H), 1.92-2.05 (m, 2H), 3.61 (br, 1H), 3.70 (br, 1H), 4.27-4.32 (q, J=7.2 Hz, 2H), 7.08-7.13 (m, 1H), 7.45-7.51 (m, 3H), 7.78 (d, J=8.4 Hz, 2H), 7.98 (d, J=2.0 Hz, 1H), 8.65 (d, J=1.9 Hz, 1H), 8.89 (d, J=2.0 Hz, 1H), 10.81 (s, 1H).

Example 2

N-(3-(5-(4-chlorophenyl)-1H-pyrrolo[2,3-b]pyridine-3-carbonyl)-2,4-difluorophenyl)-N-(propylsulfonyl)benzamide

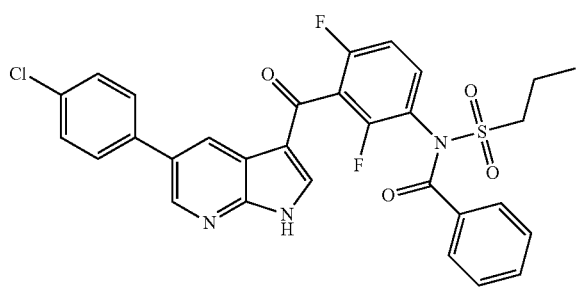 [SMILES: CCCS(=O)(=O)N(C(=O)c1ccccc1)c1ccc(F)c(C(=O)c2c[nH]c3ncc(-c4ccc(Cl)cc4)cc23)c1F]

To a suspension of N-(3-(5-(4-chlorophenyl)-1H-pyrrolo[2,3-b]pyridine-3-carbonyl)-2,4-difluorophenyl)-propane-1-sulfonamide (0.2 g, 0.41 mmol) in dioxane (15 mL) were added benzoyl chloride (57 mg, 0.41 mmol) and triethylamine (0.14 g, 1.38 mmol). The reaction was stirred at rt for 1 h, then concentrated in vacuo. The residue was purified by a silica gel column chromatography (hexane/EtOAc (v/v)=4/1) to afford the title compound as a white solid (0.14 g, 55%). The title compound was characterized by LC-MS and $^1$H NMR as shown below:

LC-MS (ESI, pos. ion) m/z 594.1 [M+H]$^+$;
$^1$H NMR (400 MHz, CDCl$_3$) δ 1.10 (t, J=7.4 Hz, 3H), 1.92-2.05 (m, 2H), 3.74 (t, J=7.6 Hz, 2H), 6.27-6.32 (q, J=7.2 Hz, 2H), 7.06-7.10 (m, 1H), 7.39 (t, J=7.6 Hz, 2H), 7.46-7.63 (m, 6H), 8.16 (d, J=7.0 Hz, 1H), 8.65 (d, J=2.1 Hz, 1H), 8.84 (d, J=2.0 Hz, 1H), 10.08 (s, 1H).

Example 3

N-(3-(5-(4-chlorophenyl)-1H-pyrrolo[2,3-b]pyridine-3-carbonyl)-2,4-difluorophenyl)-N-(propylsulfonyl)isobutyramide

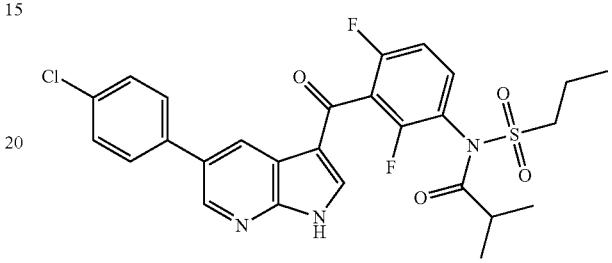

To a mixture of N-(3-(5-(4-chlorophenyl)-1H-pyrrolo[2,3-b]pyridine-3-carbonyl)-2,4-difluorophenyl)propane-1-sulfonamide (0.2 g, 0.41 mmol) and triethylamine (2 mL) in chloroform (10 mL) was added isobutyryl chloride (173 μA, 1.64 mmol) at rt. The reaction was stirred at rt for 16 h, then concentrated in vacuo. The residue was purified by a silica gel column chromatography (PE/EtOAc (v/v)=1/1 to 1/2) to afford the title compound as a white solid (2 mg, 0.8%). The title compound was characterized by LC-MS and $^1$H NMR as shown below:

LC-MS (ESI, pos. ion) m/z 560.1 [M+H]$^+$;
$^1$H NMR (400 MHz, CDCl$_3$) δ 1.04-1.15 (t, J=7.4 Hz, 3H), 1.12 (s, 3H), 1.13 (s, 3H), 1.88-1.99 (m, 2H), 2.46-2.54 (m, 1H), 3.55-3.80 (m, 2H), 7.14-7.20 (m, 1H), 7.46-7.55 (m, 3H), 7.60-7.45 (d, J=8.4 Hz, 2H), 7.77 (s, 1H), 8.64-8.68 (d, J=2.0 Hz, 1H), 8.86-8.90 (m, 1H), 10.20 (s, 1H).

Example 4

N-(3-(5-(4-chlorophenyl)-1H-pyrrolo[2,3-b]pyridine-3-carbonyl)-2,4-difluorophenyl)-N-(propylsulfonyl)acetamide

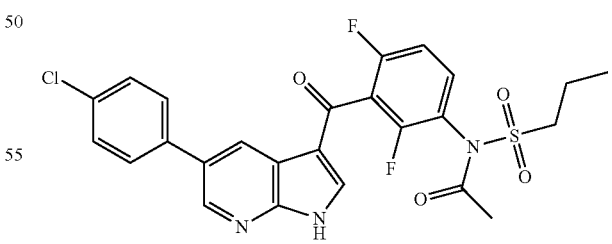

The title compound was prepared according to the procedure as described in Example 3 using N-(3-(5-(4-chlorophenyl)-1H-pyrrolo[2,3-b]pyridine-3-carbonyl)-2,4-difluorophenyl)propane-1-sulfonamide (0.2 g, 0.41 mmol), triethylamine (1 mL) and acetyl chloride (116 μL, 1.64 mmol) in 1,4-dioxane (10 mL). The title compound was obtained as a white solid (69 mg, 31.8%). The title compound was characterized by LCMS and $^1$H NMR as shown below:

LC-MS (ESI, pos. ion) m/z 532.1 [M+H]+;

1H NMR (400 MHz, CDCl3) δ 1.04-1.11 (t, J=7.4 Hz, 3H), 1.89-2.00 (m, 2H), 2.12 (s, 3H), 3.50-3.75 (m, 2H), 7.15-7.21 (m, 1H), 7.47-7.51 (m, 2H), 7.50-7.55 (m, 1H), 7.61-7.65 (m, 2H), 7.79 (s, 1H), 8.65-8.80 (d, J=2.1 Hz, 1H), 8.85-8.92 (m, 1H), 10.93 (s, 1H).

Example 5

N-(3-(5-(4-chlorophenyl)-1H-pyrrolo[2,3-b]pyridine-3-carbonyl)-2,4-difluorophenyl)-N-(propylsulfonyl)nicotinamide

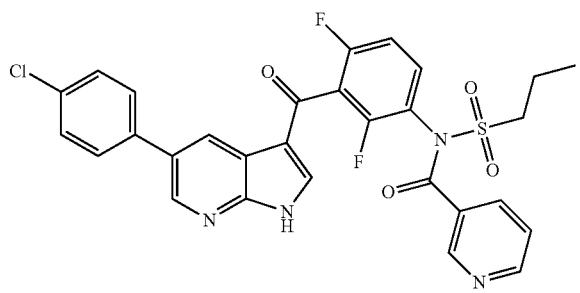 [SMILES: CCCS(=O)(=O)N(C(=O)c1cccnc1)c1ccc(F)c(C(=O)c2c[nH]c3ncc(-c4ccc(Cl)cc4)cc23)c1F]

The title compound was prepared according to the procedure as described in Example 3 using N-(3-(5-(4-chlorophenyl)-1H-pyrrolo[2,3-b]pyridine-3-carbonyl)-2,4-difluorophenyl)propane-1-sulfonamide (0.1 g, 0.2 mmol), triethylamine (228 µL, 1.6 mmol) and nicotinoyl chloride hydrochloride (146 mg, 0.2 mmol) in CHCl3 (10 mL). The crude product was purified by a silica gel column chromatography (PE/EtOAc (v/v)=2/1) to afford the title compound as a white solid (35 mg, 28.9%). The title compound was characterized by LC-MS and 1H NMR as shown below:

LC-MS (ESI, pos. ion) m/z 595.1 [M+H]+;

1H NMR (400 MHz, d6-DMSO) δ 1.02-1.08 (t, J=7.4 Hz, 3H), 1.83-1.93 (m, 2H), 3.86-3.93 (m, 2H), 7.37-7.44 (m, 1H), 7.44-7.50 (m, 1H), 7.55-7.60 (m, 2H), 7.74-7.82 (m, 2H), 7.96-8.04 (m, 1H), 8.25-8.29 (m, 1H), 8.59 (s, 1H), 8.64-8.67 (m, 1H), 8.72-8.75 (m, 1H), 8.77-8.80 (m, 1H), 9.06-9.09 (m, 1H), 13.11 (s, 1H).

Example 6

(S)-2-amino-N-(3-(5-(4-chlorophenyl)-1H-pyrrolo[2,3-b]pyridine-3-carbonyl)-2,4-difluorophenyl)-3-methyl-N-(propylsulfonyl)butanamide hydrochloride

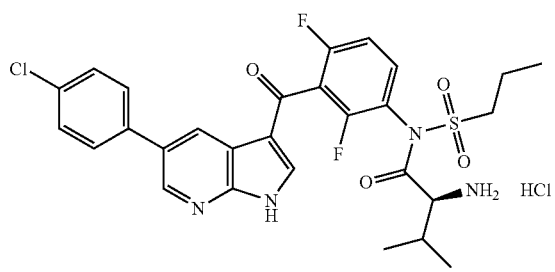 [SMILES: CCCS(=O)(=O)N(C(=O)[C@@H](N)C(C)C)c1ccc(F)c(C(=O)c2c[nH]c3ncc(-c4ccc(Cl)cc4)cc23)c1F ; Cl]

Step 1) (S)-tert-butyl (1-(N-(3-(5-(4-chlorophenyl)-1H-pyrrolo[2,3-b]pyridine-3-carbonyl)-2,4-difluorophenyl)propylsulfonamido)-3-methyl-1-oxobutan-2-yl)carbamate To a mixture of N-(3-(5-(4-chlorophenyl)-1H-pyrrolo[2,3-b]pyridine-3-carbonyl)-2,4-difluorophenyl)propane-1-sulfonamide (0.3 g, 0.61 mmol), (S)-2-(Boc-amino)-3-methylbutyric acid (0.28 g, 1.29 mmol) and 4-ppy (9 mg, 0.06 mmol) in DMF (2 mL) was added EDCI (234 mg, 1.23 mmol). The reaction was stirred at rt for 16 h, then diluted with EtOAc (30 mL) and washed with water (30 mL×3). The mixture was dried over Na2SO4 and concentrated in vacuo. The residue was purified by a silica gel column chromatography (PE/EtOAc (v/v)=3/1 to 2/1) to afford the title compound as a white solid (41 mg, 29.1%). The title compound was characterized by LC-MS as shown below:

LC-MS (ESI, neg. ion) m/z 686.6 [M−H]−.

Step 2) (S)-2-amino-N-(3-(5-(4-chlorophenyl)-1H-pyrrolo[2,3-b]pyridine-3-carbonyl)-2,4-difluorophenyl)-3-methyl-N-(propylsulfonyl)butanamide hydrochloride A mixture of (S)-tert-butyl (1-(N-(3-(5-(4-chlorophenyl)-1H-pyrrolo[2,3-b]pyridine-3-carbonyl)-2,4-difluorophenyl)propylsulfonamido)-3-methyl-1-oxobutan-2-yl)carbamate (50 mg, 0.07 mmol) and a saturated solution of HCl in EtOAc (2 mL) was stirred at rt for 2 h. The mixture was concentrated in vacuo to afford the title compound as a white solid (49 mg, 99%). The title compound was characterized by LC-MS as shown below:

LC-MS (ESI, pos. ion) m/z 589.2 [M+H]+.

Example 7

7a (5-(4-chlorophenyl)-3-(2,6-difluoro-3-(propylsulfonamido)benzoyl)-1H-pyrrolo[2,3-b]pyridin-1-yl)methyl pivalate 7b (N-(3-(5-(4-chlorophenyl)-1-((pivaloyloxy)methyl)-1H-pyrrolo[2,3-b]pyridine-3-carbonyl)-2,4-difluorophenyl)propylsulfonamido)methyl pivalate (7a)

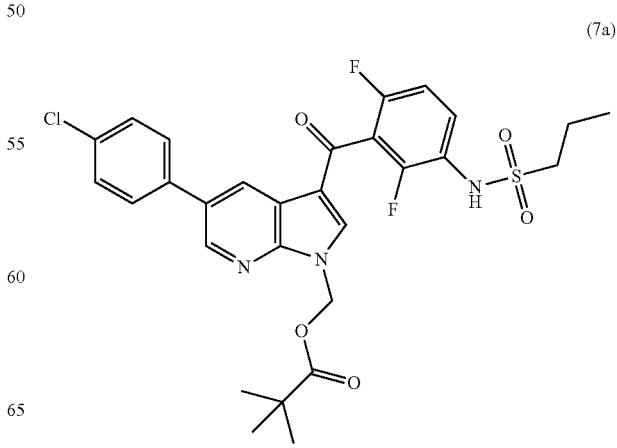

51

-continued

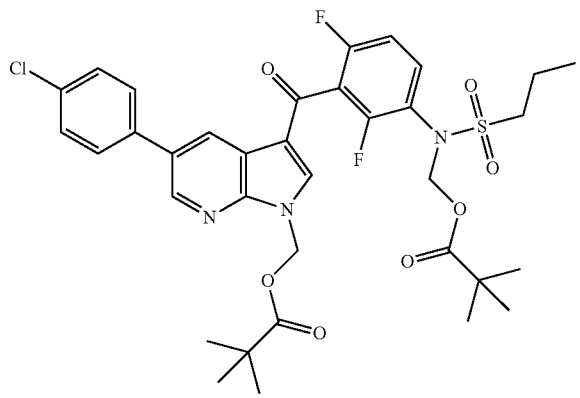

(7b)

To a mixture of N-(3-(5-(4-chlorophenyl)-1H-pyrrolo[2,3-b]pyridine-3-carbonyl)-2,4-difluorophenyl)propane-1-sulfonamide (0.1 g, 0.2 mmol) and Et$_3$N (57 μL, 0.41 mmol) in DMF (1 mL) was added chloromethyl pivalate (35 μL, 0.25 mmol) at rt. The reaction was stirred at rt for 24 h, then concentrated in vacuo. The residue was purified by a silica gel column chromatography (PE/EtOAc (v/v)=4/1 to 1/1) to afford (5-(4-chlorophenyl)-3-(2,6-difluoro-3-(propylsulfonamido)benzoyl)-1H-pyrrolo[2,3-b]pyridin-1-yl)methyl pivalate (30 mg, 23%) and (N-(3-(5-(4-chlorophenyl)-1-((pivaloyloxy)methyl)-1H-pyrrolo[2,3-b]pyridine-3-carbonyl)-2,4-difluorophenyl) propylsulfonamido) methyl pivalate (20 mg, 13.3%) as white solids. The title compounds were characterized by LC-MS and $^1$H NMR as shown below:

7a (5-(4-chlorophenyl)-3-(2,6-difluoro-3-(propylsulfonamido)benzoyl)-1H-pyrrolo[2,3-b]pyridin-1-yl) methyl pivalate LC-MS (ESI, pos. ion) m/z 604.1 [M+H]$^+$;

$^1$H NMR (400 MHz, CDCl$_3$) δ 1.04-1.10 (t, J=7.4 Hz, 3H), 1.16 (s, 9H), 1.86-1.96 (m, 2H), 3.10-3.16 (m, 2H), 6.27 (s, 2H), 6.58-6.65 (br, 1H), 7.04-7.10 (m, 1H), 7.46-7.51 (m, 2H), 7.59-7.63 (m, 2H), 7.69-7.77 (m, 1H), 7.84 (s, 1H), 8.67-8.70 (d, J=2.2 Hz, 1H), 8.84-8.87 (d, J=2.2 Hz, 1H).

7b (N-(3-(5-(4-chlorophenyl)-1-((pivaloyloxy)methyl)-1H-pyrrolo[2,3-b]pyridine-3-carbonyl)-2,4-difluorophenyl)propylsulfonamido)methyl pivalate LC-MS (ESI, pos. ion) m/z 718.2 [M+H]$^+$;

$^1$H NMR (400 MHz, CDCl$_3$) δ 1.02-1.08 (t, J=7.4 Hz, 3H), 1.15 (s, 9H), 1.18 (s, 9H), 1.87-1.97 (m, 2H), 5.65 (s, 2H), 6.28 (s, 2H), 7.06-7.12 (m, 1H), 7.45-7.50 (m, 2H), 7.54-7.60 (m, 1H), 7.59-7.64 (m, 2H), 7.92 (s, 1H), 8.66-8.69 (d, J=2.2 Hz, 1H), 8.84-8.87 (d, J=2.1 Hz, 1H).

52

Example 8

(N-(3-(1-(acetoxymethyl)-5-(4-chlorophenyl)-1H-pyrrolo[2,3-b]pyridine-3-carbonyl)-2,4-difluorophenyl)propylsulfonamido)methyl acetate

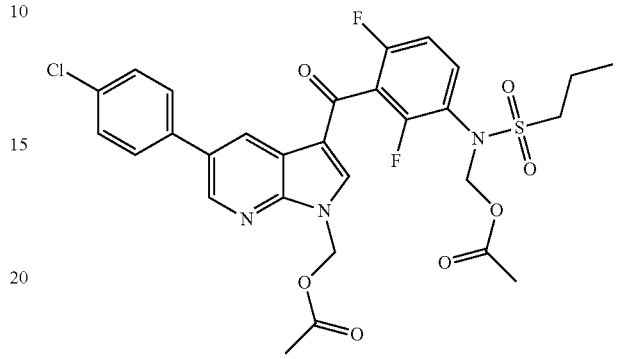

Step 1) chloromethyl acetate

To a mixture of acteyl chloride (10 mL, 94.6 mmol) and ZnCl$_2$ (25 mg, 186 mmol) was added paraformaldehyde (2.84 g, 94.6 mmol). The reaction was stirred at rt for 40 min. It was then heated to 60° C. and stirred further for 16 h. The mixture was cooled to rt and filtered through a short silica gel column (100% PE). The solution was concentrate in vacuo at 30° C. and the resulting oil was distilled at 60° C. under reduced pressure to give the title compound as colorless oil (2.34 g, 15.3%). The title compound was characterized by $^1$H NMR as shown below:

$^1$H NMR (400 MHz, CDCl$_3$) δ 1.18-1.23 (d, J=7.0 Hz, 6H), 2.56-2.68 (m, 1H), 5.72 (s, 2H).

Step 2) (N-(3-(1-(acetoxymethyl)-5-(4-chlorophenyl)-1H-pyrrolo[2,3-b]pyridine-3-carbonyl)-2,4-difluorophenyl)propylsulfonamido)methyl acetate To a mixture of N-(3-(5-(4-chlorophenyl)-1H-pyrrolo[2,3-b]pyridine-3-carbonyl)-2,4-difluorophenyl)propane-1-sulfonamide (0.1 g, 0.2 mmol) and Et$_3$N (57 μL, 0.4 mmol) in DMF (1 mL) was added chloromethyl acetate (23 μL, 0.3 mmol) at rt. The reaction was stirred at rt for 16 h, and then concentrated in vacuo. The residue was purified by a silica gel column chromatography (PE/EtOAc (v/v)=2/1 to 1/1) to afford the title compound as a white solid (52 mg, 40.3%). The title compound was characterized by LC-MS and $^1$H NMR as shown below:

LC-MS (ESI, pos. ion) m/z 634.1 [M+H]$^+$;

$^1$H NMR (400 MHz, CDCl$_3$) δ 1.03-1.09 (t, J=7.4 Hz, 3H), 2.07-2.12 (d, J=4.9 Hz, 2H), 3.13-3.17 (m, 2H), 5.64 (s, 2H), 6.28 (s, 2H), 7.07-7.13 (m, 1H), 7.46-7.51 (m, 2H), 7.56-7.64 (m, 3H), 7.93 (s, 1H), 8.67-8.70 (d, J=2.2 Hz, 1H), 8.85-8.88 (d, J=2.2 Hz, 1H).

Example 9

(5-(4-chlorophenyl)-3-(2,6-difluoro-3-(propylsulfonamido)benzoyl)-1H-pyrrolo[2,3-b]pyridin-1-yl) methyl isobutyrate

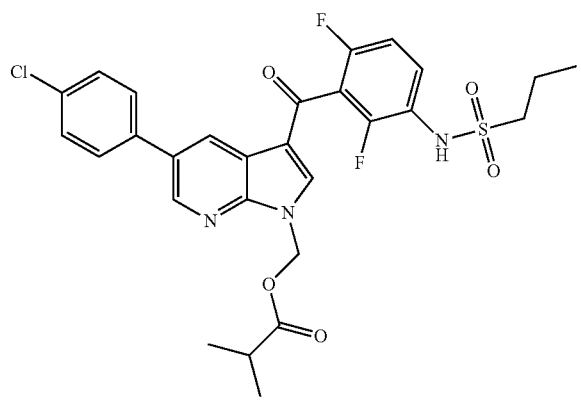 [SMILES: CCCS(=O)(=O)Nc1ccc(F)c(C(=O)c2cn(COC(=O)C(C)C)c3ncc(-c4ccc(Cl)cc4)cc23)c1F]

Step 1) chloromethyl isobutyrate

The title compound was prepared according to the procedure as described in Example 8 Step 1 using isobutyryl chloride (10 mL, 94.6 mmol), ZnCl$_2$ (25 mg, 186 mmol) and paraformaldehyde (2.84 g, 94.6 mmol). The title compound was obtained as colorless oil (5.52 g, 42.9%). The title compound was characterized by $^1$H NMR as shown below:

$^1$H NMR (400 MHz, CDCl$_3$) δ 1.18-1.23 (d, J=7.0 Hz, 6H), 2.56-2.68 (m, 1H), 5.72 (s, 2H).

Step 2) (5-(4-chlorophenyl)-3-(2,6-difluoro-3-(propylsulfonamido)benzoyl)-1H-pyrrolo[2,3-b]pyridin-1-yl)methyl isobutyrate To a mixture of N-(3-(5-(4-chlorophenyl)-1H-pyrrolo[2,3-b]pyridine-3-carbonyl)-2,4-difluorophenyl)propane-1-sulfonamide (0.1 g, 0.2 mmol) and Et$_3$N (57 μL, 0.4 mmol) in DMF (1 mL) was added chloromethyl isobutyrate (34 mg, 0.25 mmol) at rt. The reaction was stirred at rt for 16 h, then concentrated in vacuo. The residue was purified by a silica gel column chromatography (PE/EtOAc (v/v)=4/1 to 3/1) to afford the title compound as a white solid (45 mg, 37.5%). The title compound was characterized by LC-MS and $^1$H NMR as shown below:

LC-MS (ESI, pos. ion) m/z 590.1 [M+H]$^+$;

$^1$H NMR (400 MHz, CDCl$_3$) δ 1.04-1.10 (t, J=7.4 Hz, 3H), 1.85-1.96 (m, 2H), 2.54-2.62 (m, 1H), 3.09-3.15 (m, 2H), 6.27 (s, 2H), 6.51 (s, 1H), 7.04-7.10 (m, 1H), 7.46-7.51 (m, 2H), 7.58-7.63 (m, 2H), 7.70-7.77 (m, 1H), 7.84 (s, 1H), 8.67-8.70 (d, J=2.2 Hz, 1H), 8.85-8.88 (d, J=2.2 Hz, 1H).

Example 10

1-(5-(4-chlorophenyl)-3-(2,6-difluoro-3-(propylsulfonamido)benzoyl)-1H-pyrrolo[2,3-b]pyridin-1-yl) ethyl propionate

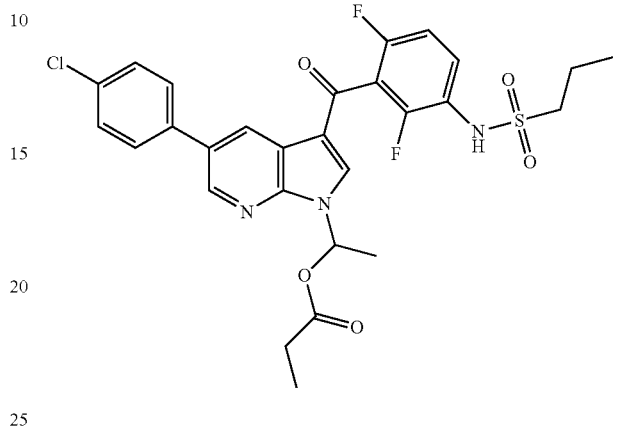

Step 1) 1-chloroethyl propionate

To a mixture of propionylchloride (10 mL, 114.56 mmol) and zinc (II) chloride (25 mg, 186 mmol) was added acetaldehyde (7.76 mL, 137.48 mmol) at 0° C. The reaction was stirred at rt for 16 h, and then filtered through a short silica gel column (100% PE). The solution was concentrated in vacuo at 20° C. and the resulting oil was distilled at 25-27° C. under reduced pressure to give the title compound as colorless oil (4.7 g, 30%). The title compound was characterized by $^1$H NMR as shown below:

$^1$H NMR (400 MHz, CDCl$_3$) δ 1.14-1.20 (t, J=7.6 Hz, 3H), 1.77-1.80 (d, J=5.8 Hz, 3H), 2.41 (q, J=7.6 Hz, 2H), 6.51-6.60 (q, J=5.8 Hz, 1H).

Step 2) 1-(5-(4-chlorophenyl)-3-(2,6-difluoro-3-(propylsulfonamido)benzoyl)-1H-pyrrolo[2,3-b]pyridin-1-yl)ethyl propionate To a solution of N-(3-(5-(4-chlorophenyl)-1H-pyrrolo[2,3-b]pyridine-3-carbonyl)-2,4-difluorophenyl)propane-1-sulfonamide (0.2 g, 0.41 mmol) in DMF (1 mL) was added Et$_3$N (165 mg, 1.64 mmol). The reaction was stirred at 10° C. for 10 min, followed by the dropwise addition of a solution of TBAB (264 mg, 1.64 mmol) in DMF (0.5 mL) and a solution of 1-chloroethyl propionate (67 mg, 0.41 mmol) in DMF (0.5 mL) over 30 min. The mixture was stirred at 10° C. for another 3 h, then diluted with EtOAc (40 mL) and filtered. The filtrate was concentrated in vacuo and the residue was purified by a silica gel column chromatography (PE/EtOAc (v/v)=4/1) to afford the title compound as a white solid (141 mg, 58%). The title compound was characterized by LCMS and $^1$H NMR as shown below:

LC-MS (ESI, neg. ion) m/z 588.3 [M−H]$^−$;

$^1$H NMR (400 MHz, CDCl$_3$) δ 1.00-1.17 (m, 6H), 1.85-2.00 (m, 5H), 2.26-2.41 (m, 2H), 3.08-3.17 (m, 2H), 6.50-6.80 (br, 1H), 7.03-7.12 (m, 1H), 7.35-7.42 (m, 1H), 7.42-

7.51 (d, J=8.2 Hz, 2H), 7.56-7.64 (d, J=8.4 Hz, 2H), 7.65-7.76 (m, 1H), 7.77 (s, 1H), 8.63-8.70 (m, 1H), 8.77-8.83 (m, 1H).

Example 11

1-(5-(4-chlorophenyl)-3-(2,6-difluoro-3-(propylsulfonamido)benzoyl)-1H-pyrrolo[2,3-b]pyridin-1-yl)-2-methylpropyl propionate

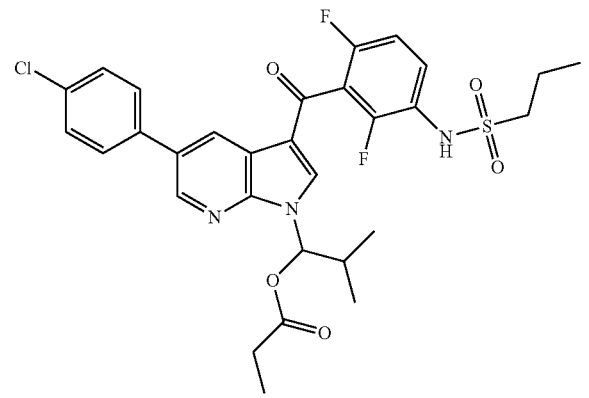 [SMILES: CCCS(=O)(=O)Nc1ccc(F)c(C(=O)c2cn(C(OC(=O)CC)C(C)C)c3ncc(-c4ccc(Cl)cc4)cc23)c1F]

Step 1) 1-chloro-2-methylpropyl propionate

To a mixture of propionyl chloride (10 mL, 115 mmol) and zinc (II) chloride (25 mg, 186 mmol) was added isobutyraldehyde (12.5 mL, 138 mmol) at −20° C. The reaction was stirred at 0° C. for 2 h, then at rt for another 16 h. The resulting mixture was filtered through a short silica gel column (100% PE). The solution was concentrated in vacuo at 40° C. and the resulted oil was distilled at 90° C. under reduced pressure to give the title compound as colorless oil (0.52 g, 2.7%). The title compound was characterized by $^1$H NMR as shown below:

$^1$H NMR (400 MHz, CDCl$_3$) δ 1.03-1.08 (m, 6H), 1.15-1.20 (t, J=7.5 Hz, 3H), 2.10-2.20 (m, 1H), 2.35-2.45 (q, J=7.6 Hz, 1H), 6.30-6.32 (d, J=4.7 Hz, 1H).

Step 2) 1-(5-(4-chlorophenyl)-3-(2,6-difluoro-3-(propylsulfonamido)benzoyl)-1H-pyrrolo[2,3-b]pyridin-1-yl)-2-methylpropyl propionate The title compound was prepared according to the procedure as described in Example 10 Step 2 using a solution of N-(3-(5-(4-chlorophenyl)-1H-pyrrolo[2,3-b]pyridine-3-carbonyl)-2,4-difluorophenyl)propane-1-sulfonamide (0.2 g, 0.4 mmol) in DMF (1 mL), KOH (46 mg, 0.80 mmol), a solution of TBAB (264 mg, 0.81 mmol) in DMF (0.5 mL) and a solution of 1-chloro-2-methylpropyl propionate (81 mg, 0.49 mmol) in DMF (0.5 mL). The title compound was obtained as a white solid (114 mg, 45%). The title compound was characterized by LC-MS and $^1$H NMR as shown below:

LC-MS (ESI, neg. ion) m/z 616.3 [M−H]$^−$;

$^1$H NMR (400 MHz, CDCl$_3$) δ 0.77-0.85 (d, J=6.8 Hz, 3H), 1.03-1.20 (m, 9H), 2.30-2.48 (m, 2H), 2.68-2.80 (m, 1H), 3.09-3.17 (m, 2H), 4.12-4.27 (m, 2H), 6.66 (br, 1H), 6.87-6.83 (d, J=9.2 Hz, 1H), 7.03-7.10 (m, 1H), 7.44-7.50 (d, J=8.4 Hz, 2H), 7.57-7.63 (d, J=8.4 Hz, 2H), 7.68-7.77 (m, 2H), 8.65-8.70 (d, J=2.0 Hz, 1H), 8.78-8.83 (m, 1H).

Example 12

1-(5-(4-chlorophenyl)-3-(2,6-difluoro-3-(propylsulfonamido)benzoyl)-1H-pyrrolo[2,3-b]pyridin-1-yl) ethyl pentanoate

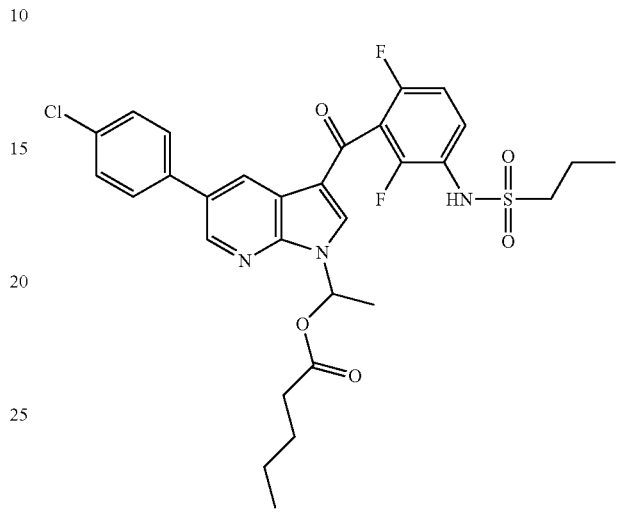

Step 1) 1-chloroethyl pentanoate

To a mixture of pentanoyl chloride (5 mL, 41.5 mmol) and zinc (II) chloride (25 mg, 186 mmol) was added acetaldehyde (2 mL, 49.5 mmol) at −20° C. The reaction was stirred at 0° C. for 1 h, then stirred further at rt for 2 h. The mxiture was filtered through a short silica gel column (100% PE). The solution was concentrated in vacuo at 40° C. and the resulting oil was distilled at 60° C. under reduced pressure to give the title compound as colorless oil (5.5 g, 81%). The title compound was characterized by $^1$H NMR and $^{13}$C NMR as shown below:

$^1$H NMR (400 MHz, CDCl$_3$) δ 0.90-0.94 (t, J=7.3 Hz, 3H), 1.32-1.40 (m, 2H), 1.58-1.65 (m, 2H), 1.77-1.79 (d, J=5.8 Hz, 3H), 2.33-2.37 (t, J=7.5 Hz, 2H), 6.52-6.57 (q, J=5.8 Hz, 1H);

$^{13}$C NMR (100 MHz, CDCl$_3$) δ 13.7, 22.2, 25.2, 26.7, 33.9, 80.6, 171.5.

Step 2) 1-(5-(4-chlorophenyl)-3-(2,6-difluoro-3-(propylsulfonamido)benzoyl)-1H-pyrrolo[2,3-b]pyridin-1-yl)ethyl pentanoate To a suspension of N-(3-(5-(4-chlorophenyl)-1H-pyrrolo[2,3-b]pyridine-3-carbonyl)-2,4-difluorophenyl)propane-1-sulfonamide (0.3 g, 0.61 mmol) in anhydrous DMF (2.5 mL) was added KOH (69 mg, 1.23 mmol). The reaction was stirred at 10° C. for 30 min, followed by adding a solution of 1-chloroethyl pentanoate (0.1 g, 0.61 mmol) in anhydrous DMF (0.5 mL) dropwise over 30 min. The mixture was stirred at 10° C. for another 16 h, then diluted with EtOAc (40 mL) and filtered. The filtrate was concentrated in vacuo and the residue was purified by a silica gel column chromatography (PE/EtOAc (v/v)=7/1) to give the crude product. The crude product was recrystallized in PE/EtOAc (10/1) to give the title compound as a white solid (0.14 g, 37.8%). The title compound was characterized by LC-MS and $^1$H NMR as shown below:

LC-MS (ESI, neg. ion) m/z 615.5 [M−H]⁻;
¹H NMR (400 MHz, CDCl₃) δ 0.83-0.87 (t, J=7.3 Hz, 3H), 1.04-1.08 (t, J=7.4 Hz, 3H), 1.24-1.30 (m, 2H), 1.53-1.59 (m, 2H), 1.86-1.92 (m, 2H), 1.92-1.94 (d, J=6.3 Hz, 3H), 2.29-2.34 (m, 2H), 3.10-3.14 (m, 2H), 6.53 (br, 1H), 7.05-7.10 (m, 1H), 7.35-7.40 (q, J=6.3 Hz, 1H), 7.46-7.48 (d, J=8.5 Hz, 2H), 7.58-7.60 (d, J=8.5 Hz, 2H), 7.68-7.74 (td, J=8.9, 5.5 Hz, 1H), 7.76 (s, 1H), 8.66-8.67 (d, J=2.1 Hz, 1H), 8.80-8.81 (d, J=2.0 Hz, 1H).

Example 13

1-(5-(4-chlorophenyl)-3-(2,6-difluoro-3-(propylsulfonamido)benzoyl)-1H-pyrrolo[2,3-b]pyridin-1-yl)ethyl cyclopentanecarboxylate

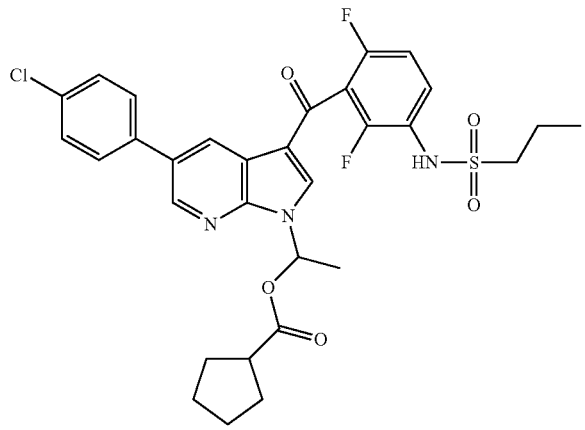 [SMILES: CCCS(=O)(=O)Nc1ccc(F)c(C(=O)c2cn(C(C)OC(=O)C3CCCC3)c3ncc(-c4ccc(Cl)cc4)cc23)c1F]

Step 1) 1-chloroethyl cyclopentanecarboxylate

To a mixture of cyclopentanecarbonyl chloride (5 g, 37.7 mmol) and zinc (II) chloride (25 mg, 186 mmol) was added acetaldehyde (1.83 g, 41.5 mmol) at −20° C. The reaction was stirred at 0° C. for 1 h, then at r.t for another 2 h. The resulting mixture was filtered through a short silica gel column (100% DCM). The solution was concentrated in vacuo at 40° C. and the resulted oil was distilled at 55° C. under reduced pressure to give the title compound as colorless oil (5.6 g, 85%). The title compound was characterized by ¹H NMR and ¹³C NMR as shown below:
¹H NMR (400 MHz, CDCl₃) δ 1.57-1.62 (m, 2H), 1.68-1.72 (m, 2H), 1.78-1.79 (d, J=5.8 Hz, 3H), 1.80-1.93 (m, 4H), 2.69-2.80 (m, 1H), 6.52-6.57 (q, J=5.8 Hz, 1H);
¹³C NMR (100 MHz, CDCl₃) δ 25.2, 25.9, 29.9, 30.0, 43.8, 80.8, 183.5.

Step 2) 1-(5-(4-chlorophenyl)-3-(2,6-difluoro-3-(propylsulfonamido)benzoyl)-1H-pyrrolo[2,3-b]pyridin-1-yl)ethyl cyclopentanecarboxylate The title compound was prepared according to the procedure as described in Example 12 Step 2 using N-(3-(5-(4-chlorophenyl)-1H-pyrrolo[2,3-b]pyridine-3-carbonyl)-2,4-difluorophenyl)propane-1-sulfonamide (0.3 g, 0.61 mmol) in anhydrous DMF (2.5 mL), KOH (69 mg, 1.23 mmol) and a solution of 1-chloroethyl cyclopentanecarboxylate (108 mg, 0.61 mmol) in anhydrous DMF (0.5 mL). The curde product was purified by a silica gel column chromatography (PE/ EtOAc (v/v)=5/1) and recrystallized in PE to give the title compound as a white solid (147 mg, 38%). The title compound was characterized by LC-MS and ¹H NMR as shown below:
LC-MS (ESI, neg. ion) m/z 627.5 [M−H]⁻;
¹H NMR (400 MHz, CDCl₃) δ 1.04-1.08 (t, J=7.4 Hz, 3H), 1.23-1.29 (m, 2H), 1.29-1.33 (m, 2H), 1.61-1.66 (m, 2H), 1.77-1.81 (m, 2H), 1.86-1.89 (m, 2H), 1.90-1.92 (d, J=6.2 Hz, 3H), 2.71-2.75 (m, 1H), 3.10-3.14 (m, 2H), 6.47 (br, 1H), 7.05-7.10 (m, 1H), 7.35-7.40 (q, J=6.3 Hz, 1H), 7.46-7.48 (d, J=8.5 Hz, 2H), 7.58-7.60 (d, J=8.4 Hz, 2H), 7.70-7.74 (td, J=9.0, 5.5 Hz, 1H), 7.75 (s, 1H), 8.66-8.67 (d, J=2.1 Hz, 1H), 8.80-8.81 (d, J=2.1 Hz, 1H).

Example 14

1-(5-(4-chlorophenyl)-3-(2,6-difluoro-3-(propylsulfonamido)benzoyl)-1H-pyrrolo[2,3-b]pyridin-1-yl)ethyl isobutyrate

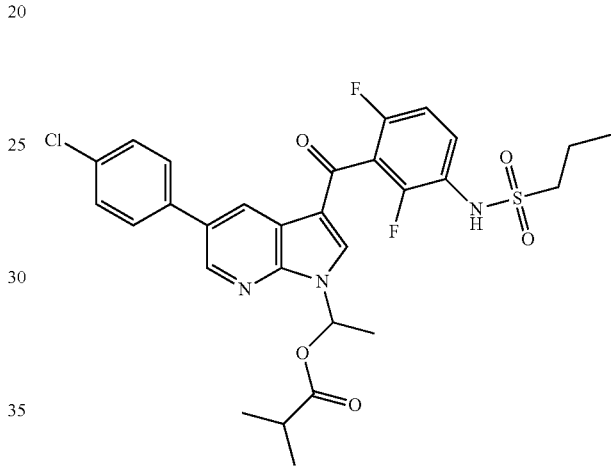

Step 1) 1-chloroethyl isobutyrate

To a mixture of isobutyryl chloride (10 mL, 94.7 mmol) and zinc (II) chloride (25 mg, 186 mmol) was added acetaldehyde (5 g, 113.6 mmol) at −20° C. The reaction was stirred at 0° C. for 16 h, then at rt for another 2 h. The mixture was filtered through a short silica gel column (100% PE). The solution was concentrated in vacuoat 30° C. and the resulting oil was distilled at 65° C. under reduced pressure to give the title compound as colorless oil (2.64 g, 18.5%). The title compound was characterized by ¹H NMR as shown below:
¹H NMR (400 MHz, CDCl₃) δ 1.15-1.25 (m, 6H), 1.77-1.82 (d, J=5.8 Hz, 3H), 2.50-2.63 (m, 1H), 6.50-6.60 (q, J=5.8 Hz, 1H).

Step 2) 1-(5-(4-chlorophenyl)-3-(2,6-difluoro-3-(propylsulfonamido)benzoyl)-1H-pyrrolo[2,3-b]pyridin-1-yl)ethyl isobutyrate To a mixture of N-(3-(5-(4-chlorophenyl)-1H-pyrrolo[2,3-b]pyridine-3-carbonyl)-2,4-difluorophenyl)propane-1-sulfonamide (0.5 g, 1.02 mmol) and potassium hydroxide (115 mg, 2.04 mmol) in anhydrous DMF (4 mL) was added a solution of chloromethyl isobutyrate (37 mg, 0.25 mmol) in anhydrous DMF (1 mL) over 30 min at 10° C. The reaction was stirred at 10° C. for 3 h, then diluted with EtOAc (40 mL) and filtered. The filtrate was concentrated in vacuo and the residue was purified by a silica gel column chromatography (PE/EtOAc (v/v)=5/1 to 4/1) to afford the title compound as a white solid (0.39 g, 63.3%). The title compound was characterized by LC-MS and $^1$H NMR as shown below:

LC-MS (ESI, pos. ion) m/z 626.0 [M+Na]$^+$;

$^1$H NMR (400 MHz, CDCl$_3$) δ 1.03-1.12 (m, 6H), 1.13-1.20 (d, J=7.0 Hz, 3H), 1.85-1.97 (m, 5H), 2.50-2.60 (m, 1H), 3.09-3.17 (m, 2H), 6.55 (s, 1H), 7.04-7.10 (m, 1H), 7.35-7.42 (m, 1H), 7.46-7.51 (d, J=8.4 Hz, 2H), 7.57-7.63 (d, J=8.4 Hz, 2H), 7.68-7.75 (m, 1H), 7.76 (s, 1H), 8.67-8.70 (d, J=2.1 Hz, 1H), 8.78-8.84 (d, J=1.8 Hz, 1H).

Example 15

(5-(4-chlorophenyl)-3-(2,6-difluoro-3-(propylsulfonamido)benzoyl)-1H-pyrrolo[2,3-b]pyridin-1-yl) methyl propionate

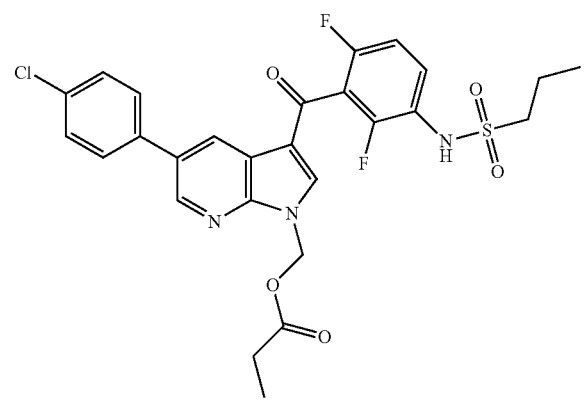 [SMILES: CCCS(=O)(=O)Nc1ccc(F)c(C(=O)c2cn(COC(=O)CC)c3ncc(-c4ccc(Cl)cc4)cc23)c1F]

Step 1) chloromethyl propionate

To a mixture of paraformaldehyde (3.37 g, 112.3 mmol) and zinc (II) chloride (25 mg, 186 mmol) was added propionyl chloride (10 mL, 112.3 mmol). The reaction was stirred at rt for 40 min, then heated to 60° C. and stirred further for 16 h. The mixture was cooled to rt and filtered through a short silica gel column (100% PE). The solvent was removed in vacuo at 20° C. and the resulting oil was distilled at 40° C. under reduced pressure to give the title compound as colorless oil (9.8 g, 70%). The title compound was characterized by $^1$H NMR as shown below:

$^1$H NMR (400 MHz, CDCl$_3$) δ 1.16-1.19 (d, J=7.56 Hz, 3H), 2.39-2.45 (t, J=7.56 Hz, 2H), 5.71 (s, 2H).

Step 2) (5-(4-chlorophenyl)-3-(2,6-difluoro-3-(propylsulfonamido)benzoyl)-1H-pyrrolo[2,3-b]pyridin-1-yl)methyl propionate The title compound was prepared according to the procedure as described in Example 14 Step 2 using N-(3-(5-(4-chlorophenyl)-1H-pyrrolo[2,3-b]pyridine-3-carbonyl)-2,4-difluorophenyl)propane-1-sulfonamide (0.3 g, 0.61 mmol) in anhydrous DMF (2.5 mL), KOH (69 mg, 1.23 mmol) and a solution of chloromethyl propionate (75 mg, 0.61 mmol) in anhydrous DMF (0.5 mL). The crude product was purified by a silica gel column chromatography (PE/EtOAc (v/v)=4/1), and recrystallized in methanol to afford the title compound as a white solid (145 mg, 41.4%). The title compound was characterized by LC-MS and $^1$H NMR as shown below:

LC-MS (ESI, neg. ion) m/z 574.1 [M−H]$^−$;

$^1$H NMR (400 MHz, CDCl$_3$) δ 1.04-1.08 (t, J=7.4 Hz, 3H), 1.09-1.13 (t, J=7.5 Hz, 3H), 1.87-1.93 (m, 2H), 2.34-2.40 (d, J=7.5 Hz, 2H), 3.09-3.13 (m, 2H), 6.27 (s, 2H), 6.63 (br, 1H), 7.04-7.09 (m, 1H), 7.45-7.49 (m, 2H), 7.58-7.61 (m, 2H), 7.70-7.75 (td, J=5.5, 9.0 Hz, 1H), 7.85 (s, 1H), 8.67-8.68 (d, J=2.2 Hz, 1H), 8.84-8.85 (d, J=2.1 Hz, 1H).

Example 16

1-(5-(4-chlorophenyl)-3-(2,6-difluoro-3-(propylsulfonamido)benzoyl)-1H-pyrrolo[2,3-b]pyridin-1-yl)-2-methylpropyl isobutyrate

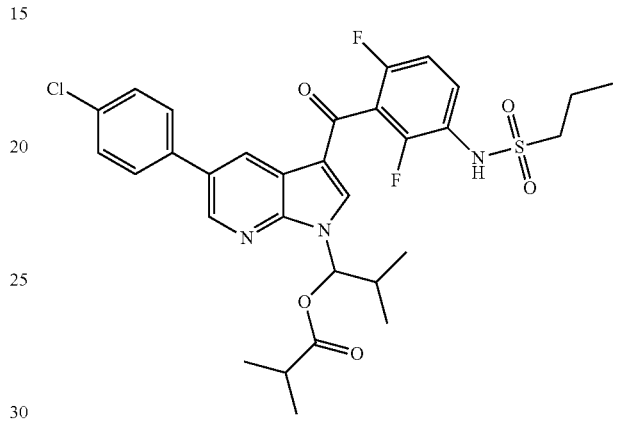

Step 1) 1-chloro-2-methylpropyl isobutyrate

To a mixture of isobutyryl chloride (10 mL, 94.7 mmol) and zinc (II) chloride (25 mg, 186 mmol) was added isobutyraldehyde (10.4 mL, 113.6 mmol) at −20° C. The reaction was stirred at 0° C. for 1 h, then at rt for another 2 h. The mixture was filtered through a short silica gel column (100% PE). The solution was concentrated in vacuo at 40° C. and the resulted oil was distilled at 75° C. under reduced pressure to give the title compound as colorless oil (13.48 g, 79.3%). The title compound was characterized by $^1$H NMR as shown below:

$^1$H NMR (400 MHz, CDCl$_3$) δ 1.04-1.08 (dd, J=3.68, 3.08 Hz, 6H), 1.19-1.22 (d, J=7.04 Hz, 6H), 2.12-2.21 (m, 1H), 2.57-2.65 (m, J=7.04 Hz, 1H), 6.29-6.31 (d, J=4.72 Hz, 1H).

Step 2) 1-(5-(4-chlorophenyl)-3-(2,6-difluoro-3-(propylsulfonamido)benzoyl)-1H-pyrrolo[2,3-b]pyridin-1-yl)-2-methylpropyl isobutyrate The title compound was prepared according to the procedure as described in Example 14 Step 2 using N-(3-(5-(4-chlorophenyl)-1H-pyrrolo[2,3-b]pyridine-3-carbonyl)-2,4-difluorophenyl)propane-1-sulfonamide (0.3 g, 0.61 mmol) in anhydrous DMF (2.5 mL), KOH (69 mg, 1.23 mmol) and a solution of 1-chloro-2-methylpropyl isobutyrate (108 mg, 0.61 mmol) in anhydrous DMF (0.5 mL). The crude product was purified by a silica gel column chromatography (PE/EtOAc (v/v)=4/1), and recrystallized in methanol to afford the title compound as a white solid (47 mg, 13.4%). The title compound was characterized by LC-MS and $^1$H NMR as shown below:

LC-MS (ESI, neg. ion) m/z 629.5 [M−H]$^−$;

$^1$H NMR (400 MHz, CDCl$_3$) δ 1.04-1.08 (t, J=7.4 Hz, 3H), 1.08-1.12 (m, 6H), 1.86-1.95 (m, 2H), 2.54-2.61 (m, 1H), 3.09-3.14 (m, 2H), 6.27 (s, 2H), 6.67 (br, 1H), 7.04-7.09 (m, 1H), 7.46-7.49 (m, 2H), 7.59-7.61 (m, 2H), 7.70-7.75 (td, J=5.5, 9.0 Hz, 1H), 7.85 (s, 1H), 8.67-8.68 (d, J=2.1 Hz, 1H), 8.84-8.85 (d, J=2.1 Hz, 1H).

Example 17

(5-(4-chlorophenyl)-3-(2,6-difluoro-3-(propylsulfonamido)benzoyl)-1H-pyrrolo[2,3-b]pyridin-1-yl) methyl 2-(piperidin-4-yl)acetate hydrochloride

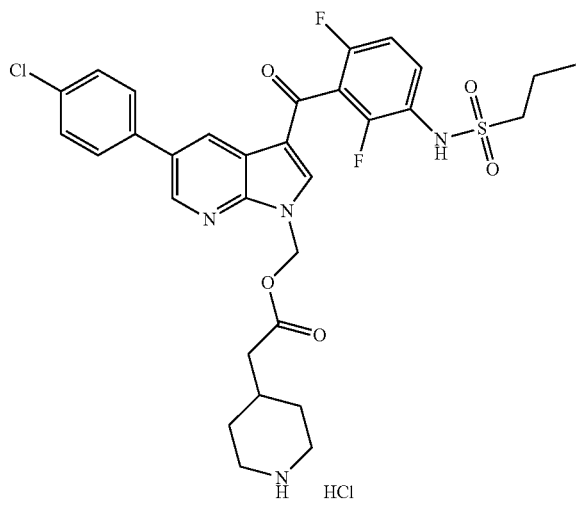 [SMILES: CCCS(=O)(=O)Nc1ccc(F)c(C(=O)c2cn(COC(=O)CC3CCNCC3)c3ncc(-c4ccc(Cl)cc4)cc23)c1F ; Cl]

Step 1) tert-butyl 4-(2-(chloromethoxy)-2-oxoethyl) piperidine-1-carboxylate

To a solution of 2-(1-(tert-butoxycarbonyl)piperidin-4-yl) acetic acid (1 g, 4.1 mmol) in DCM (25 mL) and H$_2$O (25 mL) were added NaHCO$_3$ (1.38 g, 16.4 mmol) and TBAHSO$_4$ (0.14 g, 0.41 mmol). The reaction was stirred at 0° C. for 10 min, followed by the addition of a solution of chloromethyl sulfochloridate (499 μL, 5.5 mmol) in DCM (5 mL). The mixture was stirred at rt for 20 h, then washed with brine (25 mL). The organic phase was dried over anhydrous Na$_2$SO$_4$ and concentrated in vacuo. The residue was purified by a silica gel column chromatography (PE/EtOAc (v/v)=10/1) to give the title compound as colorless oil (826 mg, 69.1%). The title compound was characterized by $^1$H NMR as shown below:

$^1$H NMR (400 MHz, CDCl$_3$) δ 1.11-1.24 (m, 2H), 1.65-1.74 (m, 2H), 1.90-2.03 (m, 1H), 2.30-2.35 (d, J=7.1 Hz, 2H), 2.66-2.70 (m, 2H), 4.00-4.16 (m, 2H), 5.71 (s, 2H).

Step 2) tert-butyl 4-(2-(5-(4-chlorophenyl)-3-(2,6-difluoro-3-(propylsulfonamido)benzoyl)-1H-pyrrolo [2,3-b]pyridin-1-yl)methoxy)-2-oxoethyl)piperidine-1-carboxylate The title compound was prepared according to the procedure as described in Example 14 Step 2 using N-(3-(5-(4-chlorophenyl)-1H-pyrrolo[2,3-b]pyridine-3-carbonyl)-2,4-difluorophenyl)propane-1-sulfonamide (0.1 g, 0.2 mmol) in DMF (0.9 mL), KOH (23 mg, 0.4 mmol) and a solution of tert-butyl 4-(2-(chloromethoxy)-2-oxoethyl)piperidine-1-carboxylate (60 mg, 0.2 mmol) in DMF (100 μL). The crude product was purified by a silica gel column chromatography (PE/EtOAc (v/v)=3/1 to 2/1) to afford the title compound as a white solid (86 mg, 56.6%). The title compound was characterized by LC-MS and $^1$H NMR as shown below:

LC-MS (ESI, neg. ion) m/z 742.4 [M−H]$^-$;

$^1$H NMR (400 MHz, CDCl$_3$) δ 1.02-1.15 (m, 5H), 1.43 (s, 9H), 1.52-1.60 (m, 2H), 1.70-1.87 (m, 3H), 2.26-2.30 (d, J=7.0 Hz, 2H), 2.58-2.70 (m, 2H), 3.10-3.15 (m, 2H), 3.96-4.06 (m, 2H), 6.28 (s, 2H), 7.03-7.10 (m, 1H), 7.46-7.50 (m, 2H), 7.58-7.64 (m, 2H), 7.69-7.77 (m, 1H), 7.83 (s, 1H), 8.66-8.70 (d, J=2.2 Hz, 1H), 8.84-8.87 (d, J=2.2 Hz, 1H).

Step 3) (5-(4-chlorophenyl)-3-(2,6-difluoro-3-(propylsulfonamido)benzoyl)-1H-pyrrolo[2,3-b]pyridin-1-yl)methyl 2-(piperidin-4-yl)acetate hydrochloride A mixture of tert-butyl 4-(2-(5-(4-chlorophenyl)-3-(2,6-difluoro-3-(propylsulfonamido)benzoyl)-1H-pyrrolo[2,3-b] pyridin-1-yl)methoxy)-2-oxoethyl) piperidine-1-carboxylate (78 mg, 0.1 mmol) and a saturated solution of HCl in EtOAc (2 mL) was stirred at rt for 2 h. The mixture was concentrated in vacuo to afford the title compound as a white solid (75 mg, 100%). The title compound was characterized by LCMS and $^1$H NMR as shown below:

LC-MS (ESI, pos. ion) m/z 645.2 [M+H]$^+$;

$^1$H NMR (400 MHz, d$_6$-DMSO) δ 0.96-1.00 (t, J=7.4 Hz, 3H), 1.30-1.40 (m, 2H), 1.71-1.80 (m, 4H), 1.87-1.97 (m, 1H), 2.30-2.35 (d, J=7.0 Hz, 2H), 2.75-2.87 (m, 2H), 3.13-3.22 (m, 4H), 6.31 (s, 2H), 7.31-7.38 (m, 1H), 7.58-7.70 (m, 3H), 7.79-7.85 (m, 2H), 8.48 (s, 1H), 8.67-8.70 (m, 2H), 8.80-8.82 (d, J=2.2 Hz, 1H), 9.84 (s, 1H).

Example 18

(5-(4-chlorophenyl)-3-(2,6-difluoro-3-(propylsulfonamido)benzoyl)-1H-pyrrolo[2,3-b]pyridin-1-yl) methyl 2-amino-3-methylbutanoate hydrochloride

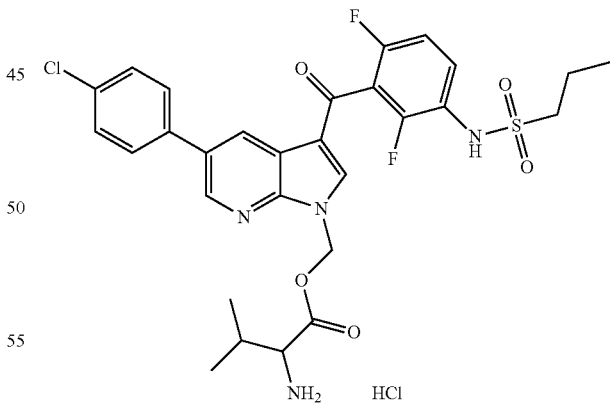

Step 1) chloromethyl 2-((tert-butoxycarbonyl)amino)-3-methylbutanoate

The title compound was prepared according to the procedure as described in Example 17 Step 1 using 2-((tert-butoxycarbonyl)amino)-3-methylbutanoic acid (1 g, 4.6 mmol) in DCM (25 mL) and H$_2$O (25 mL), NaHCO$_3$ (1.55 g, 18.4 mmol), TBAHSO₄ (156 mg, 0.46 mmol) and a solution of chloromethyl sulfochloridate (559 μL, 5.5 mmol) in DCM (5 mL). The title compound was obtained as colorless oil (877 mg, 71.8%). The title compound was characterized by ¹H NMR as shown below:

¹H NMR (400 MHz, CDCl₃) δ 0.92-0.94 (d, J=6.9 Hz, 3H), 0.99-1.01 (d, J=6.9 Hz, 3H), 1.45 (s, 9H), 2.17-2.23 (m, 1H), 4.25-4.29 (m, 1H), 5.02-5.04 (d, J=8.3 Hz, 1H), 5.62-5.64 (d, J=6.0 Hz, 2H), 5.87-5.89 (d, J=6.0 Hz, 1H).

Step 2) ((tert-butoxycarbonyl)amino)-3-methylbutanoate carbon 1 amino-3-methylbutanoate The title compound was prepared according to the procedure as described in Example 14 Step 2 using N-(3-(5-(4-chlorophenyl)-1H-pyrrolo[2,3-b]pyridine-3-carbonyl)-2,4-difluorophenyl)propane-1-sulfonamide (0.1 g, 0.2 mmol) in DMF (0.9 mL), KOH (23 mg, 0.4 mmol), a solution of chloromethyl 2-((tert-butoxycarbonyl)amino)-3-methylbutanoate (54 mg, 0.2 mmol) in DMF (100 μL). The title compound was purified by a silica gel column chromatography (PE/EtOAc (v/v)=4/1 to 3/1) and was obtained as a white solid (82 mg, 55.8%). The title compound was characterized by LC-MS and ¹H NMR as shown below:

LC-MS (ESI, neg. ion) m/z 716.5 [M−H]⁻;

¹H NMR (400 MHz, CDCl₃) δ 0.70-0.77 (d, J=6.7 Hz, 3H), 0.81-0.85 (d, J=6.5 Hz, 3H), 1.03-1.10 (t, J=7.4 Hz, 3H), 1.39 (s, 9H), 1.85-1.96 (m, 2H), 1.98-2.10 (m, 1H), 3.09-3.15 (m, 2H), 4.17-4.23 (m, 1H), 4.89-4.95 (m, 1H), 6.26-6.40 (dd, J=10.6 Hz, 35.8 Hz, 2H), 6.75 (br, 1H), 7.03-7.10 (m, 1H), 7.46-7.51 (m, 2H), 7.58-7.64 (m, 2H), 7.70-7.77 (m, 1H), 7.83 (s, 1H), 8.66-8.70 (d, J=2.2 Hz, 1H), 8.84-8.87 (d, J=2.1 Hz, 1H).

Step 3) (5-(4-chlorophenyl)-3-(2,6-difluoro-3-(propylsulfonamido)benzoyl)-1H-pyrrolo[2,3-b]pyridin-1-yl)methyl 2-amino-3-methylbutanoate hydrochloride The title compound was prepared according to the procedure as described in Example 17 Step 3 using (5-(4-chlorophenyl)-3-(2,6-difluoro-3-(propylsulfonamido)benzoyl)-1H-pyrrolo[2,3-b]pyridin-1-yl)methyl2-((tert-butoxycarbonyl)amino)-3-methyl butanoate (78 mg, 0.11 mmol) and a saturated solution of HCl in EtOAc (2 mL). The title compound was obtained as a white solid (40 mg, 54%). The title compound was characterized by LC-MS and ¹H NMR as shown below:

LC-MS (ESI, pos. ion) m/z 619.2 [M+H]⁺;

¹H NMR (400 MHz, d₆-DMSO) δ 0.80-0.90 (t, J=6.9 Hz, 6H), 0.95-1.01 (d, J=7.4 Hz, 3H), 1.71-1.82 (m, 2H), 2.05-2.15 (m, 1H), 3.12-3.20 (m, 2H), 3.94-3.98 (d, J=4.5 Hz, 1H), 6.40-6.57 (dd, J=10.6, 35.4 Hz, 2H), 7.30-7.39 (m, 1H), 7.58-7.70 (m, 3H), 7.78-7.87 (d, J=8.5 Hz, 2H), 8.53 (s, 2H), 8.68 (s, 1H), 8.79-8.85 (d, J=2.1 Hz, 1H).

Example 19

(5-(4-chlorophenyl)-3-(2,6-difluoro-3-(propylsulfonamido)benzoyl)-1H-pyrrolo[2,3-b]pyridin-1-yl) methyl 2-aminoacetate hydrochloride

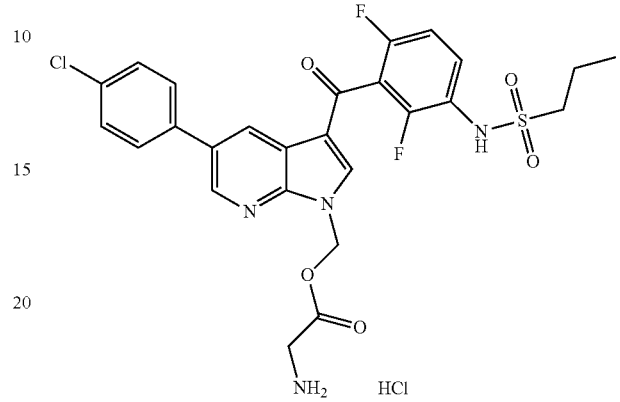

Step 1) chloromethyl 2-((tert-butoxycarbonyl)amino)acetate

The title compound was prepared according to the procedure as described in Example 17 Step 1 using 2-((tert-butoxycarbonyl)amino)acetic acid (1 g, 5.7 mmol) in DCM (25 mL) and H₂O (25 mL), NaHCO₃ (1.92 g, 22.8 mmol), TBAHSO₄ (194 mg, 0.57 mmol) and a solution of chloromethyl sulfochloridate (693 mL, 6.8 mmol) in DCM (5 mL). The title compound was obtained as colorless oil (911 mg, 71.3%).

Step 2) (5-(4-chlorophenyl)-3-(2,6-difluoro-3-(propylsulfonamido)benzoyl)-1H-pyrrolo[2,3-b]-pyridin-1-yl-butoxycarbonyl)amino)acetate The title compound was prepared according to the procedure as described in Example 14 Step 2 using N-(3-(5-(4-chlorophenyl)-1H-pyrrolo[2,3-b]pyridine-3-carbonyl)-2,4-difluorophenyl)propane-1-sulfonamide (0.1 g, 0.2 mmol) in DMF (0.9 mL), KOH (23 mg, 0.4 mmol), a solution of chloromethyl 2-((tert-butoxycarbonyl)amino)acetate (46 mg, 0.2 mmol) in DMF (100 mL). The title compound was purified by a silica gel column chromatography (PE/EtOAc (v/v)=4/1 to 3/1) and was obtained as a white solid (46 mg, 33.3%). The title compound was characterized by LC-MS and ¹H NMR as shown below:
LC-MS (ESI, pos. ion) m/z 677.1 [M+H]⁺;

¹H NMR (400 MHz, d₆-DMSO) δ 1.00-1.06 (t, J=7.4 Hz, 3H), 1.34 (s, 9H), 1.77-1.87 (m, 2H), 3.17-3.24 (m, 2H), 3.72-3.77 (d, J=6.1 Hz, 2H), 6.38 (s, 2H), 7.26-7.32 (t, J=6.1 Hz, 1H), 7.35-7.42 (m, 1H), 7.63-7.73 (m, 3H), 7.85-7.90 (d, J=8.6 Hz, 2H), 8.55 (s, 1H), 8.73 (s, 1H), 8.85-8.88 (d, J=2.2 Hz, 1H), 9.85-9.90 (br, 1H).

Step 3) (5-(4-chlorophenyl)-3-(2,6-difluoro-3-(propylsulfonamido)benzoyl)-1H-pyrrolo[2,3-b]pyridin-1-yl)methyl 2-aminoacetate hydrochloride The title compound was prepared according to the procedure as described in Example 17 Step 3 using (5-(4-chlorophenyl)-3-(2,6-difluoro-3-(propylsulfonamido)benzoyl)-

1H-pyrrolo[2,3-b]pyridin-1-yl)methyl 2-((tert-butoxycarbonyl)amino)acetate (46 mg, 0.07 mmol) and a saturated solution of HCl in EtOAc (2 mL). The title compound was obtained as a white solid (36 mg, 83.7%). The title compound was characterized by LC-MS and $^1$H NMR as shown below:

LC-MS (ESI, pos. ion) m/z 577.1 [M+H]$^+$;

$^1$H NMR (400 MHz, d$_6$-DMSO) δ 0.95-1.00 (d, J=7.4 Hz, 3H), 1.70-1.80 (m, 2H), 3.12-3.18 (m, 2H), 3.85 (s, 1H), 6.44 (s, 2H), 7.30-7.37 (m, 1H), 7.58-7.72 (m, 3H), 7.79-7.84 (m, 2H), 8.50-8.82 (m, 2H), 8.51 (s, 1H), 8.66 (s, 1H), 8.80-8.82 (d, J=2.2 Hz, 1H), 9.84 (s, 1H).

Example 20

(5-(4-chlorophenyl)-3-(2,6-difluoro-3-(propylsulfonamido)benzoyl)-1H-pyrrolo[2,3-b]pyridin-1-yl)methyl 2-(methylamino)acetate hydrochloride

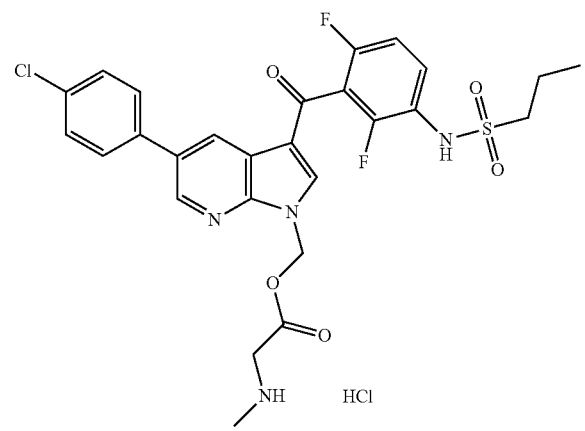 [SMILES: CCCS(=O)(=O)Nc1ccc(F)c(C(=O)c2cn(COC(=O)CNC)c3ncc(-c4ccc(Cl)cc4)cc23)c1F ; Cl]

Step 1 chloromethyl 2-((tert-butoxycarbonyl)methyl)amino acetate

The title compound was prepared according to the procedure as described in Example 17 Step 1 using 2-((tert-butoxycarbonyl)(methyl)amino)acetic acid (1 g, 5.29 mmol) in DCM (25 mL) and H$_2$O (25 mL), NaHCO$_3$ (1.78 g, 21.2 mmol), TBAHSO$_4$ (0.18 g, 0.53 mmol) and a solution of chloromethyl sulfochloridate (638 μL, 6.35 mmol) in DCM (5 mL). The title compound was obtained as colorless oil (0.87 g, 69.4%).

$^1$H NMR (400 MHz, CDCl$_3$) δ 1.43 (s, 9H), 2.94-2.96 (d, J=5.0 Hz, 1H), 3.97-4.05 (d, J=33.9 Hz, 2H), 5.74-5.75 (d, J=4.0 Hz, 1H).

Step 2) ((tert-butoxycarbonyl)(carbonylmethyl)amino acetate

The title compound was prepared according to the procedure as described in Example 14 Step 2 using N-(3-(5-(4-chlorophenyl)-1H-pyrrolo[2,3-b]pyridine-3-carbonyl)-2,4-difluorophenyl)propane-1-sulfonamide (0.3 g, 0.61 mmol) in DMF (2.5 mL), KOH (69 mg, 1.23 mmol), a solution of chloromethyl 2-((tert-butoxycarbonyl)(methyl)amino)acetate (145 mg, 0.61 mmol) in DMF (0.5 mL). The crude product was purified by a silica gel column chromatography (PE/EtOAc (v/v)=2/1) to afford the title compound as colorless oil (0.33 g, 77.9%). The title compound was characterized by LC-MS and $^1$H NMR as shown below:

LC-MS (ESI, neg. ion) m/z 689.4 [M–H]$^-$;

$^1$H NMR (400 MHz, CDCl$_3$) δ 0.88-0.94 (t, J=7.1 Hz, 3H), 1.43 (s, 9H), 1.89-1.91 (m, 2H), 2.89 (s, 3H), 3.08-3.13 (m, 2H), 3.91-4.00 (d, J=32.7 Hz, 2H), 6.33 (s, 2H), 6.78 (br, 1H), 7.03-7.10 (m, 1H), 7.47-7.50 (m, 2H), 7.59-7.62 (m, 2H), 7.70-7.75 (m, 1H), 7.82-7.86 (m, 1H), 8.66-8.68 (d, J=1.6 Hz, 1H), 8.85-8.87 (d, J=1.6 Hz, 1H).

Step 3) (5-(4-chlorophenyl)-3-(2,6-difluoro-3-(propylsulfonamido)benzoyl)-1H-pyrrolo[2,3-b]pyridin-1-yl)methyl 2-(methylamino)acetate hydrochloride A mixture of (5-(4-chlorophenyl)-3-(2,6-difluoro-3-(propylsulfonamido)benzoyl)-1H-pyrrolo[2,3-b]pyridin-1-yl)methyl 2-((tert-butoxycarbonyl)(methyl)amino)acetate (0.33 g, 0.48 mmol) and a saturated solution of HCl in EtOAc (3 mL) was stirred at rt for 3 h. The mixture was filtered to afford the title compound as a white solid (168 mg, 56%). The title compound was characterized by LCMS and $^1$H NMR as shown below:

LC-MS (ESI, pos. ion) m/z 591.1 [M+H]$^+$;

LC-MS (ESI, neg. ion) m/z 588.5 [M–H]$^-$;

$^1$H NMR (400 MHz, d$_6$-DMSO) δ 0.96-1.00 (t, J=7.4 Hz, 3H), 1.73-1.79 (m, 2H), 2.49-2.51 (m, 3H), 3.13-3.17 (m, 2H), 4.02 (s, 2H), 6.45 (s, 2H), 7.32-7.36 (m, 1H), 7.59-7.62 (dd, J=2.0, 6.6 Hz, 2H), 7.62-7.67 (m, 1H), 7.80-7.83 (dd, J=2.0, 6.6 Hz, 2H), 8.51 (s, 1H), 8.67 (br, 1H), 8.80-8.81 (d, J=2.2 Hz, 1H), 8.99 (br, 1H).

Example 21

(5-(4-chlorophenyl)-3-(2,6-difluoro-3-(propylsulfonamido)benzoyl)-1H-pyrrolo[2,3-b]pyridin-1-yl)methyl 2-amino-2-methylpropanoate hydrochloride

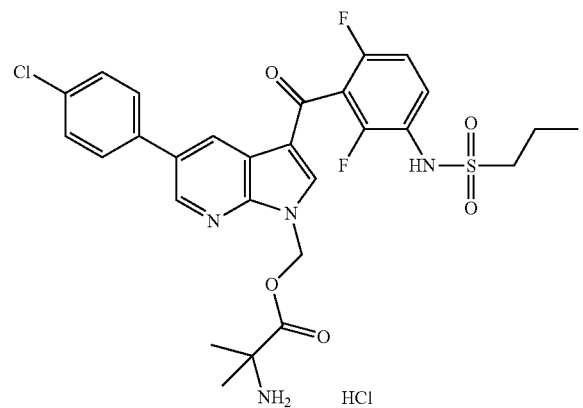 [SMILES: CCCS(=O)(=O)Nc1ccc(F)c(C(=O)c2cn(COC(=O)C(C)(C)N)c3ncc(-c4ccc(Cl)cc4)cc23)c1F ; Cl]

Step 1) chloromethyl 2-((tert-butoxycarbonyl)amino)-2-methylpropanoate

The title compound was prepared according to the procedure as described in Example 17 Step 1 using 2-((tert-butoxy carbonyl)amino)-2-methylpropanoic acid (1.07 g, 5.29 mmol) in DCM (25 mL) and H₂O (25 mL), NaHCO₃ (1.78 g, 21.2 mmol), TBAHSO₄ (0.18 g, 0.53 mmol) and a solution of chloromethyl sulfochloridate (638 μL, 6.35 mmol) in DCM (5 mL). The title compound was obtained as a white solid (1.16 g, 87.7%). The title compound was characterized by ¹H NMR as shown below:

¹H NMR (400 MHz, CDCl₃) δ 1.43 (s, 9H), 1.51 (s, 6H), 4.90 (m, 1H), 5.74-5.75 (d, J=4.0 Hz, 1H).

Step 2) (5-(4-chlorophenyl)-3-(2,6-difluoro-3-(propylsulfonamido)benzoyl)-1H-pyrrolo[2,3-b]pyridin-1-yl)methyl 2-((tert-butoxycarbonyl)amino)-2-methylpropanoate The title compound was prepared according to the procedure as described in Example 14 Step 2 using N-(3-(5-(4-chlorophenyl)-1H-pyrrolo[2,3-b]pyridine-3-carbonyl)-2,4-difluorophenyl)propane-1-sulfonamide (0.3 g, 0.61 mmol) in DMF (2.5 mL), KOH (69 mg, 0.4 mmol), and a solution of chloromethyl 2-((tert-butoxycarbonyl)amino)-2-methylpropanoate (158 mg, 0.61 mmol) in DMF (0.5 mL). The title compound was purified by a silica gel columnchromatography (PE/EtOAc (v/v)=4/1 to 3/1) and was obtained as a white solid (339 mg, 78.7%). The title compound was characterized by LC-MS and ¹H NMR as shown below:

LC-MS (ESI, pos. ion) m/z 705.2 [M+H]⁺;

¹H NMR (400 MHz, CDCl₃) δ 1.02-1.06 (t, J=7.4 Hz, 3H), 1.21 (s, 9H), 1.41 (s, 6H), 1.85-1.92 (m, 2H), 2.89 (s, 3H), 3.07-3.12 (m, 2H), 4.93 (br, 1H), 6.31 (s, 2H), 7.01-7.05 (m, 1H), 7.45-7.49 (m, 2H), 7.57-7.61 (m, 2H), 7.67-7.73 (m, 1H), 7.87 (s, 1H), 8.64-8.65 (d, J=2.2 Hz, 1H), 8.83-8.84 (d, J=2.2 Hz, 1H).

Step 3) (5-(4-chlorophenyl)-3-(2,6-difluoro-3-(propylsulfonamido)benzoyl)-1H-pyrrolo[2,3-b]pyridin-1-yl)methyl 2-amino-2-methylpropanoate hydrochloride A mixture of (5-(4-chlorophenyl)-3-(2,6-difluoro-3-(propylsulfonamido)benzoyl)-1H-pyrrolo[2,3-b]pyridin-1-yl) methyl 2-((tert-butoxycarbonyl)amino)-2-methylpropanoate (339 mg, 0.48 mmol) and a saturated solution of HCl in EtOAc (3 mL) was stirred at rt for 5 h. The resulting mixture was filtered to afford the title compound as a white solid (224 mg, 72.6%). The title compound was characterized by LC-MS and ¹H NMR as shown below:

LC-MS (ESI, pos. ion) m/z 605.2 [M+H]⁺;

LC-MS (ESI, neg. ion) m/z 603.3 [M−H]⁻;

¹H NMR (400 MHz, d₆-DMSO) δ 0.95-0.99 (t, J=7.4 Hz, 3H), 1.40 (s, 6H), 1.73-1.79 (m, 2H), 3.12-3.16 (m, 2H), 6.44 (s, 2H), 7.32-7.36 (m, 1H), 7.59-7.61 (dd, J=2.0 Hz, 6.6 Hz, 2H), 7.62-7.67 (m, 1H), 7.80-7.83 (dd, J=2.0, 6.6 Hz, 2H), 8.48 (br, 2H), 8.52 (s, 1H), 8.67 (br, 1H), 8.79-8.80 (d, J=2.2 Hz, 1H).

Example 22

(2S)-(5-(4-chlorophenyl)-3-(2,6-difluoro-3-(propylsulfonamido)benzoyl)-1H-pyrrolo[2,3-b]pyridin-1-yl)methyl-2-amino-3-methylpentanoate hydrochloride

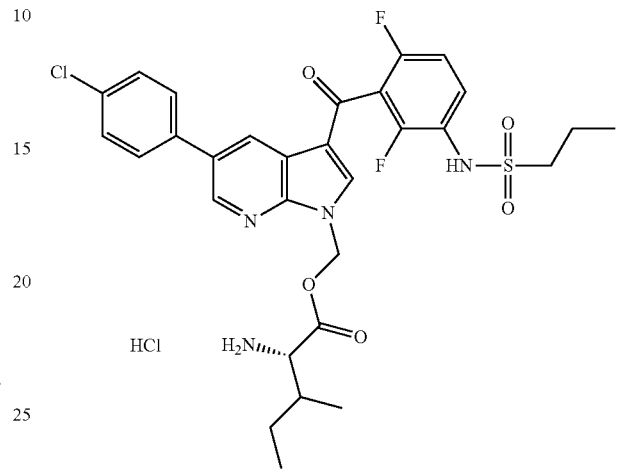

Step 1) (2S)-chloromethyl 2-((tert-butoxycarbonyl)amino)-3-methylpentanoate

The title compound was prepared according to the procedure as described in Example 17 Step 1 using L-2-((tert-butoxycarbonyl)amino)-3-methylpentanoic acid (1 g, 4.31 mmol) in DCM (25 mL) and H₂O (25 mL), NaHCO₃ (1.55 g, 18.4 mmol), TBAHSO₄ (156 mg, 0.46 mmol) and a solution of chloromethyl sulfochloridate (559 μL, 5.5 mmol) in DCM (5 mL). The title compound was obtained as colorless oil (0.91 g, 76.1%). The title compound was characterized by ¹H NMR as shown below:

¹H NMR (400 MHz, CDCl₃) δ 0.91-0.95 (t, J=7.4 Hz, 3H), 0.96-0.98 (d, J=6.9 Hz, 3H), 1.24-1.29 (m, 2H), 1.44 (s, 9H), 1.87-1.93 (m, 1H), 4.29-4.33 (m, 1H), 4.97-5.00 (m, 1H), 5.61-5.63 (d, J=6.0 Hz, 1H), 5.87-5.89 (d, J=6.0 Hz, 1H).

Step 2) (2S)-(5-(4-chlorophenyl)-3-(2,6-difluoro-3-(propylsulfonamido)benzoyl)-1H-pyrrolo[2,3-b]pyridin-1-yl)methyl 2-((tert-butoxycarbonyl)amino)-3-methylpentanoate The title compound was prepared according to the procedure as described in Example 14 Step 2 using N-(3-(5-(4-chlorophenyl)-1H-pyrrolo[2,3-b]pyridine-3-carbonyl)-2,4-difluorophenyl)propane-1-sulfonamide (0.3 g, 0.61 mmol) in DMF (2.5 mL), KOH (69 mg, 1.22 mmol) and a solution of chloromethyl 2-((tert-butoxycarbonyl)amino)-3-methyl pentanoate (171 mg, 0.61 mmol) in DMF (0.5 mL). The crude product was purified by a silica gel column chromatography (PE/EtOAc (v/v)=4/1 to 3/1) to afford the title compound as a white solid (288 mg, 64%). The title compound was characterized by LC-MS and ¹H NMR as shown below:

LC-MS (ESI, pos. ion) m/z 733.1 [M+H]

¹H NMR (400 MHz, CDCl₃) δ 0.69-0.72 (t, J=7.3 Hz, 3H), 0.77-0.79 (d, J=7.3 Hz, 3H), 0.84-0.91 (m, 2H), 1.04-1.09 (t, J=7.4 Hz, 3H), 1.39 (s, 9H), 1.72-1.79 (m, 1H), 1.87-1.94 (m, 2H), 3.09-3.14 (m, 2H), 4.25-4.27 (m, 1H), 4.89 (br, 1H), 6.26-6.29 (d, J=10.6 Hz, 1H), 6.36-6.40 (d, J=10.6 Hz, 1H), 6.63 (br, 1H), 7.04-7.09 (m, 1H), 7.47-7.50 (dd, J=2.0, 6.6 Hz, 2H), 7.59-7.62 (dd, J=2.0, 6.6 Hz, 2H), 7.71-7.79 (td, J=5.5, 9.0 Hz, 1H), 7.83 (s, 1H), 8.67-8.68 (d, J=2.1 Hz, 1H), 8.85-8.86 (d, J=2.1 Hz, 1H).

Step 3) (2S)-(5-(4-chlorophenyl)-3-(2,6-difluoro-3-(propylsulfonamido)benzoyl)-1H-pyrrolo[2,3-b]pyridin-1-yl)methyl 2-amino-3-methylpentanoate hydrochloride A mixture of (5-(4-chlorophenyl)-3-(2,6-difluoro-3-(propylsulfonamido)benzoyl)-1H-pyrrolo[2,3-b]pyridin-1-yl) methyl 2-((tert-butoxycarbonyl)amino)-3-methyl pentanoate (285 mg, 0.45 mmol) and a saturated solution of HCl in EtOAc (3 mL) was stirred at 0° C. for 10 h. The resulting mixture was filtered to afford the title compound as a white solid (0.21 g, 80.8%). The title compound was characterized by LC-MS and ¹H NMR as shown below:

LC-MS (ESI, pos. ion) m/z 633.1 [M+H]⁺;

¹H NMR (400 MHz, d₆-DMSO) δ 0.69-0.72 (t, J=7.0 Hz, 3H), 0.75-0.78 (d, J=6.1 Hz, 3H), 0.95-1.00 (t, J=7.4 Hz, 3H), 1.03-1.07 (m, 2H), 1.72-1.79 (m, 2H), 1.79-1.84 (m, 1H), 3.12-3.16 (m, 2H), 3.95-3.97 (m, 1H), 6.37-6.41 (d, J=10.6 Hz, 1H), 6.51-6.55 (d, J=10.6 Hz, 1H), 7.31-7.36 (m, 1H), 7.58-7.61 (d, J=8.2 Hz, 2H), 7.62-7.67 (m, 1H), 7.80-7.83 (d, J=8.4 Hz, 2H), 8.52 (s, 1H), 8.55-8.63 (m, 2H), 8.67 (s, 1H), 8.80-8.82 (d, J=2.2 Hz, 1H), 9.88 (br, 1H).

Example 23

(S)-(5-(4-chlorophenyl)-3-(2,6-difluoro-3-(propylsulfonamido)benzoyl)-1H-pyrrolo[2,3-b]pyridin-1-yl)methyl 2-amino-4-methylpentanoate hydrochloride

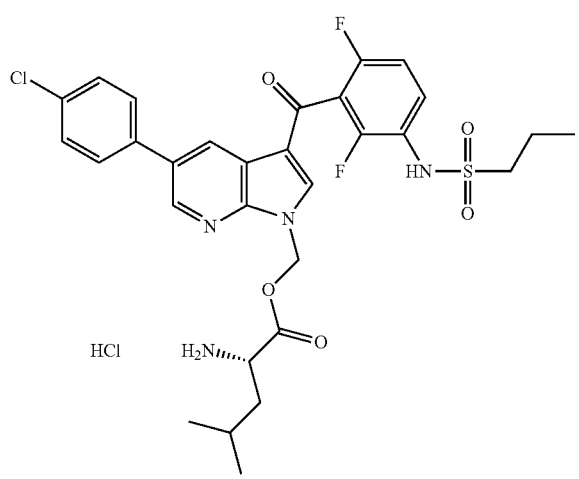 [SMILES: CCCS(=O)(=O)Nc1ccc(F)c(C(=O)c2cn(COC(=O)[C@@H](N)CC(C)C)c3ncc(-c4ccc(Cl)cc4)cc23)c1F ; Cl]

Step 1) chloromethyl 2-((tert-butoxycarbonyl)amino)-4-methylpentanoate

The title compound was prepared according to the procedure as described in Example 17 Step 1 using L-2-((tert-butoxycarbonyl)amino)-4-methylpentanoic acid (1 g, 4.31 mmol) in DCM (25 mL) and H₂O (25 mL), NaHCO₃ (1.55 g, 18.4 mmol), TBAHSO₄ (156 mg, 0.46 mmol) and a solution of chloromethyl sulfochloridate (559 μL, 5.5 mmol) in DCM (5 mL). The title compound was obtained as colorless oil (0.98 g, 81.1%). The title compound was characterized by ¹H NMR as shown below:

¹H NMR (400 MHz, CDCl₃) δ 0.94-0.97 (dd, J=1.2, 6.5 Hz, 6H), 1.44 (s, 9H), 1.50-1.54 (m, 1H), 1.70-1.76 (m, 1H), 4.33-4.35 (m, 1H), 4.83-4.86 (m, 1H), 5.61-5.63 (d, J=6.0 Hz, 1H), 5.85-5.87 (d, J=6.0 Hz, 1H).

Step 2) (S)-(5-(4-chlorophenyl)-3-(2,6-difluoro-3-(propylsulfonamido)benzoyl)-1H-pyrrolo[2,3-b]pyridin-1-yl)methyl 2-(tert-butoxylcarbonyl)amino)-4-methylpentanoate The title compound was prepared according to the procedure as described in Example 14 Step 2 using N-(3-(5-(4-chlorophenyl)-1H-pyrrolo[2,3-b]pyridine-3-carbonyl)-2,4-difluorophenyl)propane-1-sulfonamide (0.3 g, 0.61 mmol) in DMF (2.5 mL), KOH (69 mg, 1.22 mmol), and a solution of chloromethyl 2-((tert-butoxy-carbonyl)amino)-4-methyl-pentanoate (179 mg, 0.61 mmol) in DMF (0.5 mL). The crude product was purified by a silica gel column chromatography (PE/EtOAc (v/v)=4/1 to 3/1) to afford the title compound as a white solid (287 mg, 62.8%). The title compound was characterized by LC-MS and ¹H NMR as shown below:

LC-MS (ESI, pos. ion) m/z 733.1 [M+H]⁺;

¹H NMR (400 MHz, CDCl₃) δ 0.82-0.85 (d, J=6.2 Hz, 6H), 0.89-0.93 (m, 1H), 1.04-1.09 (t, J=7.4 Hz, 3H), 1.24-1.27 (m, 2H), 1.36 (s, 9H), 1.87-1.94 (m, 2H), 3.09-3.14 (m, 2H), 4.25-4.27 (m, 1H), 4.79 (br, 1H), 6.26-6.29 (d, J=10.6 Hz, 2H), 6.35-6.38 (d, J=10.6 Hz, 2H), 6.68 (br, 1H), 7.04-7.09 (m, 1H), 7.47-7.50 (dd, J=2.0, 6.6 Hz, 2H), 7.59-7.62 (dd, J=2.0, 6.6 Hz, 2H), 7.70-7.77 (td, J=5.5, 9.0 Hz, 1H), 7.83 (s, 1H), 8.67-8.68 (d, J=2.1 Hz, 1H), 8.85-8.86 (d, J=2.1 Hz, 1H).

Step 3) (S)-(5-(4-chlorophenyl)-3-(2,6-difluoro-3-(propylsulfonamido)benzoyl)-1H-pyrrolo[2,3-b]pyridin-1-yl)methyl 2-amino-4-methylpentanoate hydrochloride A solution of (5-(4-chlorophenyl)-3-(2,6-difluoro-3-(propylsulfonamido)benzoyl)-1H-pyrrolo[2,3-b]pyridin-1-yl) methyl2-((tert-butoxycarbonyl)amino)-4-methylpentanoate (284 mg, 0.39 mmol) was added in a saturated solution of HCl in EtOAc (3 mL). The reaction mixture was stirred at 0° C. for 10 h. The resulting mixture was concentrated in vacuo, and washed with PE/EtOAc (1/1) to afford the title compound as a white solid (204 mg, 78.7%).

LC-MS (ESI, pos. ion) m/z 633.1 [M+H]⁺;

¹H NMR (400 MHz, d₆-DMSO) δ 0.73-0.76 (t, J=5.4 Hz, 6H), 0.84-0.85 (m, 1H), 0.95-1.00 (t, J=7.4 Hz, 3H), 1.16-1.18 (m, 2H), 1.72-1.79 (m, 2H), 3.12-3.17 (m, 2H), 3.99-4.03 (m, 1H), 6.41-6.49 (dd, J=10.5, 19.5 Hz, 2H), 7.31-7.35 (m, 1H), 7.58-7.61 (dd, J=2.0, 6.6 Hz, 2H), 7.61-7.66 (m, 1H), 7.80-7.83 (dd, J=2.0, 6.6 Hz, 2H), 8.47 (br, 2H), 8.51 (s, 1H), 8.67 (br, 1H), 8.80-8.81 (d, J=2.2 Hz, 1H), 9.84 (s, 1H).

Example 24

1-(5-(4-chlorophenyl)-3-(2,6-difluoro-3-(propylsulfonamido)-benzoy)-1H-pyrrolo[2,3-b]pyridin-1-yl)ethyl 2-amino-3-methylbutanoate hydrochloride

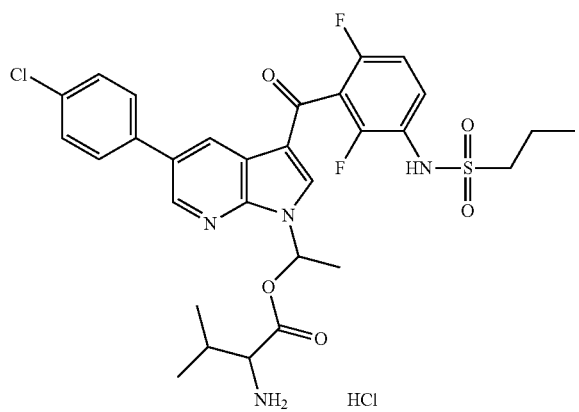 [SMILES: CCCS(=O)(=O)Nc1ccc(F)c(C(=O)c2cn(C(C)OC(=O)C(N)C(C)C)c3ncc(-c4ccc(Cl)cc4)cc23)c1F ; Cl]

Step 1) 1-chloroethyl sulfochloridate

Neat chlorosulfonic acid (8.96 g, 76.94 mmol) was added to 1-chloroethyl chloroformate dropwise at 0° C. The resulting mixture was stirred at 0° C. 16 h, then quenched with 15 mL of DCM and 15 mL of H$_2$O. The organic phase was washed with saturated Na$_2$CO$_3$ aqueous solution (20 mL), followed by brine (20 mL), dried over anhydrous Na$_2$SO$_4$ and concentrated in vacuo. The residue was distilled at 54° C. under reduced pressure to give the title compound as colorless oil (4.5 g, 36%). The title compound was characterized by $^1$H NMR and $^{13}$C NMR as shown below:

$^1$H NMR (400 MHz, CDCl$_3$) δ 1.98-1.99 (d, J=5.8 Hz, 3H), 6.46-6.50 (q, J=5.8 Hz, 1H);
$^{13}$C NMR (100 MHz, CDCl$_3$) δ 26.3, 91.1.

Step 2) 1-chloroethyl 2-((tert-butoxycarbonyl)amino)-3-methylbutanoate

The title compound was prepared according to the procedure as described in Example 17 step 1 using 2-((tert-butoxycarbonyl)amino)-3-methylbutanoic acid (3 g, 13.81 mmol) in DCM (75 mL) and H$_2$O (75 mL), NaHCO$_3$ (4.64 g, 55.23 mmol), TBAHSO$_4$ (469 mg, 1.38 mmol) and a solution of 1-chloroethyl sulfochloridate (2.97 g, 16.57 mmol) in DCM (15 mL). The crude product was purified by a silica gel column chromatography (PE/EtOAc (v/v)=100/1 to 50/1) to afford the title compound as a white solid (3 g, 78%). The title compound was characterized by $^1$H NMR as shown below:

$^1$H NMR (400 MHz, CDCl$_3$) δ 0.90-0.92 (m, 3H), 0.97-0.99 (m, 3H), 1.45 (s, 9H), 1.79-1.81 (m, 3H), 2.14-2.19 (m, 1H), 4.22-4.25 (m, 1H), 4.99-5.01 (m, 1H), 6.53-6.57 (dd, J=5.7, 11 Hz, 1H).

Step 3) 1-(5-(4-chlorophenyl)-3-(2,6-difluoro-3-(propylsulfonamido)benzoyl)-1H-pyrrolo[2,3-b]pyridin-1-yl)ethyl2-((tert-butoxycarbonyl)amino)-3-methylbutanoate The title compound was prepared according to the procedure as described in Example 14 step 2 using N-(3-(5-(4-chlorophenyl)-1H-pyrrolo[2,3-b]pyridine-3-carbonyl)-2,4-difluorophenyl)propane-1-sulfonamide (0.3 g, 0.61 mmol) in anhydrous DMF (2.5 mL), KOH (69 mg, 1.22 mmol) and a solution of 1-chloroethyl 2-((tert-butoxycarbonyl)amino)-3-methylbutanoate (172 mg, 0.61 mmol) in anhydrous DMF (0.5 mL). The crude product was purified by a silica gel column chromatography (PE/EtOAc (v/v)=4/1 to 3/1) to afford the title compound as orange oil (0.29 g, 65%). The title compound was characterized by $^1$H NMR as shown below:

$^1$H NMR (400 MHz, CDCl$_3$) δ 0.82-0.92 (m, 6H), 0.92-0.94 (t, J=7.4 Hz, 3H), 1.25 (s, 9H), 1.89-1.96 (m, 5H), 2.10-2.13 (m, 1H), 3.11-3.12 (m, 2H), 4.17-4.21 (m, 1H), 6.95-7.13 (m, 2H), 7.40-7.47 (m, 2H), 7.58-7.60 (m, 2H), 7.80-7.82 (m, 1H), 8.01 (s, 1H), 8.63-8.65 (m, 1H), 8.80-8.83 (m, 1H).

Step 4) 1-(5-(4-chlorophenyl)-3-(2,6-difluoro-3-(propylsulfonamido)-benzoy)-1H-pyrrolo[2,3-b]pyridin-1-yl)ethyl 2-amino-3-methylbutanoate hydrochloride A mixture of 1-(5-(4-chlorophenyl)-3-(2,6-difluoro-3-(propylsulfonamido)benzoyl)-1H-pyrrolo[2,3-b]pyridin-1-yl)ethyl 2-((tert-butoxycarbonyl)amino)-3-methylbutanoate (0.29 g, 0.39 mmol) and a saturated solution of HCl in EtOAc (4 mL) was stirred at rt for 2 h. The mixture was filtered to give the title compound as a white solid (0.15 g, 57%). The title compound was characterized by LC-MS and $^1$H NMR as shown below:

LC-MS (ESI, pos. ion) m/z 634.1 [(M+H)$^+$−HCl];
$^1$H NMR (400 MHz, CDCl$_3$) δ 0.85-0.89 (m, 6H), 0.98-0.99 (t, J=7.4 Hz, 3H), 1.76-1.89 (m, 3H), 1.92-2.03 (m, 3H), 3.00-3.13 (m, 2H), 4.00-4.05 (m, 1H), 6.95-7.13 (m, 2H), 7.40-7.47 (m, 2H), 7.58-7.60 (m, 2H), 7.80-7.82 (m, 1H), 8.01 (s, 1H), 8.63-8.65 (m, 1H), 8.80-8.83 (m, 1H).

Example 25 sodium (5-(4-chlorophenyl)-3-(2,6-difluoro-3-(propylsulfonamido)benzoyl)-1H-pyrrolo[2,3-b]pyridin-1-yl)methyl phosphate

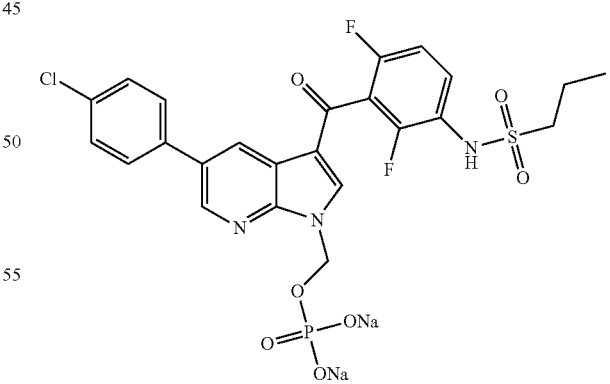

Step 1) di-tert-butyl(chloromethyl) phosphate

The title compound was prepared according to the procedure as described in Example 17 Step 1 using potassium di-tert-butylphosphate (1 g, 4.03 mmol) in DCM (20 mL) and H$_2$O (20 mL), NaHCO$_3$ (1.34 g, 16.1 mmol), TBAHSO$_4$ (136 mg, 0.4 mmol) and a solution of chloromethyl sulfochloridate (452 μL, 4.41 mmol) in DCM (5 mL). The title compound was obtained as colorless oil (1.02 g, 95.3%). The title compound was characterized by $^1$H NMR and $^{13}$C NMR as shown below:

$^1$H NMR (400 MHz, CDCl$_3$) δ 1.51 (s, 18H), 5.62-5.66 (d, J=14.9 Hz, 2H);

$^{13}$C NMR (100 MHz, CDCl$_3$) δ 29.9, 73.3, 84.1.

Step 2) di-tert-butyl((5-(4-chlorophenyl)-3-(2,6-difluoro-3-(propylsulfonamido)benzoyl)-1H-pyrrolo[2,3-b]pyridin-1-yl)methyl)phosphate To a solution of N-(3-(5-(4-chlorophenyl)-1H-pyrrolo[2,3-b]pyridine-3-carbonyl)-2,4-difluorophenyl)propane-1-sulfonamide (0.4 g, 0.82 mmol) in DMF (3.5 mL) was added KOH (91 mg, 1.63 mmol). The reaction was stirred at 10° C. for 20 min, followed by the dropwise addition of a solution of di-tert-butyl(chloromethyl) phosphate (0.21 g, 0.82 mmol) in DMF (1 mL) over 30 min. The reaction was stirred further at 10° C. for 16 h, then diluted with EtOAc (100 mL). The mixture was washed with H$_2$O (100 mL) and extracted with DCM (100 mL×2). The combined organic phases were concentrated in vacuo and the residue was purified by a silica gel column chromatography (PE/EtOAc (v/v)=3/1) to give the title compound as colorless oil (0.28 g, 47.2%). The title compound was characterized by LC-MS and $^1$H NMR as shown below:

LC-MS (ESI, pos. ion) m/z 712.2 [M+H]$^+$;

$^1$H NMR (400 MHz, CDCl$_3$) δ 1.03-1.07 (t, J=7.4 Hz, 3H), 1.35 (s, 18H), 1.84-1.94 (m, 2H), 3.07-3.11 (m, 2H), 6.13-6.17 (d, J=13.0 Hz, 2H), 7.01-7.06 (m, 1H), 7.46-7.49 (d, J=8.4 Hz, 2H), 7.58-7.60 (d, J=8.4 Hz, 2H), 7.67-7.74 (td, J=8.9, 5.6 Hz, 1H), 7.96 (s, 1H), 8.67-8.68 (d, J=2.1 Hz, 1H), 8.87-8.88 (d, J=2.0 Hz, 1H).

Step 3) (5-(4-chlorophenyl)-3-(2,6-difluoro-3-(propylsulfonamido)benzoyl)-1H-pyrrolo[2,3-b]pyridin-1-yl)methyl dihydrogen phosphate To a solution of di-tert-butyl((5-(4-chlorophenyl)-3-(2,6-difluoro-3-(propyl sulfonamido)benzoyl)-1H-pyrrolo[2,3-b]pyridin-1-yl)methyl) phosphate (1 g, 1.4 mmol) in DCM (25 mL) was added TFA (1.6 mL, 2.4 g, 21 mmol). The reaction was stirred at rt for 2 h, and then concentrated in vacuo. The residue was washed with 20 mL of EtOAc to give the title compound as a white solid (0.56 g, 66.5%). The title compound was characterized by LC-MS and $^1$H NMR as shown below:

LC-MS (ESI, pos. ion) m/z 600.0 [M+H]$^+$;

$^1$H NMR (400 MHz, d$_6$-DMSO) δ 0.94-0.98 (t, J=7.4 Hz, 3H), 1.70-1.77 (m, 2H), 3.10-3.14 (m, 2H), 6.03-6.06 (d, J=9.6 Hz, 2H), 7.29-7.33 (m, 1H), 7.57-7.60 (d, J=8.5 Hz, 2H), 7.60-7.65 (m, 1H), 7.80-7.82 (d, J=8.5 Hz, 2H), 8.42-8.43 (m, 1H), 8.65 (s, 1H), 8.79-8.80 (d, J=2.1 Hz, 1H), 9.82 (br, 1H).

Step 4) sodium (5-(4-chlorophenyl)-3-(2,6-difluoro-3-(propylsulfonamido)benzoyl)-1H-pyrrolo[2,3-b]pyridin-1-yl)methyl phosphate To a solution of (5-(4-chlorophenyl)-3-(2,6-difluoro-3-(propylsulfonamido)benzoyl)-1H-pyrrolo[2,3-b]pyridin-1-yl)methyl dihydrogen phosphate (396 mg, 0.66 mmol) in THF (20 mL) was added dropwise a solution of NaOH (58 mg, 1.45 mmol) in 0.3 mL of H$_2$O and 4 mL of THF at rt. The reaction was stirred at rt for 4 h, and then filtered to give the title compound as a white solid (401 mg, 94.4%). The title compound was characterized by LC-MS and $^1$H NMR as shown below:

LC-MS (ESI, pos. ion) m/z 600.0 [M+H]$^+$;

$^1$H NMR (400 MHz, D$_2$O) δ 0.82-0.86 (t, J=7.4 Hz, 3H), 1.62-1.68 (m, 2H), 2.88-2.92 (m, 2H), 5.79-5.82 (d, J=9.6 Hz, 2H), 6.96-7.01 (m, 1H), 7.27-7.30 (d, J=8.5 Hz, 2H), 7.31-7.37 (td, J=9.3, 6.0 Hz, 1H), 7.41-7.43 (d, J=8.5 Hz, 2H), 8.34-8.35 (m, 2H), 8.46-8.47 (d, J=2.0 Hz, 1H).

Example 26

(5-(4-chlorophenyl)-3-(2,6-difluoro-3-(propylsulfonamido)benzoyl)-1H-pyrrolo[2,3-b]pyridin-1-yl) methyl ethyl carbonate

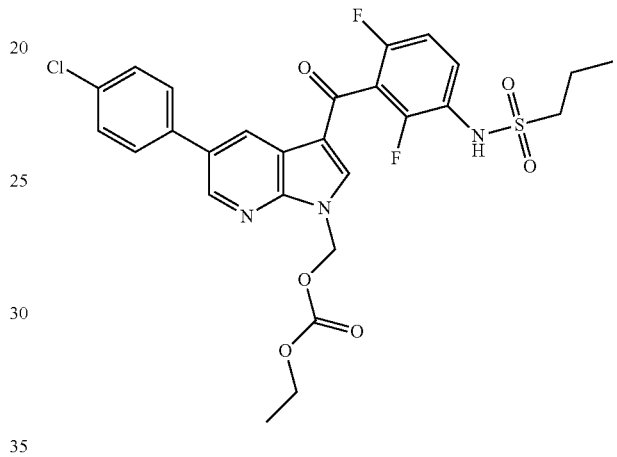

Step 1) chloromethyl ethyl carbonate

To a solution of chloromethyl chloroformate (10 g, 78.2 mmol) in DCM (200 mL) was added a mixture of ethanol (5 mL, 85.9 mmol) and pyridine (7.5 mL, 93.2 mmol) in DCM (50 mL) at −20° C. The reaction was stirred at 0° C. for 1 h, then at rt for another 2 h. The resulting mixture was washed with 1N HCl solution (300 mL), followed by brine (200 mL). The organic phase was dried over anhydrous Na$_2$SO$_4$ and concentrated in vacuo to give the title compound as colorless oil (8.75 g, 81.1%). The compound was used in the next step without further purification. The title compound was characterized by $^1$H NMR as shown below:

$^1$H NMR (400 MHz, CDCl$_3$) δ 1.32-1.36 (t, J=7.2 Hz, 3H), 4.26-4.31 (m, J=7.2 Hz, 2H), 5.72 (s, 2H).

Step 2) (5-(4-chlorophenyl)-3-(2,6-difluoro-3-(propylsulfonamido)benzoyl)-1H-pyrrolo[2,3-b]pyridin-1-yl)methyl ethyl carbonate To a mixture of N-(3-(5-(4-chlorophenyl)-1H-pyrrolo[2,3-b]pyridine-3-carbonyl)-2,4-difluorophenyl)propane-1-sulfonamide (0.1 g, 0.2 mmol) and Et$_3$N (114 μL, 0.8 mmol) in DMF (0.6 mL) was added a solution of TBAB (132 mg, 0.4 mmol) in DMF (0.2 mL). The reaction was stirred at 10° C. for 30 min, followed by dropwise addition of a solution of chloromethyl ethyl carbonate (34 mg, 0.25 mmol) in DMF (0.2 mL). The reaction was stirred at 10° C. for another 3 h, then diluted with EtOAc (40 mL) and filtered. The filtrate was concentrated in vacuo and the residue was purified by a silica gel column chromatography (PE/EtOAc (v/v)=2/1) to afford the title compound as a white solid (85 mg, 73%). The title compound was characterized by LC-MS and ¹H NMR as shown below:

LC-MS (ESI, pos. ion) m/z 592.0 [M+H]⁺;
¹H NMR (400 MHz, CDCl₃) δ 1.05-1.10 (t, J=7.4 Hz, 3H), 1.25-1.32 (t, J=7.2 Hz, 3H), 1.85-1.97 (m, 2H), 3.09-3.16 (m, 2H), 4.18-4.25 (q, J=7.1 Hz, 2H), 6.29 (s, 2H), 6.51 (s, 1H), 7.04-7.10 (m, 1H), 7.46-7.51 (d, J=8.5 Hz, 2H), 7.57-7.63 (d, J=8.5 Hz, 2H), 7.70-7.77 (m, 1H), 7.86 (s, 1H), 8.67-8.70 (d, J=2.1 Hz, 1H), 8.83-8.85 (d, J=2.1 Hz, 1H).

Example 27

(5-(4-chlorophenyl)-3-(2,6-difluoro-3-(propylsulfonamido)benzoyl)-1H-pyrrolo[2,3-b]pyridin-1-yl) methyl isopropyl carbonate

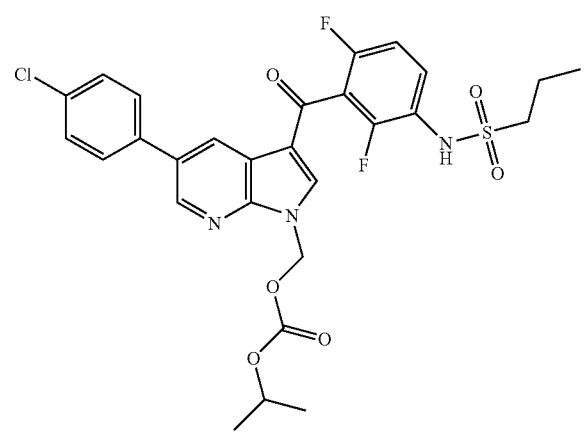 [SMILES: CCCS(=O)(=O)Nc1ccc(F)c(C(=O)c2cn(COC(=O)OC(C)C)c3ncc(-c4ccc(Cl)cc4)cc23)c1F]

Step 1) chloromethyl isopropyl carbonate

The title compound was prepared according to the procedure as described in Example 26 step 1 using a solution of chloromethyl chloroformate (10 g, 78.2 mmol) in DCM (200 mL), a mixture of i-PrOH (6.6 mL, 86.2 mmol) and pyridine (7.5 mL, 93.2 mmol) in DCM (50 mL). The title compound was obtained as colorless oil (9.63 g, 81.0%) and was used in the next step without further purification. The title compound was characterized by ¹H NMR as shown below:

¹H NMR (400 MHz, CDCl₃) δ 1.33 (s, 3H), 1.34 (s, 3H), 4.92-4.99 (m, J=6.3 Hz, 1H), 5.72 (s, 3H).

Step 2) (5-(4-chlorophenyl)-3-(2,6-difluoro-3-(propylsulfonamido)benzoyl)-1H-pyrrolo[2,3-b]pyridin-1-yl)methyl isopropyl carbonate To a mixture of N-(3-(5-(4-chlorophenyl)-1H-pyrrolo[2,3-b]pyridine-3-carbonyl)-2,4-difluorophenyl)propane-1-sulfonamide (0.2 g, 0.41 mmol) and KOH (46 mg, 0.82 mmol) in DMF (1.5 mL) was added a solution of chloromethyl isopropyl carbonate (62 mg, 0.41 mmol) in DMF (0.5 mL) over 30 min. The reaction mixture was stirred at 10° C. for 3 h, then diluted with EtOAc (40 mL) and filtered. The filtrate was concentrated in vacuo and the residue was purified by a silica gel column chromatography (PE/EtOAc (v/v)=2/1) to afford the title compound as a white solid (105 mg, 43%). The title compound was characterized by LC-MS and ¹H NMR as shown below:

LC-MS (ESI, pos. ion) m/z 606.0 [M+H]⁺;

¹H NMR (400 MHz, CDCl₃) δ 1.04-1.10 (t, J=7.4 Hz, 3H), 1.20-1.35 (m, 6H), 1.85-1.95 (m, 2H), 3.09-3.15 (m, 2H), 4.84-4.92 (m, 1H), 6.28 (s, 2H), 6.56 (s, 1H), 7.03-7.10 (m, 1H), 7.46-7.51 (d, J=8.5 Hz, 2H), 7.57-7.63 (d, J=8.5 Hz, 2H), 7.69-7.77 (m, 1H), 7.87 (s, 1H), 8.66-8.70 (d, J=2.1 Hz, 1H), 8.83-8.87 (d, J=2.1 Hz, 1H).

Example 28

1-(5-(4-chlorophenyl)-3-(2,6-difluoro-3-(propylsulfonamido)benzoyl)-1H-pyrrolo[2,3-b]pyridin-1-yl) ethyl ethyl carbonate

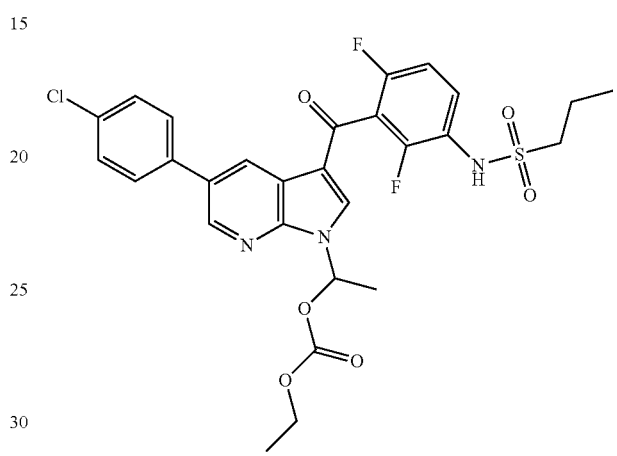

Step 1) 1-chloroethyl ethyl carbonate

The title compound was prepared according to the procedure as described in Example 26 step 1 using a solution of 1-chloroethyl chloroformate (10 g, 69.9 mmol) in DCM (200 mL), a mixture of ethanol (4.5 mL, 77.2 mmol) and pyridine (6.8 mL, 84.5 mmol) in DCM (50 mL). The title compound was obtained as colorless oil (9.32 g, 87.7%) and was used in the next step without further purification. The title compound was characterized by ¹H NMR as shown below:

¹H NMR (400 MHz, CDCl₃) δ 1.32-1.36 (t, J=7.1 Hz, 3H), 1.82-1.84 (d, J=5.8 Hz, 3H), 4.24-4.30 (q, J=7.1 Hz, 2H), 6.41-6.46 (q, J=5.8 Hz, 1H).

Step 2) 1-(5-(4-chlorophenyl)-3-(2,6-difluoro-3-(propylsulfonamido)benzoyl)-1H-pyrrolo[2,3-b]pyridin-1-yl)ethyl ethyl carbonate To a solution of N-(3-(5-(4-chlorophenyl)-1H-pyrrolo[2,3-b]pyridine-3-carbonyl)-2,4-difluorophenyl)propane-1-sulfonamide (0.1 g, 0.2 mmol) in DMF (1 mL) was added K₂CO₃ (85 mg, 0.6 mmol). The reaction was stirred at rt for 10 min, followed by the addition of TBAB (132 mg, 0.4 mmol) and a solution of 1-chloroethyl ethyl carbonate (35 mg, 0.25 mmol) in DMF (100 μA). The mixture was stirred at rt for 16 h, then diluted with EtOAc (40 mL) and filtered. The filtrate was concentrated in vacuo and the residue was purified by a silica gel column chromatography (PE/EtOAc (v/v)=4/1) to afford the title compound as a white solid (61 mg, 50%). The title compound was characterized by LC-MS and ¹H NMR as shown below:

LC-MS (ESI, neg. ion) m/z 603.5 [M−H]⁻;

¹H NMR (400 MHz, CDCl₃) δ 1.04-1.10 (t, J=7.4 Hz, 3H), 1.25-1.33 (t, J=7.1 Hz, 3H), 1.85-1.93 (m, 2H), 1.93-2.00 (d,

J=6.3 Hz, 3H), 3.09-3.17 (m, 2H), 4.12-4.27 (m, 2H), 6.55 (br, 1H), 7.04-7.10 (m, 1H), 7.29-7.36 (q, J=6.3 Hz, 1H), 7.45-7.50 (m, 2H), 7.57-7.63 (m, 2H), 7.68-7.77 (m, 1H), 7.79 (s, 1H), 8.67-8.70 (d, J=2.2 Hz, 1H), 8.80-8.84 (d, J=2.1 Hz, 1H).

Example 29

1-(5-(4-chlorophenyl)-3-(2,6-difluoro-3-(propylsulfonamido)benzoyl)-1H-pyrrolo[2,3-b]pyridin-1-yl)ethyl cyclohexyl carbonate

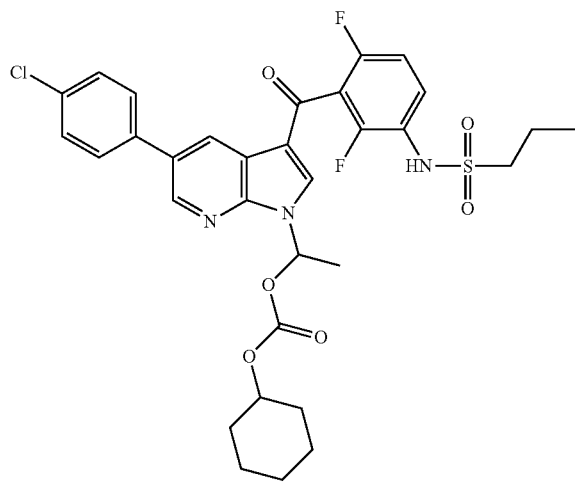 [SMILES: CCCS(=O)(=O)Nc1ccc(F)c(C(=O)c2cn(C(C)OC(=O)OC3CCCCC3)c3ncc(-c4ccc(Cl)cc4)cc23)c1F]

Step 1) 1-chloroethyl cyclohexyl carbonate

The title compound was prepared according to the procedure as described in Example 26 step 1 using a solution of 1-chloroethyl carbonochloridate (5 g, 35 mmol) in DCM (100 mL), cyclohexanol (3.9 g, 38.5 mmol) and pyridine (3.3 g, 42 mmol). The title compound was obtained as colorless oil (7 g, 96.9%) and was used in the next step without further purification. The title compound was characterized by $^1$H NMR as shown below:

$^1$H NMR (400 MHz, CDCl$_3$) δ 1.28-1.25 (m, 1H), 1.30-1.42 (m, 2H), 1.48-1.58 (m, 3H), 1.74-1.78 (m, 2H), 1.82-1.83 (d, J=5.8 Hz, 3H), 1.91-1.96 (m, 2H), 4.66-4.72 (m, 1H), 6.41-6.45 (m, 1H).

Step 2) 1-(5-(4-chlorophenyl)-3-(2,6-difluoro-3-(propylsulfonamido)benzoyl)-1H-pyrrolo[2,3-b]pyridin-1-yl)ethyl cyclohexyl carbonate To a solution of N-(3-(5-(4-chlorophenyl)-1H-pyrrolo[2,3-b]pyridine-3-carbonyl)-2,4-difluorophenyl)propane-1-sulfonamide (5 g, 10.2 mmol) in THF (36 mL) was added KOH (1.1 g, 20.4 mmol). The reaction was stirred at rt for 0.5 h, followed by the addition of a solution of 1-chloroethyl cyclohexyl carbonate (2.3 g, 11.2 mmol) in THF (9 mL). The mixture was refluxed for 16 h, then cooled to rt and diluted with THF (50 mL). The resulting mixture was filtered and the filtrate was concentrated in vacuo. The residue was purified by a silica gel column chromatography (PE/EtOAc (v/v)=8/1) to give the title compound as a white solid (3.49 g, 51.9%). The title compound was characterized by LC-MS and $^1$H NMR as shown below:

LC-MS (ESI, neg. ion) m/z 657.5 [M−H]$^−$;

$^1$H NMR (400 MHz, CDCl$_3$) δ 1.05-1.08 (t, J=7.4 Hz, 3H), 1.20-1.58 (m, 8H), 1.72 (m, 2H), 1.89-1.94 (m, 5H), 3.10-3.14 (m, 2H), 4.59 (m, 1H), 6.40-6.50 (d, J=1.7 Hz, 1H), 7.04-7.09 (m, 1H), 7.30-7.33 (m, 1H), 7.46-7.48 (m, 1H), 7.58-7.60 (m, 1H), 7.71-7.74 (m, 1H), 7.79 (s, 1H), 8.67 (d, J=2.2 Hz, 1H), 8.81-8.82 (d, J=2.0 Hz, 1H).

Example 30

1-(5-(4-chlorophenyl)-3-(2,6-difluoro-3-(propylsulfonamido)benzoyl)-1H-pyrrolo[2,3-b]pyridin-1-yl)ethyl isopropyl carbonate

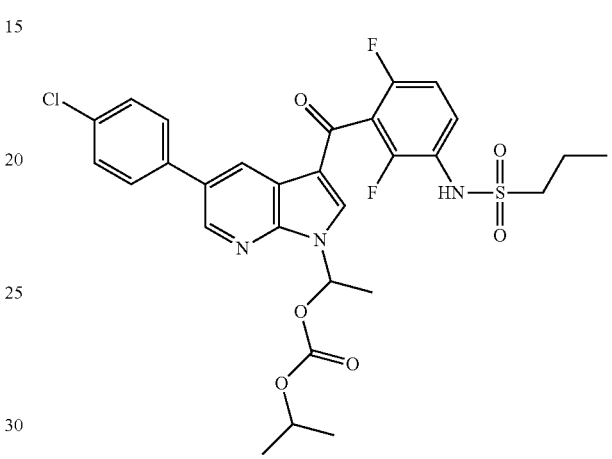

Step 1) 1-chloroethyl isopropyl carbonate

To a solution of 1-chloroethyl carbonochloridate (10 g, 69.9 mmol) in DCM (200 mL) was added a solution of isopropanol (5.9 mL, 76.9 mmol) and pyridine (6.75 mL, 83.9 mmol) in DCM (50 mL) at −20° C. The reaction was stirred at 0° C. for 2 h, then at rt for another 2 h. The mixture was washed with 1N HCl solution (250 mL×2), followed by brine (250 mL). The organic phase was dried over anhydrous Na$_2$SO$_4$ and concentrated in vacuo to give the title compound as colorless oil (9.6 g, 82.4%). The product was used in the next step without further purification. The title compound was characterized by $^1$H NMR as shown below:

$^1$H NMR (400 MHz, CDCl$_3$) δ 1.31-1.34 (m, 6H), 1.81-1.82 (d, J=5.84 Hz, 3H), 4.88-4.98 (m, 1H), 6.41-6.45 (t, J=5.84 Hz, 1H).

Step 2) 1-(5-(4-chlorophenyl)-3-(2,6-difluoro-3-(propylsulfonamido)benzoyl)-1H-pyrrolo[2,3-b]pyridin-1-yl)ethyl isopropyl carbonate The title compound was prepared according to the procedure as described in Example 26 step 2 using N-(3-(5-(4-chlorophenyl)-1H-pyrrolo[2,3-b]pyridine-3-carbonyl)-2,4-difluorophenyl)propane-1-sulfonamide (0.3 g, 0.61 mmol), KOH (69 mg, 1.23 mmol) in anhydrous DMF (2 mL), a solution of TBAB (396 mg, 1.23 mmol) in anhydrous DMF (0.5 mL) and a solution of 1-chloroethyl isopropyl carbonate (101 mg, 0.61 mmol) in anhydrous DMF (0.5 mL). The crude product was purified by a silica gel column chromatography (PE/EtOAc (v/v)=5/1), and recrystallized in methanol to afford the title compound as a white solid (42 mg, 11.1%). The title compound was characterized by LC-MS and $^1$H NMR as shown below:

LC-MS (ESI, neg. ion) m/z 617.4 [M−H]⁻;
¹H NMR (400 MHz, CDCl₃) δ 1.04-1.08 (t, J=7.4 Hz, 3H), 1.22-1.29 (m, 6H), 1.87-1.94 (m, 5H), 3.10-3.14 (m, 2H), 4.84-4.87 (m, 1H), 6.59 (br, 1H), 7.04-7.09 (m, 1H), 7.30-7.34 (t, J=6.2 Hz, 1H), 7.46-7.48 (d, J=8.5 Hz, 2H), 7.58-7.60 (d, J=8.5 Hz, 2H), 7.69-7.75 (td, J=5.5, 9.0 Hz, 1H), 7.79 (s, 1H), 8.67-8.68 (d, J=2.2 Hz, 1H), 8.81-8.82 (d, J=2.0 Hz, 1H).

Example 31

(5-(4-chlorophenyl)-3-(2,6-difluoro-3-(propylsulfonamido)benzoyl)-1H-pyrrolo[2,3-b]pyridin-1-yl)methyl phenyl carbonate

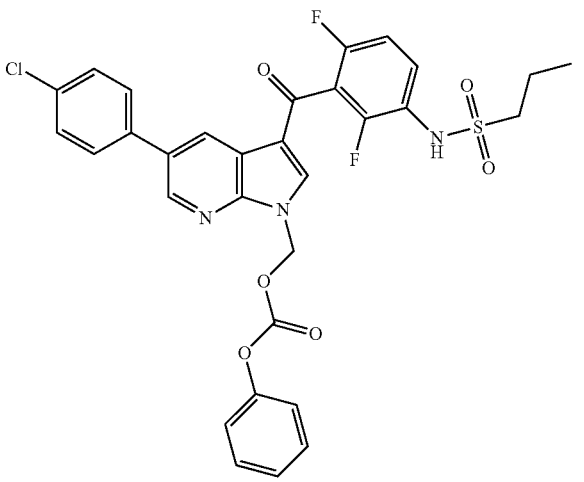 [SMILES: CCCS(=O)(=O)Nc1ccc(F)c(C(=O)c2cn(COC(=O)Oc3ccccc3)c3ncc(-c4ccc(Cl)cc4)cc23)c1F]

Step 1) chloromethyl phenyl carbonate

To a solution of chloromethyl chloroformate (1 g, 7.8 mmol) in DCM (40 mL) was added a mixture of phenol (0.73 g, 7.8 mmol) and pyridine (750 μL, 9.3 mmol) in DCM (10 mL) at −20° C. over 20 min. The reaction was stirred at 0° C. for 4 h, then at rt for another 1 h. The mixture was washed with 1N HCl solution (50 mL), followed by brine (50 mL). The organic phase was dried over anhydrous Na₂SO₄ and concentrated in vacuo. The residue was purified by a silica gel column chromatography (PE/EtOAc (v/v)=100/1) to give the title compound as colorless oil (847 mg, 58.2%). The title compound was characterized by ¹H NMR as shown below:
¹H NMR (400 MHz, CDCl₃) δ 5.84 (s, 2H), 7.22-7.27 (d, J=8.2 Hz, 2H), 7.28-7.34 (t, J=7.4 Hz, 1H), 7.40-7.49 (t, J=7.8 Hz, 2H).

Step 2) (5-(4-chlorophenyl)-3-(2,6-difluoro-3-(propylsulfonamido)benzoyl)-1H-pyrrolo[2,3-b]pyridin-1-yl)methyl phenyl carbonate To a mixture of N-(3-(5-(4-chlorophenyl)-1H-pyrrolo[2,3-b]pyridine-3-carbonyl)-2,4-difluorophenyl)propane-1-sulfonamide (0.1 g, 0.2 mmol), TBAB (132 mg, 0.4 mmol) and Et₃N (114 μL, 0.8 mmol) in DMF (1 mL) was added chloromethyl phenyl carbonate (46 mg, 0.25 mmol). The reaction was stirred at rt for 12 h, then diluted with EtOAc (40 mL) and filtered. The filtrate was concentrated in vacuo and the residue was purified by a silica gel column chromatography (PE/EtOAc (v/v)=4/1) to afford the title compound as a white solid (10 mg, 7.7%). The title compound was characterized by LCMS and ¹H NMR as shown below:
LC-MS (ESI, pos. ion) m/z 640.0 [M+H]⁺;
¹H NMR (400 MHz, CDCl₃) δ 0.98-1.12 (t, J=7.4 Hz, 3H), 1.80-1.90 (m, 2H), 3.02-3.09 (m, 2H), 6.40 (s, 2H), 6.51 (s, 1H), 7.02-7.08 (m, 1H), 7.11-7.16 (d, J=7.6 Hz, 2H), 7.25-7.30 (m, 1H), 7.37-7.42 (m, 2H), 7.46-7.52 (d, J=8.4 Hz, 2H), 7.57-7.64 (d, J=8.4 Hz, 2H), 7.67-7.75 (m, 1H), 7.88 (s, 1H), 8.70-8.73 (d, J=2.1 Hz, 1H), 8.87-8.90 (d, J=2.1 Hz, 1H).

Example 32 sodium 1-(5-(4-chlorophenyl)-3-(2,6-difluoro-3-(propylsulfonamido)benzoyl)-1H-pyrrolo[2,3-b]pyridin-1-yl)ethyl phosphate

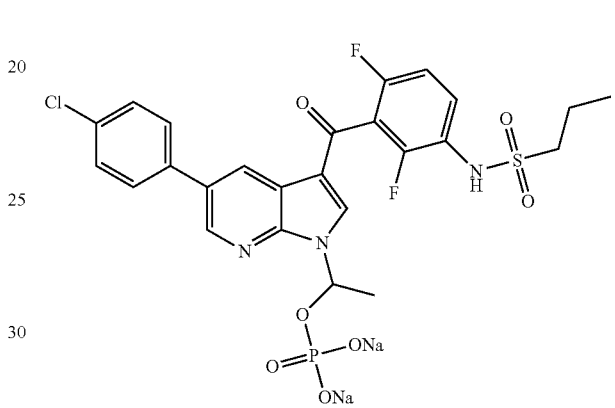

Step 1) 1-chloroethyl sulfochloridate

To a solution of 1-Chloroethyl chloroformate (54.4 mL, 504 mmol) was added chlorosulfonic acid (49.0 mL, 729 mmol) dropwise at 0° C. over 40 min. The mixture was stirred at 0° C. for 2 h, and then 5° C. for another 10 min. To the reaction mixture were added CH₂Cl₂ (500 mL) and then ice (20 g) slowly. The mixture was washed with saturate aqueous NaHCO₃ (400 mL) and brine (400 mL), dried over anhydrous Na₂SO₄, filtered, and concentrated to give light yellow oil (54.2 g, 60%). The title compound was characterized by ¹H NMR as shown below:
¹H NMR (400 MHz, CDCl₃): δ 1.98-2.00 (d, J=5.8 Hz, 3H), δ 6.46-6.51 (q, J=5.8 Hz, 1H).

Step 2) Di-tert-butyl 1-chloroethyl phosphate

To a solution of potassium di-tert-butylphosphate (33 g, 133 mmol) in CH₂Cl₂/H₂O (600 mL/600 mL) were added NaHCO₃ (44.6 g, 531 mmol) and TBAHSO₄ (4.52 g, 13.3 mmol), and then the mixture was stirred at 0° C. for 10 min. Then a solution of 1-chloroethyl sulfochloridate (26 g, 146 mmol) in CH₂Cl₂ (100 mL) was added dropwise over 30 min to the reaction mixture. The mixture was stirred further at room temperature for 20 h. The organic layer was separated, and then washed with water (300 mL×3) and brine (300 mL). Then it was dried over anhydrous Na₂SO₄, filtered, and concentrated in vacuo to give light yellow oil (14.3 g, 40%). The title compound was characterized by ¹H NMR as shown below:
¹H NMR (400 MHz, CDCl₃): δ 1.52 (s, 18H), 1.81 (d, J=5.6 Hz, 3H), 6.17-6.24 (m, 1H).

Step 3) di-tert-butyl 1-(5-(4-chlorophenyl)-3-(2,6-difluoro-3-(propylsulfonamido)benzoyl)-1H-pyrrolo[2,3-b]pyridin-1-yl)ethyl phosphate To a solution of N-(3-(5-(4-chlorophenyl)-1H-pyrrolo[2,3-b]pyridine-3-carbonyl)-2,4-difluorophenyl)propane-1-sulfonamide (9.8 g, 20 mmol) in DMF (120 mL) were added KOH (4.48 g, 80 mmol) and KI (0.33 g, 2 mmol). Then a solution of di-tert-butyl 1-chloroethyl phosphate (10.9 g, 40 mmol) in DMF (20 mL) was added dropwise to the above reaction mixture at rt over 5 min under $N_2$ protection and then the reaction mixture was stirred at 50° C. for 6 h, followed by being diluted with ethyl acetate (700 mL). The mixture was washed with water (400 mL×3) and brine (400 mL). The organic layer was concentrated, and then $CH_2Cl_2$ (20 mL) was added. The solid was collected through filtration in vacuo, and then the filter was concentrated to give a brown solid (31 g, 106%). The title compound was characterized by LC-MS as shown below:

LC-MS (ESI, pos. ion) m/z: 724.2 [M−1].

Step 4) 1-(5-(4-chlorophenyl)-3-(2,6-difluoro-3-(propylsulfonamido)benzoyl)-1H-pyrrolo[2,3-b]pyridin-1-yl)ethyl dihydrogen phosphate To the solution of di-tert-butyl 1-(5-(4-chlorophenyl)-3-(2,6-difluoro-3-(propylsulfonamido)benzoyl)-1H-pyrrolo[2,3-b]pyridin-1-yl)ethyl phosphate (20 g, crude) in EA (30 mL) was added phosphate (85%, 90 mL) and the mixture was stirred at room temperature for 2 min. Then the reaction mixture was quenched by adding water (200 mL), and then extracted with EtOAc (300 mL×3). The combined organic layers were concentrated in vacuo to give a brown solid (19.5 g, 74%). The title compound was characterized by LC-MS and $^1$H NMR as shown below:

LC-MS (ESI, pos. ion) m/z: 612.1 [M−1];

$^1$H NMR (400 MHz, DMSO-$d_6$): δ 0.95 (t, J=7.4 Hz, 3H), 1.65-1.81 (m, 5H), 3.11 (t, J=7.4 Hz, 2H), 6.75-6.87 (m, 1H), 7.28 (t, J=8.8 Hz, 1H), 7.57 (d, J=8.3 Hz, 2H), 7.51-7.72 (m, 1H), 7.77 (d, J=8.3 Hz, 2H), 8.31-8.35 (m, 1H), 8.57-8.61 (m, 1H), 8.69-8.74 (m, 1H), 9.85 (br, 1H).

Step 5) Sodium 1-(5-(4-chlorophenyl)-3-(2,6-difluoro-3-(propylsulfonamido)benzoyl)-1H-pyrrolo[2,3-b]pyridin-1-yl)ethyl phosphate To the solution of 1-(5-(4-chlorophenyl)-3-(2,6-difluoro-3-(propylsulfonamido)benzoyl)-1H-pyrrolo[2,3-b]pyridin-1-yl)ethyl dihydrogen phosphate (4 g, 6.5 mmol) in EA/THF (30 mL, 2/1) was added NaOH (0.57 g, 14.3 mmol) in $H_2O$ (1 mL) at rt. Then the mixture was stirred at room temperature over night. The mixture was filtered and dried under vacuum at 45° C. for 10 h to give the title compound as a white solid (4.0 g, 93%). The title compound was characterized by LC-MS and $^1$H NMR as shown below:

LC-MS (ESI, pos. ion) m/z: 612.1 [M−1];

$^1$H NMR (400 MHz, $D_2O$): δ 0.88 (t, J=7.4 Hz, 3H), 1.65-1.75 (m, 2H), 1.74 (d, J=5.9 Hz, 3H) 2.93 (t, J=7.5 Hz, 2H), 6.55-6.62 (m, 1H), 7.04 (t, J=8.8 Hz, 1H), 7.40 (d, J=8.4 Hz, 2H), 7.37-7.44 (m, 1H), 7.55 (d, J=8.2 Hz, 2H), 8.32 (br, 1H), 8.41-8.47 (m, 1H), 8.55 (d, J=1.8 Hz, 1H).

BIOLOGICAL TESTING

The efficacy of the compounds disclosed herein can be evaluated as follows.

Example A

General Bio-Analysis Method

The LC/MS/MS system used in the analysis consists of an Agilent 1200 Series vacuum degasser, binary pump, well-plate autosampler, thermostated column compartment, the Agilent G6430 TripleQuadrupole Mass Spectrometer with an electrospray ionization (ESI) source. Quantitative analysis was carried out using MRM mode. The parameters for MRM transitions are in the Table A.

TABLE A

| MRM | 490.2→383.1 |
|---|---|
| Fragmentor | 230 V |
| CE | 55 V |
| Drying Gas Temp | 350° C. |
| Nebulize | 40 psi |
| Drying Gas Flow | 10 L/min |

An Agilent XDB-C18, 2.1×30 mm, 3.5 μM column was used for the analysis. 5 μL of the samples were injected. Analysis condition: The mobile phase was 0.1% formic acid in water (A) and 0.1% formic acid in methanol (B). The flow rate was 0.4 mL/min. And the gradient of Mobile phase was in the Table B.

TABLE B

| Time | Gradient of Mobile Phase B |
|---|---|
| 0.5 min | 5% |
| 1.0 min | 95% |
| 2.2 min | 95% |
| 2.3 min | 5% |
| 5.0 min | stop |

Alternatively, an Agilent 6330 series LC/MS/MS spectrometer equipped with G1312A binary pumps, a G1367A autosampler and a G1314C UV detector was used in the analysis. An ESI source was used on the LC/MS/MS spectrometer. The analysis was done in positive ion mode as appropriate and the MRM transition for each analyte was optimized using standard solution. A Capcell MP-C18 100× 4.6 mm I.D., 5 nM column (Phenomenex, Torrance, Calif., USA) was used during the analysis. The mobile phase was 5 mM ammonia acetate, 0.1% MeOH in water (A): 5 mM ammonia acetate, 0.1% MeOH in acetonitrile (B) (70:30, v/v). The flow rate was 0.6 mL/min. Column was maintained at ambient temperature. 20 μL of the samples were injected.

Example B

Compound Stability in Human and Rat Liver Microsomes

Human or rat liver microsomes incubations were conducted in duplicate in polypropylene tubes. The typical incubation mixtures consisted of human (or rat) liver microsomes (0.5 mg protein/mL), compounds of interest (5 μM) and NADPH (1.0 mM) in a total volume of 200 μL potassium phosphate buffer (PBS, 100 mM, pH7.4). Compounds were dissolved in DMSO and diluted with PBS such that the final concentration of DMSO was 0.05%. The enzymatic reactions were commenced with the addition of protein after a 3 min preincubation and incubated in a water bath open to the air at 37° C. Reactions were terminated at various time points (0, 5, 10, 15, 30, 60 min) by adding equal volume of ice-cold acetonitrile. The samples were stored at −80° C. until LC/MS/MS assays.

The concentrations of compounds in the incubation mixtures of human (or rat) liver microsomes were determined by a LC/MS/MS method. The ranges of the linearity in the concentration range were determined for each tested compounds.

A parallel incubation was performed using denatured microsomes as the negative control, and reactions were terminated at various time points (for example, 0, 15, 60 min) after incubation at 37° C.

Dextromethorphan (70 μM) was selected as the positive control, and reactions were terminated at various time points (0, 5, 10, 15, 30, 60 min) after incubation at 37° C. Both positive and negative control samples were included in each assay to ensure the integrity of the microsomal incubation system.

Alternatively, the stability of some of the compounds disclosed herein in human (or rat) liver microsomes were also conducted in the following protocol. The incubations were conducted in duplicate in polypropylene tubes. The typical incubation mixtures consisted of liver microsomes (final concentration: 0.5 mg protein/mL), compounds (final concentration: 1.5 μM) in a total volume of 30 μL K-buffer (contain 1.0 mM EDTA, 100 mM, pH7.4). Compounds were dissolved in DMSO and diluted with K-buffer such that the final concentration of DMSO was 0.2%. The enzymatic reactions were commenced with the addition of 15 μL of NADPH (final concentration: 2 mM) after 10 min preincubation and incubated in a 37° C. incubator. Reactions were terminated at various time points (0, 15, 30, 60 min) by adding 135 μL acetonitrile (contain IS). Protein is removed by centrifugation with 4,000 rpm, 10 min.

Supernatant was Collected for LCMS/MS Analysis

In the above protocol, ketanserin (1 μM) was selected as the positive control, and reactions were terminated at various time points (0, 15, 30, 60 min) after incubation at 37° C. The positive control sample was included in each assay to ensure the integrity of the microsomal incubation system.

Data Analysis

The concentrations of compounds in liver microsome incubations were plotted as a percentage of the relevant zero time point control for each reaction. The in vivo $CL_{int}$ were extrapolated (ref: Naritomi et al., Prediction of human hepatic clearance from in vivo animal experiments and in vitro metabolic studies with liver microsomes from animals and humans, *Drug Metab. Dispos.*, 2001, 29: 1316-1324.)

Exemplary results from selected compounds of the invention are listed in Table 2. The compounds disclosed herein exhibited desirable half-life ($T_{1/2}$) and clearance ($CL_{int}$) when the compounds were incubated in human and rat liver microsomes. Similarly, selected compounds of the invention were also assessed for their stability in human and rat plasma, and the results are listed in Table 3.

TABLE 2

Stability of selected compounds of the invention in human and rat liver microsomes (1 μM)

| | Human | | Rat | |
|---|---|---|---|---|
| Example # | $T_{1/2}$ (min) | $CL_{int}$ (mL/min/kg) | $T_{1/2}$ (min) | $CL_{int}$ (mL/min/kg) |
| Ex. 1 | 28.89 | 60.17 | 17.54 | 141.60 |
| Ex. 2 | 59.49 | 29.22 | 12.85 | 193.28 |
| Ex. 7a | ∞ | ND | 53.06 | 46.81 |

TABLE 2-continued

Stability of selected compounds of the invention in human and rat liver microsomes (1 μM)

| | Human | | Rat | |
|---|---|---|---|---|
| Example # | $T_{1/2}$ (min) | $CL_{int}$ (mL/min/kg) | $T_{1/2}$ (min) | $CL_{int}$ (mL/min/kg) |
| Ex. 9 | | FTV | NT | NT |
| Ex. 10 | | FTV | | FTV |
| Ex. 11 | | FTV | | FTV |
| Ex. 14 | 33.62 | 51.7 | NT | NT |
| Ex. 18 | 78.77 | 5.52 | NT | NT |
| Ex. 19 | | FTV | | FTV |
| Ex. 20 | | FTV | | FTV |
| Ex. 21 | | FTV | | FTV |
| Ex. 22 | 72.8 | 23.9 | 4.6 | 535.4 |
| Ex. 23 | 112.8 | 15.4 | 5.8 | 429.2 |
| Ex. 25 | ∞ | ND | ∞ | ND |
| Ex. 26 | | FTV | NT | NT |
| Ex. 27 | | FTV | | FTV |
| Ex. 28 | | FTV | | FTV |
| Ex. 32 | ∞ | ND | ∞ | ND |

FTV: Fast Transformed to Vemurafenib;
NT: not tested;
ND: not determined

TABLE 3

Stability of selected compounds of the invention in human and rat plasma (2 μM)

| Example # | Human $T_{1/2}$ (min) | Rat $T_{1/2}$ (min) |
|---|---|---|
| Ex. 7a | ∞ | 68.82 |
| Ex. 9 | 112.9 | 28.55 |
| Ex. 10 | 88.12 | 55.78 |
| Ex. 11 | 162.2 | 49.80 |
| Ex. 14 | 510.8 | NT |
| Ex. 15 | 39.61 | 18.57 |
| Ex. 16 | ∞ | 157.3 |
| Ex. 18 | 6.08 | 9.61 |
| Ex. 19 | 7.47 | 5.90 |
| Ex. 22 | 6.81 | 15.24 |
| Ex. 23 | 3.06 | 3.42 |
| Ex. 26 | 81.6 | NT |
| Ex. 27 | 79.63 | 55.85 |
| Ex. 28 | 57.87 | 49.55 |
| Ex. 30 | ∞ | 56.32 |

NT: not tested

Example C

Evaluation of Pharmacokinetics after Intravenous and Oral Administration of the Compounds Disclosed Herein in Mice, Rats, Dogs and Monkeys Selected compounds of the invention and Vemurafenib were assessed in pharmacokinetic studies in mice, rats, dogs or monkeys. The compounds were administered as a water solution, 2% HPMC+1% TWEEN® 80 in water solution, 5% DMSO+5% solutol in saline, 4% MC or capsule. For the intravenous administration, the animals were generally given at 1 or 2 mg/kg dose. For the oral (p.o.) dosing, mice and rats were generally given 5 or 10 mg/kg dose, and dogs and monkeys were generally given 7-100 mg/kg dose. The blood samples (0.3 mL) were drawn at 0.25, 0.5, 1.0, 2.0, 3.0, 4.0, 6.0, 8.0, 12 and 24 h time points or 0.083, 0.25, 0.5, 1.0, 2.0, 4.0, 6.0, 8.0 and 24 h time points and centrifuged at 3,000 or 4000 rpm for 2 to 10 min. The plasma solutions are collected and stored at −20° C. or −70° C. before analyzed by LC/MS/MS as described above.

Exemplary study results from examples disclosed herein are listed in Table 4 to Table 8. The compounds disclosed herein exhibited optimized pharmacokinetic properties with desirable bioavailability (F) and half-life ($T_{1/2}$) when the compounds were administered intravenously or orally.

TABLE 4

Vemurafenib's Pharmacokinetic profiles in SD rats

| Sample | Dose mg/kg | $T_{1/2}$ h | $T_{max}$ h | $C_{max}$ ng/ml | $AUC_{last}$ ng·h/mL | F % |
|---|---|---|---|---|---|---|
| Vemurafenib | PO 10 | 3.54 | 4 | 25420 | 261424 | 104 |
|  | IV 1 | 3.75 | NT | NT | 25217 | / |

NT: not tested

TABLE 5

Pharmacokinetic profiles of selected compounds of the invention in SD rats (PO, 10 mg/kg dosing)

| Example # | $T_{1/2}$ h | $T_{max}$ h | $C_{max}$ ng/ml | $AUC_{last}$ ng·h/mL | F (Vemurafenib) % |
|---|---|---|---|---|---|
| Ex. 1 | 3.7 | 2.67 | 21317 | 171658 | 78.1 |
| Ex. 2 | 5.8 | 3.33 | 14801 | 134580 | 64.7 |
| Ex. 7a | 3.82 | 2.33 | 28468 | 272090 | 133 |
| Ex. 9 | 2.57 | 1.67 | 25875 | 194649 | 93 |
| Ex. 10 | 2.39 | 1.333 | 25889 | 232744 | 111 |
| Ex. 11 | 3.77 | 2 | 23022 | 226462 | 113 |
| Ex. 14 | 2.97 | 2.667 | 27645 | 196280 | 96.0 |
| Ex. 15 | 2.63 | 1.67 | 31024 | 273056 | 127 |
| Ex. 16 | 4.91 | 3.33 | 5806 | 76466 | 39.1 |
| Ex. 18 | 3.47 | 4.67 | 17473 | 229429 | 115 |
| Ex. 19 | 7.78 | 4.00 | 20050 | 311059 | 145 |
| Ex. 20 | 2.50 | 2.00 | 25460 | 169136 | 80.9 |
| Ex. 21 | 2.69 | 1.33 | 19643 | 118729 | 58.2 |
| Ex. 22 | 3.10 | 1.67 | 18935 | 182035 | 187 |
| Ex. 23 | 3.46 | 1.33 | 23106 | 183843 | 188 |
| Ex. 25 | 3.25 | 2.67 | 12774 | 114018 | 59.4 |
| Ex. 26 | 2.36 | 1.67 | 29520 | 170624 | 81.8 |
| Ex. 27 | 3.56 | 3.33 | 62049 | 348111 | 171 |
| Ex. 28 | 3.28 | 1.67 | 15870 | 154036 | 75.6 |
| Ex. 30 | 3.84 | 2.67 | 24882 | 252715 | 127 |

TABLE 6

Vemurafenib's Pharmacokinetic profiles in beagle dogs

| Sample | Dosing mg/kg | $T_{1/2}$ h | $T_{max}$ h | $C_{max}$ ng/ml | $AUC_{last}$ ng·h/mL | F % |
|---|---|---|---|---|---|---|
| Vemurafenib | PO 10 | 3.9 | 2 | 2149 | 16537 | 33.4 |
|  | IV 1 | 1.59 | NT | NT | 4877 | / |

NT: not tested

TABLE 7

Pharmacokinetic profiles of selected compounds of the invention in beagle dogs (PO)

| Example # | PO Dosing mg/kg | $T_{1/2}$ h | $T_{max}$ h | $C_{max}$ ng/ml | $AUC_{last}$ ng·h/mL | F (Vemurafenib) % |
|---|---|---|---|---|---|---|
| Ex. 25 | 10 | 1.94 | 4 | 2208 | 19057 | 47.9 |
|  | 40 | 1.95 | 4 | 12843 | 144162 | 90.5 |
|  | 70 | 1.84 | 2 | 38 | 173008 | 62.1 |
| Ex. 32 | 30 | 1.37 | 4 | 22200 | 125254 | 109 |
|  | 50 | 1.71 | 4 | 29900 | 210190 | 183 |

TABLE 8

Pharmacokinetic profiles of Example 25 in Monkeys (PO)

| Example # | PO Dosing mg/kg | $T_{1/2}$ h | $T_{max}$ h | $C_{max}$ ng/ml | $AUC_{last}$ ng·h/mL |
|---|---|---|---|---|---|
| Ex. 25 | 50 | 9.32 | 4 | 22136 | 225569 |
|  | 50 | 12.07 | 4 | 23038 | 247859 |
|  | 100 | 27.04 | 4 | 34793 | 467762 |

Example D

Tumor Xenograft Models

The efficacy of compounds disclosed herein is evaluated in a standard murine model of tumorigenesis. Human tumor cells (i.e., Colo-205 Tumor Xenograft models) are expended in culture, harvested, and injected subcutaneously onto the rear flank of 6-7 week old female athymic nude mice (BALB/cA nu/nu, Shanghai SLAC Laboratory Animal, Co.) (n=10 for vehicle group, n=8 for each dosing group). When tumor reaches a volume of 100-250 mm$^3$, animals are randomly divided into vehicle control (for example, 5% PEG400+5% Solutol HS 15 in water or 5% EtOH+5% CremophorEL+1% HCl (11.7%), pH 2.2 in water) and compound groups. Subsequent administration of compound by oral gavage (for example, 6-60 mpk/dose, dissolved in 5% PEG400+5% Solutol HS 15 in water or 5% EtOH+5% CremophorEL+1% HCl (11.7%), pH 2.2 in water) begins anywhere from day 0 to day 15 post tumor cell challenge and generally continues with once a day for the duration of the experiment.

Tumor Growth Inhibition (TGI) Analysis

Progression of tumor growth is assessed by tumor volumes and recorded as a function of time. The long (L) and short (W) axes of the subcutaneous tumors are measured with calipers twice weekly, and the tumor volume (TV) calculated as (L×W$^2$)/2). TGI is calculated from the difference between the median tumor volumes of vehicle-treated and drug-treated mice, expressed as a percentage of the median tumor volume of the vehicle-treated control group, by the following relation:

$$\% \ TGI = \left( \frac{\text{Median Tumor Volume}_{control} - \text{Median Tumor Volume}_{drug\text{-}treated}}{\text{Median Tumor Volume}_{control}} \right) \times 100$$

Initial statistical analysis is done by repeated measures analysis of variance (RMANOVA), Followed by Scheffe post-hoc testing for multiple comparisons. Vehicle alone (2% HPMC+1% Tween-80, or the like) is the negative control.

The compounds described herein were also administrated orally (p.o.) once a day (QD) or (BID) for 15 days in Colo-205 xenograft animal model. At doses of 20 mg/kg, the compouds produced statistically significant inhibition of growth of certain tumors grown subcutaneously in athymic nude mice. Exemplary xenograft study results from Examples 25, 32 are listed in Table 9.

TABLE 9

| TGI % of Colo-205 Xenograft models | | | | |
| --- | --- | --- | --- | --- |
| TGI % (on the last day of dosing) | Colo-205 Xenograft models | | | |
| | 6 mg/kg/qd | 20 mg/kg/qd | 20 mg/kg/bid | 60 mg/kg/qd |
| Vemurafenib (15 days) | 33 | 73 | 101 | 104 |
| Ex. 25 (15 days) | 41 | 59 | 95 | 108 |
| Ex. 32 (15 days) | 29 | 68 | 102 | 110 |

The compounds disclosed herein exhibited optimized pharmacokinetic properties with desirable clearance (CL), half-life ($T_{1/2}$) and excellent bioavailability when the compounds were administered intravenously or orally.

Finally, it should be noted that there are alternative ways of implementing the present invention. Accordingly, the present embodiments are to be considered as illustrative and not restrictive and the invention is not be limited to the details given herein, but may be modified within the scope and equivalents of the appended claims. All publications and patents cited herein are incorporated by reference.

What is claimed is:

1. A compound of Formula (I):

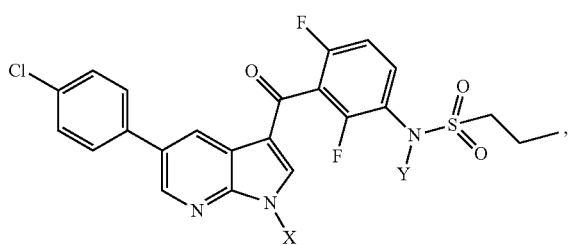

(I)

or a racemic mixture, a stereoisomer, a geometric isomer, a tautomer, a solvate, an N-oxide, a metabolite or a pharmaceutically acceptable salt thereof, wherein:

each of X and Y is independently H, —C(=O)$R^3$, —C(=O)O$R^4$, —C($R^1R^2$)OC(=O)$R^3$, —C($R^1R^2$)OC(=O)O$R^4$ or —C($R^1R^2$)OP(=O)(O$R^4$)(O$R^{4a}$), with the proviso that when Y is H, X is not —C(=O)CH$_3$ or H;

each $R^1$ and $R^2$ is independently H, D, $C_{1-6}$alkyl, $C_{1-6}$haloalkyl, $C_{3-6}$cycloalkyl, —($C_{1-4}$ alkylene)-($C_{3-6}$cycloalkyl), $C_{3-6}$heterocyclyl or —($C_{1-4}$alkylene)-($C_{3-6}$ heterocyclyl); or $R^1$ and $R^2$, together with the carbon atom they are attached to, form an unsubstituted or substituted 3-8 membered carbocyclic or heterocyclic ring;

each $R^3$ is independently H, D, $C_{1-10}$haloalkyl, $C_{3-8}$cycloalkyl, —($C_{1-6}$ alkylene)-($C_{3-8}$cycloalkyl), $C_{3-8}$heterocyclyl, —($C_{1-6}$alkylene)-($C_{3-8}$heterocyclyl), $C_{6-10}$aryl, —($C_{1-6}$alkylene)-($C_{6-10}$aryl), 5-10 membered heteroaryl or —($C_{1-6}$alkylene)-(5-10 membered heteroaryl), wherein each of the $C_{1-10}$alkyl, $C_{1-10}$haloalkyl, $C_{3-8}$cycloalkyl, —($C_{1-6}$alkylene)-($C_{3-8}$cycloalkyl), $C_{3-8}$heterocyclyl, —($C_{1-6}$alkylene)-($C_{3-8}$heterocyclyl), $C_{6-10}$aryl, —($C_{1-6}$ alkylene)-($C_{6-10}$aryl), 5-10 membered heteroaryl and —($C_{1-6}$alkylene)-(5-10 membered heteroaryl) is unsubstituted or optionally substituted with 1, 2, 3 or 4 substituents independently selected from D, F, Br, I, $C_{1-6}$alkyl, $C_{1-6}$haloalkyl, OH, NH$_2$, $C_{1-6}$ alkoxy and $C_{1-6}$alkylamino; and each $R^4$ and $R^{4a}$ is independently H, $C_{1-10}$haloalkyl, $C_{3-8}$cycloalkyl, —($C_{1-6}$ alkylene)-($C_{3-8}$cycloalkyl), $C_{3-8}$heterocyclyl, —($C_{1-6}$alkylene)-($C_{3-8}$heterocyclyl), $C_{6-10}$aryl, —($C_{1-6}$alkylene)-($C_{6-10}$aryl), 5-10 membered heteroaryl or —($C_{1-6}$alkylene)-(5-10 membered heteroaryl), wherein each of the $C_{1-10}$alkyl, $C_{3-8}$cycloalkyl, —($C_{1-6}$alkylene)-($C_{3-8}$cycloalkyl), $C_{3-8}$heterocyclyl, —($C_{1-6}$alkylene)-($C_{3-8}$heterocyclyl), $C_{6-10}$aryl, —($C_{1-6}$ alkylene)-($C_{6-10}$aryl), 5-10 membered heteroaryl and —($C_{1-6}$alkylene)-(5-10 membered heteroaryl) is unsubstituted or optionally substituted with 1, 2, 3 or 4 substituents independently selected from D, F, Cl, OH, NH$_2$, oxo (=O), $C_{1-6}$haloalkyl, $C_{1-6}$ alkoxy and $C_{1-6}$alkylamino.

2. The compound of claim 1, wherein each $R^1$ and $R^2$ is independently H, D or $C_{1-3}$ alkyl.

3. The compound of claim 1, wherein each $R^3$ is independently $C_{1-10}$alkyl, $C_{3-8}$ cycloalkyl, —($C_{1-6}$alkylene)-($C_{3-8}$cycloalkyl), $C_{3-8}$heterocyclyl, —($C_{1-6}$alkylene)-($C_{3-8}$heterocyclyl), $C_{6-10}$aryl, —($C_{1-6}$alkylene)-($C_{6-10}$aryl), 5-10 membered heteroaryl or —($C_{1-6}$ alkylene)-(5-10 membered heteroaryl), wherein each of the $C_{1-10}$alkyl, $C_{3-8}$cycloalkyl, —($C_{1-6}$alkylene)-($C_{3-8}$cycloalkyl), $C_{3-8}$heterocyclyl, —($C_{1-6}$alkylene)-($C_{3-8}$heterocyclyl), $C_{6-10}$ aryl, —($C_{1-6}$alkylene)-($C_{6-10}$aryl), 5-10 membered heteroaryl and —($C_{1-6}$ alkylene)-(5-10 membered heteroaryl) is unsubstituted or optionally substituted with 1, 2, 3 or 4 substituents independently selected from D, F, OH, OMe, NH$_2$, NHMe, NMe$_2$ and $C_{1-3}$ alkyl.

4. The compound of claim 1, wherein each $R^4$ and $R^{4a}$ is independently H, $C_{1-10}$ alkyl, $C_{3-8}$cycloalkyl, —($C_{1-6}$alkylene)-($C_{3-8}$cycloalkyl), $C_{3-8}$heterocyclyl, —($C_{1-6}$alkylene)-($C_{3-8}$heterocyclyl) or $C_{6-10}$aryl, wherein each of the $C_{1-10}$alkyl, $C_{3-8}$cycloalkyl, —($C_{1-6}$ alkylene)-($C_{3-8}$cycloalkyl), $C_{3-8}$heterocyclyl, —($C_{1-6}$alkylene)-($C_{3-8}$heterocyclyl) and $C_{6-10}$ aryl is unsubstituted or optionally substituted with 1, 2, 3 or 4 substituents independently selected from D, F, OH, OMe, oxo (=O), NH$_2$, NHMe, NMe$_2$ and $C_{1-3}$ alkyl.

5. The compound of claim 1, wherein each of X and Y is independently H or —C($R^1R^2$)OP(=O)(OH)$_2$, with the proviso that when Y is H, X is not H.

6. The compound of claim 1, wherein each of X and Y is independently H, —C(=O)$R^3$, —C(=O)O$R^4$, —C($R^1R^2$)OC(=O)$R^3$ or —C($R^1R^2$)OC(=O)O$R^4$, with the proviso that when Y is H, X is not —C(=O)CH$_3$ or H.

7. The compound of claim 6, wherein the acyl moiety (—C(=O)$R^3$) is derived from an α-amino acid or an optical isomer thereof by removing the OH group from the carboxy group of the α-amino acid.

8. The compound of claim 7, wherein the α-amino acid is isoleucine, leucine, lysine, methionine, phenylalanine, threonine, tryptophan, valine, alanine, asparagine, aspartate, glutamate, glutamine, proline, serine, para-tyrosine, arginine, histidine, cysteine, glycine, sarcosine, N,N-dimethyl glycine, homoserine, norvaline, norleucine, ornithine, homocysteine, homophenylalanine, phenylglycine, ortho-tyrosine, meta-tyrosine or hydroxyproline.

9. The compound of claim 8, wherein the α-amino acid is isoleucine, leucine, lysine, methionine, phenylalanine, threonine, tryptophan, valine, alanine, asparagine, aspartate, glutamate, glutamine, proline, serine, tyrosine, arginine or histidine, each of which has a S-configuration at the α-position.

10. The compound of claim 1, wherein the pharmaceutically acceptable salt is an alkali metal salt, an alkaline earth metal salt, or an ammonium or N$^+$($C_{1-4}$ alkyl)$_4$ salt.

11. The compound of claim 10, wherein the pharmaceutically acceptable salt is a sodium salt, a lithium salt, a potassium salt, a calcium salt, a magnesium salt, an ammonium salt, a quaternary ammonium salt, or a combination thereof.

12. The compound of claim 1, wherein the pharmaceutically acceptable salt is a salt of an inorganic acid, an organic acid or a combination thereof, wherein the inorganic acid or the organic acid is hydrochloric acid, hydrobromic acid, sulfuric acid, nitric acid, phosphoric acid, acetic acid, maleic acid, succinic acid, mandelic acid, fumaric acid, malonic acid, malic acid, 2-hydroxypropanic acid, pyruvic acid, oxalic acid, glycolic acid, salicylic acid, glucuronic acid, galacturonic acid, citric acid, tartaric acid, aspartic acid, glutamic acid, benzoic acid, cinnamic acid, p-toluenesulfonic acid, benzenesulfonic acid, mthanesulfonic acid, ethanesulfonic acid, trifluoromthanesulfonic acid or a combination thereof.

13. The compound of claim 1 having one of the following structures:

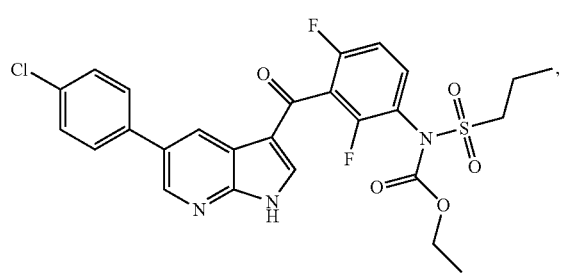

(1)

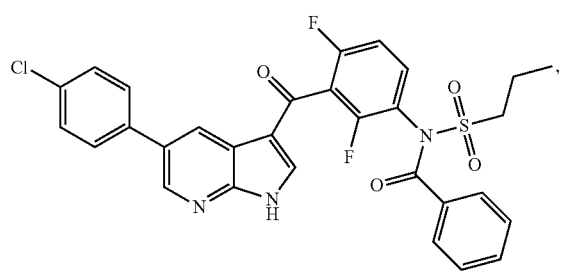

(2)

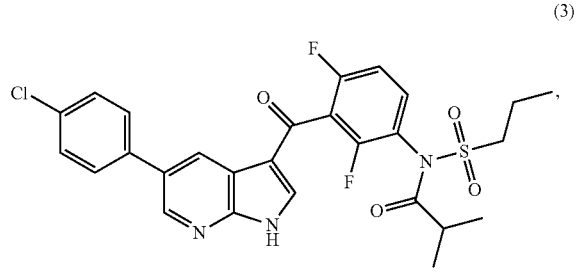

(3)

(4)

(5)

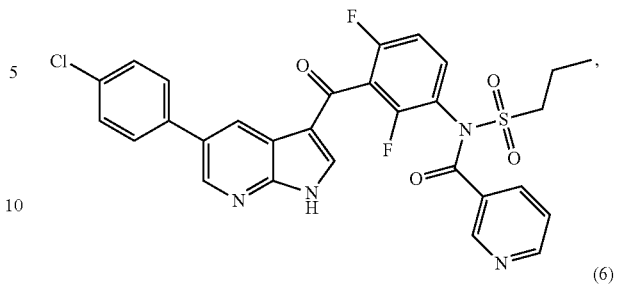

(6)

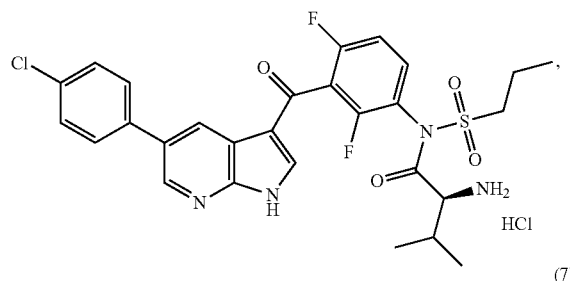

(7)

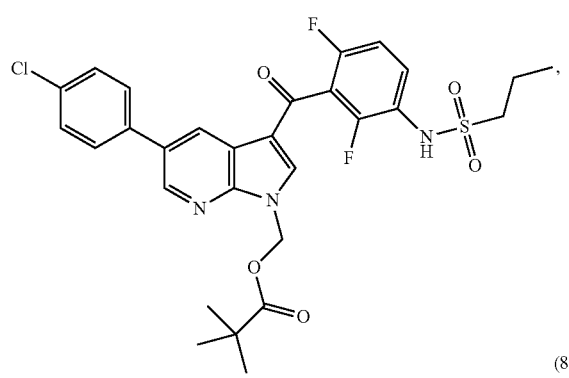

(8)

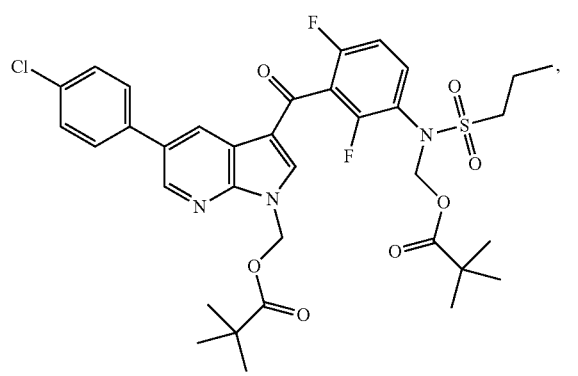

(9)

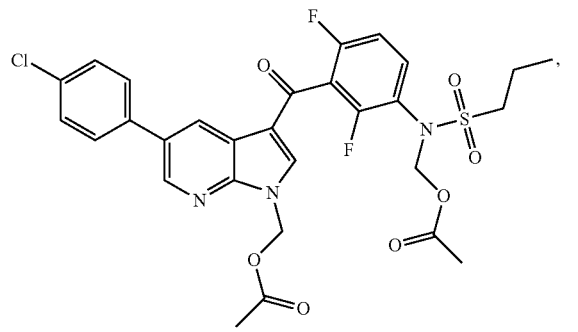

-continued
(10)
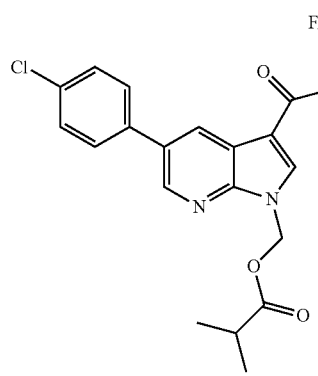
(11)
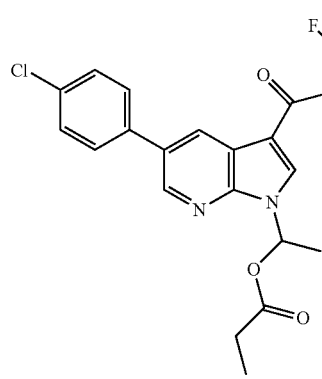
(12)
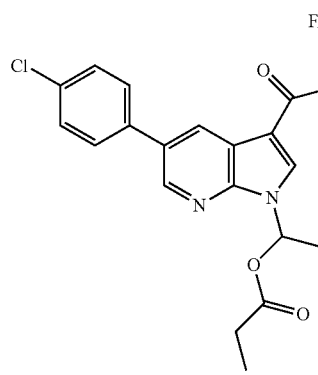
(13)
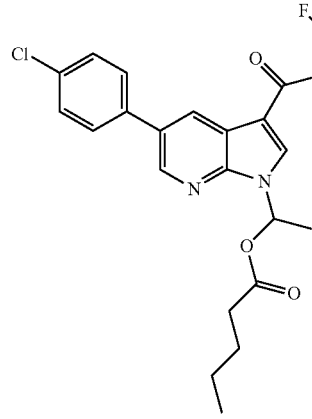
-continued
(14)
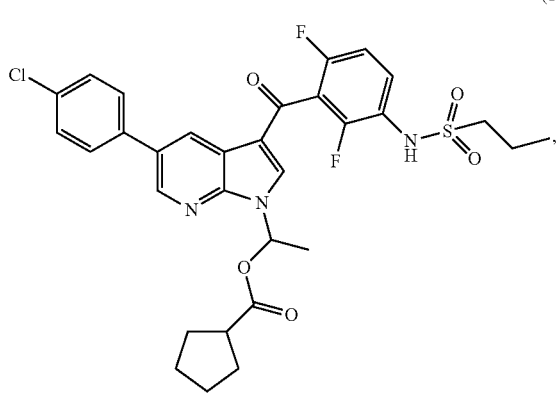
(15)
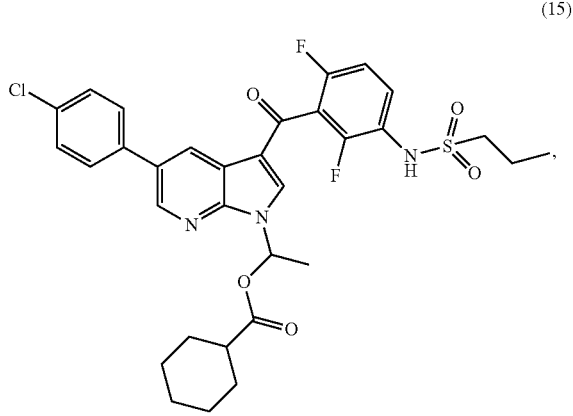
(16)
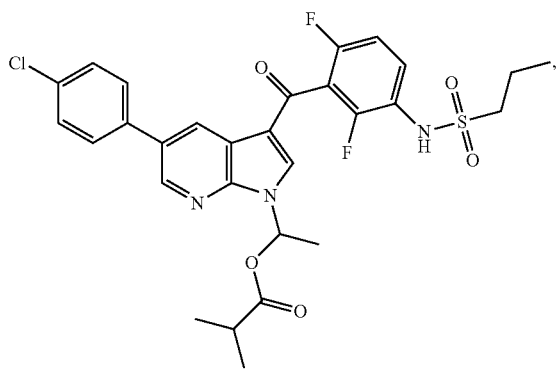
(17)
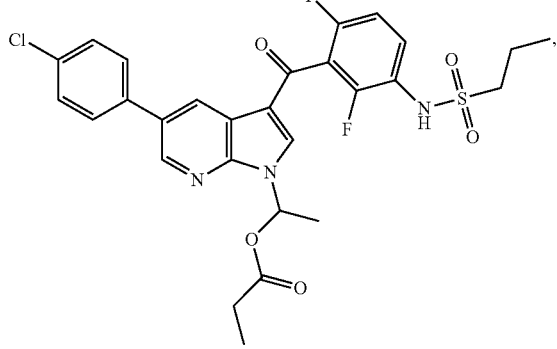

(18)
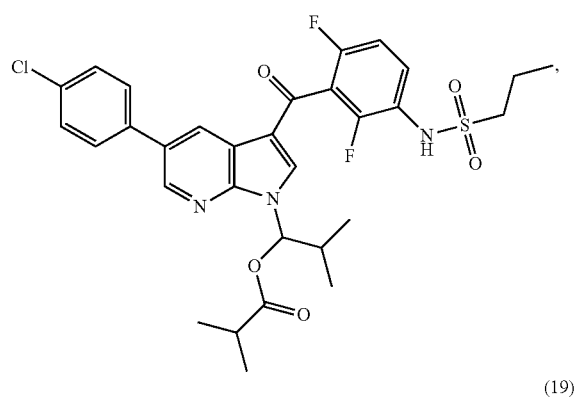
(19)
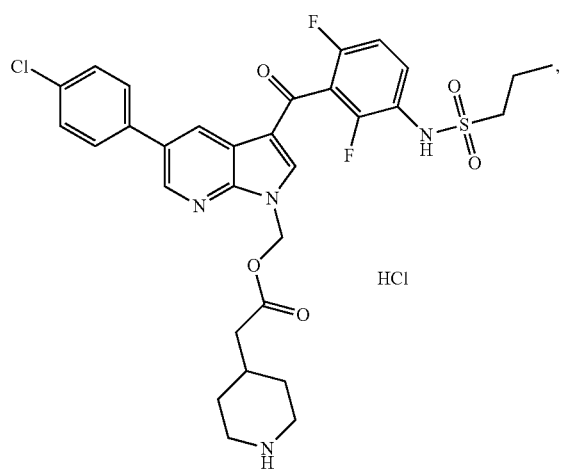
HCl
(20)
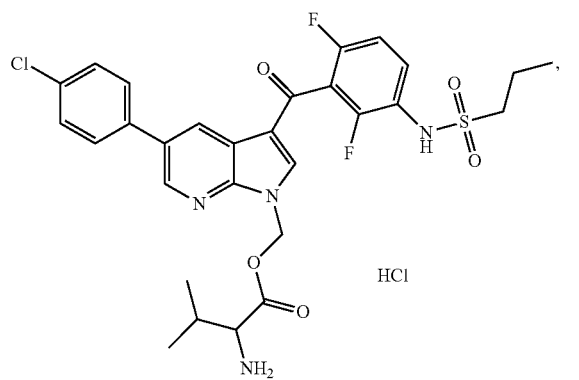
HCl
(21)
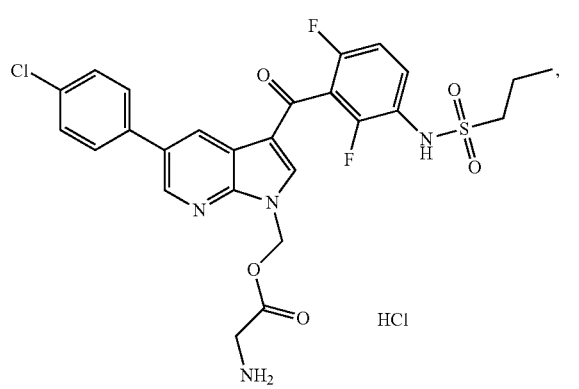
HCl
(22)
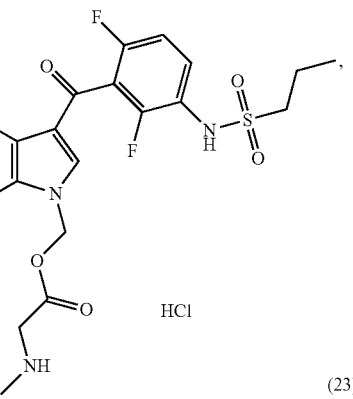
HCl
(23)
HCl
(24)
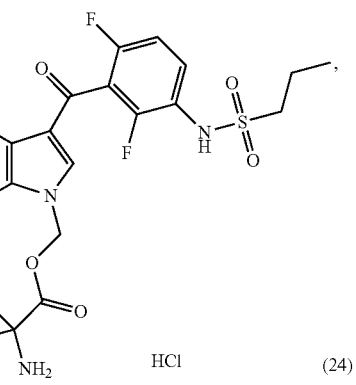
(25)
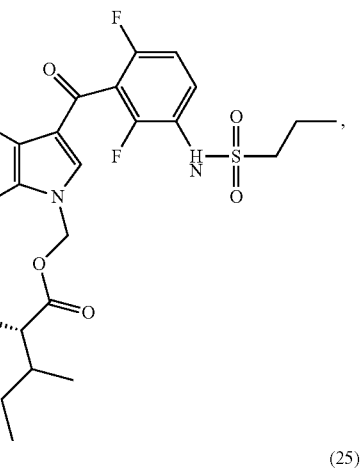
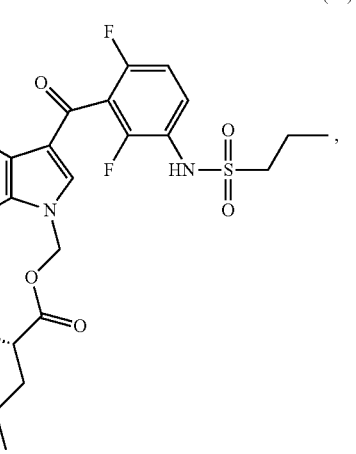

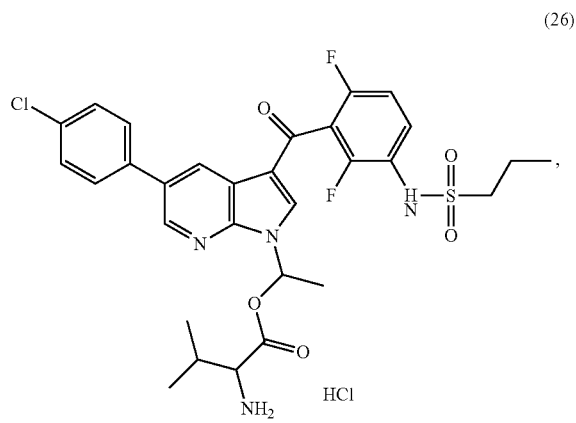
(26)
(27)
(28)
(29)
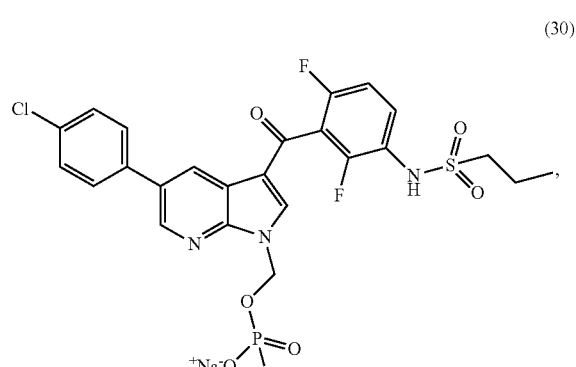
(30)
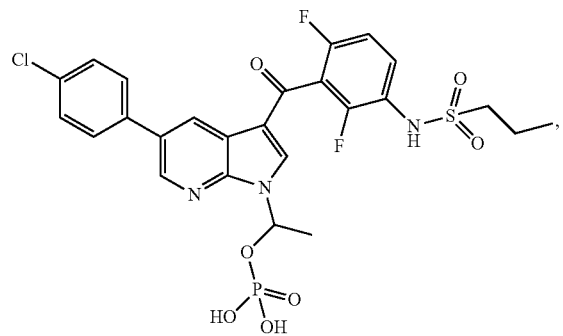
(31)
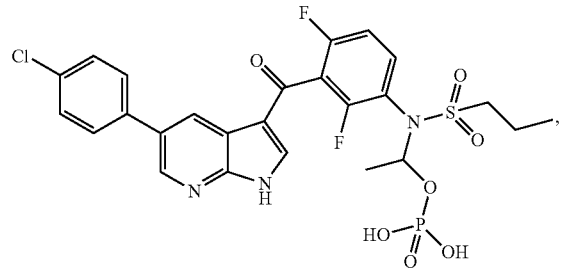
(32)
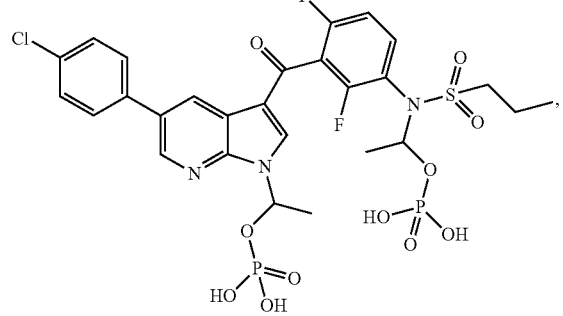
(33)

-continued
(34)
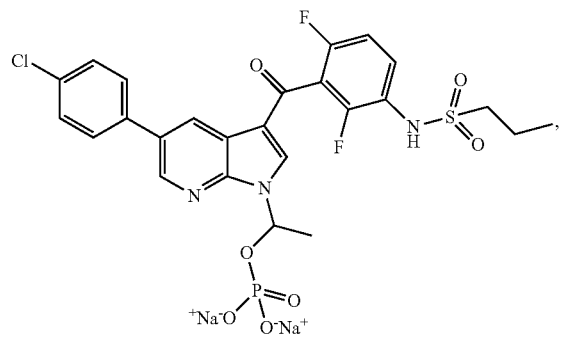
(35)
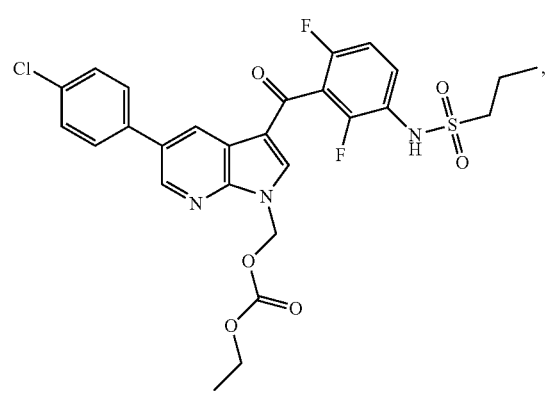
(36)
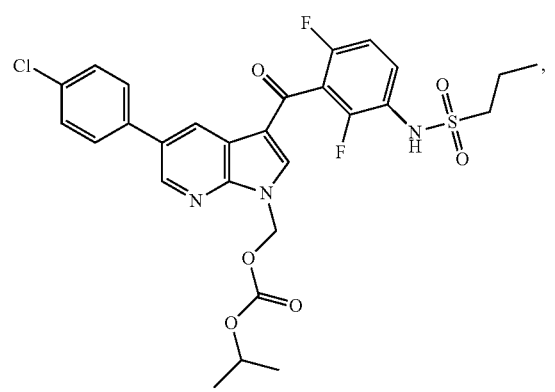
(37)
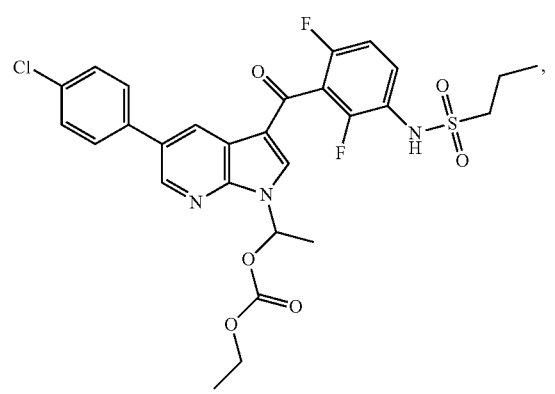
-continued
(38)
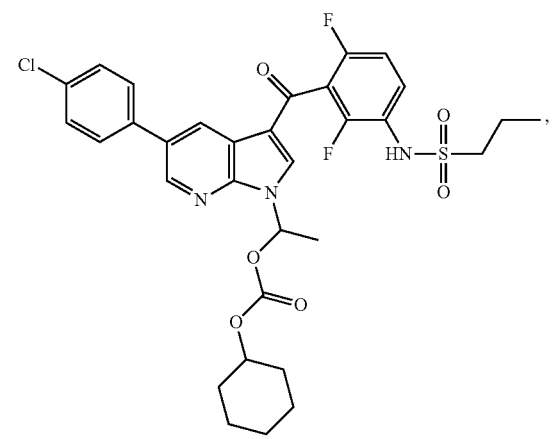
(39)
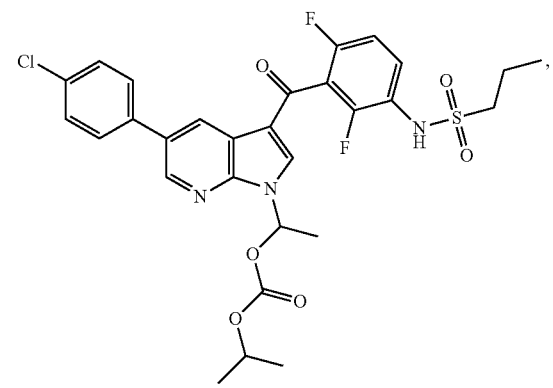
(40)
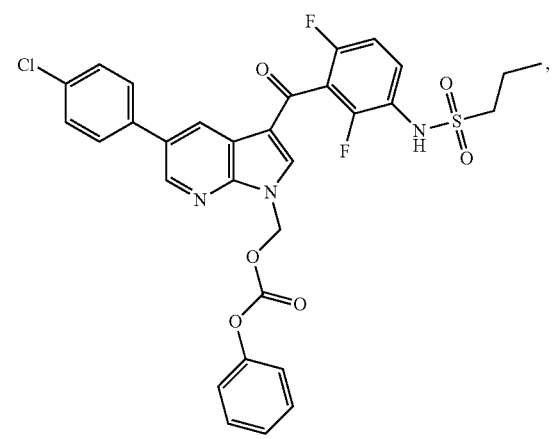

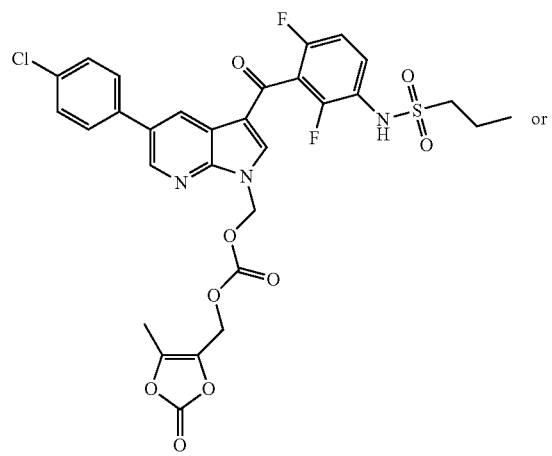
(41)
or
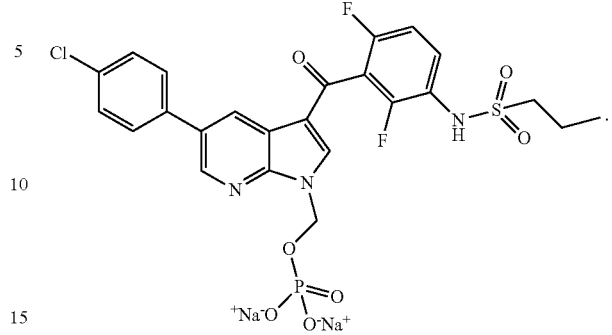
(42)
14. A pharmaceutical composition comprising the compound of claim 1, and a pharmaceutically acceptable carrier, excipient, diluent, adjuvant, vehicle or a combination thereof.
* * * * *